United States Patent
Atsumi et al.

(10) Patent No.: US 9,428,773 B2
(45) Date of Patent: Aug. 30, 2016

(54) METHODS OF PRODUCING ACETOIN AND 2,3-BUTANEDIOL USING PHOTOSYNTHETIC MICROORGANISMS

(71) Applicant: The Regents of the University of California, Oakland, CA (US)

(72) Inventors: Shota Atsumi, Davis, CA (US); John W. K. Oliver, Davis, CA (US); Iara M. P. Machado, Davis, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 14/431,747

(22) PCT Filed: Sep. 27, 2013

(86) PCT No.: PCT/US2013/062459
§ 371 (c)(1),
(2) Date: Mar. 26, 2015

(87) PCT Pub. No.: WO2014/052920
PCT Pub. Date: Apr. 3, 2014

(65) Prior Publication Data
US 2015/0259711 A1   Sep. 17, 2015

Related U.S. Application Data

(60) Provisional application No. 61/707,866, filed on Sep. 28, 2012.

(51) Int. Cl.
| | | |
|---|---|---|
| *C12P 7/04* | (2006.01) | |
| *C12N 15/63* | (2006.01) | |
| *C12P 7/26* | (2006.01) | |
| *C12N 9/10* | (2006.01) | |
| *C12N 9/88* | (2006.01) | |
| *C12P 7/18* | (2006.01) | |
| *C12N 9/04* | (2006.01) | |

(52) U.S. Cl.
CPC ............... *C12P 7/26* (2013.01); *C12N 9/0006* (2013.01); *C12N 9/1022* (2013.01); *C12N 9/88* (2013.01); *C12P 7/18* (2013.01); *C12Y 202/01006* (2013.01); *C12Y 401/01005* (2013.01); *C12Y 101/98* (2013.01); *Y02P 20/52* (2015.11)

(58) Field of Classification Search
CPC ................................. C12P 7/04; C12N 15/63
USPC ...................................................... 435/252.3
See application file for complete search history.

(56) References Cited

U.S. PATENT DOCUMENTS

| | | | |
|---|---|---|---|
| 6,699,696 B2 | 3/2004 | Woods et al. | |
| 2007/0259410 A1 | 11/2007 | Donaldson et al. | |
| 2008/0274525 A1 | 11/2008 | Bramucci et al. | |
| 2009/0239275 A1 | 9/2009 | Donaldson et al. | |
| 2010/0112655 A1 | 5/2010 | Paul et al. | |
| 2011/0212498 A1* | 9/2011 | Hellingwerf | C12N 1/20 435/139 |
| 2012/0184002 A1 | 7/2012 | Wall et al. | |
| 2014/0342419 A1* | 11/2014 | Dischert | C12N 15/52 435/158 |

OTHER PUBLICATIONS

Atsumi et al. 2009. "Direct photosynthetic recycling of carbon dioxide to isobutyraldehyde," Nat Biotechnol. 27(12): 1177-80. Epub Nov. 15, 2009.
Machado and Atsumi. 2012. "Cyanobacterial biofuel production," J Biotechnol. 162(1): 50-56. Epub Mar. 16, 2012.
McEwen et al. 2013. "Engineering Synechococcus elongatus PCC 7942 for continuous growth under diurnal conditions," Appl Environ Microbiol. 79(5): 1668-1675. Epub Dec. 28, 2012.
Mirhendi et al. 2010. "Molecular screening for Candida orthopsilosis and Candida metapsilosis among Danish Candida parapsilosis group blood culture isolates: proposal of a new RFLP profile for differentiation," J Med Microbiol. 59: 414-420.
Oliver et al. 2014. "Combinatorial optimization of cyanobacterial 2,3-butanediol production," Metab Eng. 22: 76-82. Epub Jan. 9, 2014.
Oliver et al. 2013. "Cyanobacterial conversion of carbon dioxide to 2,3-butanediol," Proc Natl Acad Sci USA. 110(4): 1249-1254 and 6 pages of supporting information. Epub Jan. 7, 2013.
International Preliminary Report on Patentability received for PCT Patent Application No. PCT/US2013/062459, mailed on Apr. 9, 2015, 11 pages.
Invitation to Pay Additional Fee received for PCT Patent Application No. PCT/US2013/062459, mailed on Feb. 20, 2014, 2 pages.
International Search Report and Written Opinion received for PCT Patent Application No. PCT/US2013/062459, mailed on Apr. 22, 2014, 14 pages.
Speranza et al. 1997. "Conversion of meso-2,3-butanediol into 2-butanol by Lactobacilli. Stereochemical and enzymatic aspects," J Agric Food Chem. 45(9): 3476-3480.
Syu. 2001. "Biological production of 2,3-butanediol," Appl Microbiol Biotechnol. 55(1): 10-18.
Yan et al. 2009. "Enantioselective synthesis of pure (R,R)-2,3-butanediol in *Escherichia coli* with stereospecific secondary alcohol dehydrogenases," Org Biomol Chem. 7: 3914-3917. Epub Aug. 3, 2009.

* cited by examiner

*Primary Examiner* — Maryam Monshipouri
(74) *Attorney, Agent, or Firm* — Morrison & Foerster LLP

(57) ABSTRACT

The present disclosure provides recombinant cyanobacteria having acetolactate synthase activity and acetolactate decarboxylase activity, as well as recombinant cyanobacteria having acetolactate synthase activity, acetolactate decarboxylase activity, and secondary alcohol dehydrogenase activity. Methods for the production of the recombinant cyanobacteria, as well as methods for use thereof for production of acetoin and 2,3-butanediol from carbon dioxide and light are also provided.

20 Claims, 7 Drawing Sheets

SEQUENCE LISTING

```
<160> NUMBER OF SEQ ID NOS: 58

<210> SEQ ID NO 1
<211> LENGTH: 74
<212> TYPE: DNA
<213> ORGANISM: Artificial Sequence
<220> FEATURE:
<223> OTHER INFORMATION: Synthetic Construct

<400> SEQUENCE: 1
aattgtgagc ggataacaat tgacattgtg agcggataac aagatactga gcacatcagc       60
aggacgcact gacc                                                         74

<210> SEQ ID NO 2
<211> LENGTH: 1713
<212> TYPE: DNA
<213> ORGANISM: Bacillus subtilis

<400> SEQUENCE: 2
atgttgacaa aagcaacaaa agaacaaaaa tcccttgtga aaaacagagg ggcggagctt       60
gttgttgatt gcttagtgga gcaaggtgtc acacatgtat ttggcattcc aggtgcaaaa      120
```

```
attgatgcgg tatttgacgc tttacaagat aaaggacctg aaattatcgt tgcccggcac    180
gaacaaaacg cagcattcat ggcccaagca gtcggccgtt taactggaaa accgggagtc    240
gtgttagtca catcaggacc gggtgcctct aacttggcaa caggcctgct gacagcgaac    300
actgaaggag accctgtcgt tgcgcttgct ggaaacgtga tccgtgcaga tcgtttaaaa    360
cggacacatc aatctttgga taatgcggcg ctattccagc cgattacaaa atacagtgta    420
gaagttcaag atgtaaaaaa tataccggaa gctgttacaa atgcatttag gatagcgtca    480
gcagggcagg ctggggccgc ttttgtgagc tttccgcaag atgttgtgaa tgaagtcaca    540
aatacgaaaa acgtgcgtgc tgttgcagcg ccaaaactcg gtcctgcagc agatgatgca    600
atcagtgcgg ccatagcaaa aatccaaaca gcaaaacttc ctgtcgtttt ggtcggcatg    660
aaaggcggaa gaccggaagc aattaaagcg gttcgcaagc ttttgaaaaa ggttcagctt    720
ccatttgttg aaacatatca agctgccggt acccttccta gagatttaga ggatcaatat    780
tttggccgta tcggtttgtt ccgcaaccag cctggcgatt tactgctaga gcaggcagat    840
gttgttctga cgatcggcta tgacccgatt gaatatgatc cgaaattctg gaatatcaat    900
ggagaccgga caattatcca tttagacgag attatcgctg acattgatca tgcttaccag    960
cctgatcttg aattgatcgg tgacattccg tccacgatca atcatatcga acacgatgct    1020
gtgaaagtgg aatttgcaga gcgtgagcag aaaatccttt ctgatttaaa acaatatatg    1080
catgaaggtg agcaggtgcc tgcagattgg aaatcagaca gagcgcaccc tcttgaaatc    1140
gttaaagagt gcgtaatgc agtcgatgat catgttacag taacttgcga tatcggttcg    1200
cacgccattt ggatgtcacg ttatttccgc agctacgagc cgttaacatt aatgatcagt    1260
aacggtatgc aaacactcgg cgttgcgctt ccttgggcaa tcggcgcttc attggtgaaa    1320
ccgggagaaa aagtggtttc tgtctctggt gacggcggtt tcttattctc agcaatggaa    1380
ttagagacag cagttcgact aaaagcacca attgtacaca ttgtatggaa cgacagcaca    1440
tatgacatgg ttgcattcca gcaattgaaa aaatataacc gtacatctgc ggtcgatttc    1500
ggaaatatcg atatcgtgaa atatgcggaa agcttcggag caactggctt gcgcgtagaa    1560
tcaccagacc agctggcaga tgttctgcgt caaggcatga acgctgaagg tcctgtcatc    1620
atcgatgtcc cggttgacta cagtgataac attaatttag caagtgacaa gcttccgaaa    1680
gaattcgggg aactcatgaa aacgaaagct ctc                                  1713
```

<210> SEQ ID NO 3
<211> LENGTH: 571
<212> TYPE: PRT
<213> ORGANISM: Bacillus subtilis

<400> SEQUENCE: 3

Met Leu Thr Lys Ala Thr Lys Glu Gln Lys Ser Leu Val Lys Asn Arg
1               5                   10                  15

Gly Ala Glu Leu Val Val Asp Cys Leu Val Glu Gln Gly Val Thr His
            20                  25                  30

Val Phe Gly Ile Pro Gly Ala Lys Ile Asp Ala Val Phe Asp Ala Leu
        35                  40                  45

Gln Asp Lys Gly Pro Glu Ile Ile Val Ala Arg His Glu Gln Asn Ala
    50                  55                  60

Ala Phe Met Ala Gln Ala Val Gly Arg Leu Thr Gly Lys Pro Gly Val
65                  70                  75                  80

Val Leu Val Thr Ser Gly Pro Gly Ala Ser Asn Leu Ala Thr Gly Leu
            85                  90                  95

```
Leu Thr Ala Asn Thr Glu Gly Asp Pro Val Val Ala Leu Ala Gly Asn
            100                 105                 110

Val Ile Arg Ala Asp Arg Leu Lys Arg Thr His Gln Ser Leu Asp Asn
        115                 120                 125

Ala Ala Leu Phe Gln Pro Ile Thr Lys Tyr Ser Val Glu Val Gln Asp
    130                 135                 140

Val Lys Asn Ile Pro Glu Ala Val Thr Asn Ala Phe Arg Ile Ala Ser
145                 150                 155                 160

Ala Gly Gln Ala Gly Ala Ala Phe Val Ser Phe Pro Gln Asp Val Val
                165                 170                 175

Asn Glu Val Thr Asn Thr Lys Asn Val Arg Ala Val Ala Pro Lys
            180                 185                 190

Leu Gly Pro Ala Ala Asp Asp Ala Ile Ser Ala Ala Ile Ala Lys Ile
        195                 200                 205

Gln Thr Ala Lys Leu Pro Val Val Leu Val Gly Met Lys Gly Gly Arg
210                 215                 220

Pro Glu Ala Ile Lys Ala Val Arg Lys Leu Leu Lys Lys Val Gln Leu
225                 230                 235                 240

Pro Phe Val Glu Thr Tyr Gln Ala Ala Gly Thr Leu Ser Arg Asp Leu
                245                 250                 255

Glu Asp Gln Tyr Phe Gly Arg Ile Gly Leu Phe Arg Asn Gln Pro Gly
            260                 265                 270

Asp Leu Leu Glu Gln Ala Asp Val Val Leu Thr Ile Gly Tyr Asp
        275                 280                 285

Pro Ile Glu Tyr Asp Pro Lys Phe Trp Asn Ile Asn Gly Asp Arg Thr
        290                 295                 300

Ile Ile His Leu Asp Glu Ile Ile Ala Asp Ile Asp His Ala Tyr Gln
305                 310                 315                 320

Pro Asp Leu Glu Leu Ile Gly Asp Ile Pro Ser Thr Ile Asn His Ile
                325                 330                 335

Glu His Asp Ala Val Lys Val Glu Phe Ala Glu Arg Glu Gln Lys Ile
            340                 345                 350

Leu Ser Asp Leu Lys Gln Tyr Met His Glu Gly Glu Gln Val Pro Ala
        355                 360                 365

Asp Trp Lys Ser Asp Arg Ala His Pro Leu Glu Ile Val Lys Glu Leu
370                 375                 380

Arg Asn Ala Val Asp Asp His Val Thr Val Thr Cys Asp Ile Gly Ser
385                 390                 395                 400

His Ala Ile Trp Met Ser Arg Tyr Phe Arg Ser Tyr Glu Pro Leu Thr
                405                 410                 415

Leu Met Ile Ser Asn Gly Met Gln Thr Leu Gly Val Ala Leu Pro Trp
            420                 425                 430

Ala Ile Gly Ala Ser Leu Val Lys Pro Gly Glu Lys Val Val Ser Val
        435                 440                 445

Ser Gly Asp Gly Gly Phe Leu Phe Ser Ala Met Glu Leu Glu Thr Ala
450                 455                 460

Val Arg Leu Lys Ala Pro Ile Val His Ile Val Trp Asn Asp Ser Thr
465                 470                 475                 480

Tyr Asp Met Val Ala Phe Gln Gln Leu Lys Lys Tyr Asn Arg Thr Ser
                485                 490                 495

Ala Val Asp Phe Gly Asn Ile Asp Ile Val Lys Tyr Ala Glu Ser Phe
            500                 505                 510
```

Gly Ala Thr Gly Leu Arg Val Glu Ser Pro Asp Gln Leu Ala Asp Val
            515                 520                 525

Leu Arg Gln Gly Met Asn Ala Glu Gly Pro Val Ile Ile Asp Val Pro
        530                 535                 540

Val Asp Tyr Ser Asp Asn Ile Asn Leu Ala Ser Asp Lys Leu Pro Lys
545                 550                 555                 560

Glu Phe Gly Glu Leu Met Lys Thr Lys Ala Leu
                565                 570

<210> SEQ ID NO 4
<211> LENGTH: 780
<212> TYPE: DNA
<213> ORGANISM: Enterobacter aerogenes

<400> SEQUENCE: 4
atgaatcatg cttcagattg cacctgtgaa gagagtctgt gtgaaacgct acgcgcgttt      60
tccgctcagc atcccgatag cgtgctgtat caaacttcgc tgatgagcgc cctgctcagc     120
ggcgtctacg aaggtaccac caccattgcg gacctgctga gcacggtga tttcgggctc      180 ggcactttta tgaactcga cggcgagctg atcgcgttta gcagccaggt ttatcaactg      240
cgtgccgacg gcagcgcgcg taaagcgcgt ccggaacaga aaacgccgtt tgcggtgatg     300
acctggtttc agccgcagta ccgtaaaacc tttgaccatc cggtcagccg ccagcagctg     360
catgaggtta ttgaccagca aattccttcc gacaatctgt tctgcgcgct gcgaatcgat     420
ggtcatttcc gccacgccca tacccgcacc gtgcctcgtc agacgccgcc ctaccgggcg     480
atgaccgacg tgctcgacga tcagccggtt ttccgcttta accagcgtga cggcgtactg     540
gtcggttttc gtaccccgca gcatatgcag ggaattaacg tcgccggcta tcacgaacac     600
ttcattaccg atgaccgcca gggcggcggc cacctgctgg actaccagct cgaccatggg     660
gtattgacct tcggcgaaat tcataagctg atgatcgacc ttcccgccga cagcgcgttc     720
ctgcaggcca atttgcatcc cgataatctc gatgccgcca tccgttcagt agaaagttag    780

<210> SEQ ID NO 5
<211> LENGTH: 259
<212> TYPE: PRT
<213> ORGANISM: Enterobacter aerogenes

<400> SEQUENCE: 5

Met Asn His Ala Ser Asp Cys Thr Cys Glu Glu Ser Leu Cys Glu Thr
  1               5                  10                  15

Leu Arg Ala Phe Ser Ala Gln His Pro Asp Ser Val Leu Tyr Gln Thr
             20                  25                  30

Ser Leu Met Ser Ala Leu Leu Ser Gly Val Tyr Glu Gly Thr Thr Thr
         35                  40                  45

Ile Ala Asp Leu Leu Lys His Gly Asp Phe Gly Leu Gly Thr Phe Asn
     50                  55                  60

Glu Leu Asp Gly Glu Leu Ile Ala Phe Ser Ser Gln Val Tyr Gln Leu
 65                  70                  75                  80

Arg Ala Asp Gly Ser Ala Arg Lys Ala Arg Pro Glu Gln Lys Thr Pro
                 85                  90                  95

Phe Ala Val Met Thr Trp Phe Gln Pro Gln Tyr Arg Lys Thr Phe Asp
            100                 105                 110

His Pro Val Ser Arg Gln Gln Leu His Glu Val Ile Asp Gln Gln Ile
        115                 120                 125

```
Pro Ser Asp Asn Leu Phe Cys Ala Leu Arg Ile Asp Gly His Phe Arg
        130                 135                 140

His Ala His Thr Arg Thr Val Pro Arg Gln Thr Pro Tyr Arg Ala
145                 150                 155                 160

Met Thr Asp Val Leu Asp Asp Gln Pro Val Phe Arg Phe Asn Gln Arg
                165                 170                 175

Asp Gly Val Leu Val Gly Phe Arg Thr Pro Gln His Met Gln Gly Ile
            180                 185                 190

Asn Val Ala Gly Tyr His Glu His Phe Ile Thr Asp Arg Gln Gly
        195                 200                 205

Gly Gly His Leu Leu Asp Tyr Gln Leu Asp His Gly Val Leu Thr Phe
210                 215                 220

Gly Glu Ile His Lys Leu Met Ile Asp Leu Pro Ala Asp Ser Ala Phe
225                 230                 235                 240

Leu Gln Ala Asn Leu His Pro Asp Asn Leu Asp Ala Ala Ile Arg Ser
                245                 250                 255

Val Glu Ser

<210> SEQ ID NO 6
<211> LENGTH: 678
<212> TYPE: DNA
<213> ORGANISM: Enterobacter cloacae

<400> SEQUENCE: 6
atgagcgccc tgctaagcgg tgtctacgaa ggggacacca ccatcgccga tctgctggca      60
catggtgatt ttggtctggg caccttcaac gagctggacg gcgaaatgat tgccttcagc     120
agccaggtgt accagctgcg cgccgacggc agcgcacgcg ccgcgaagcc agagcagaaa     180
acgccgttcg cggtgatgac ctggttccag ccgcagtacc gcaaaacctt tgatgcgccg     240
gtcagccgtc agcagatcca cgacgtgatc gaccagcaaa ttccctcgga taacctgttc     300
tgcgcgctgc gcatcgacgg caacttccgc cacgcccaca cccgtaccgt accgcgtcag     360
acgccgccat accgcgcgat gaccgacgtg ctggacgacc agccggtgtt ccgctttaac     420
cagcgtgaag gggtgctggt tgggttccgc acgccgcagc atatgcaggg catcaacgtg     480
gccggctatc acgaacattt cattaccgac accgtcaggg cgggggacac tctgctggat     540
taccagctgg agagcggcgt gctcaccttt ggcgaaatac acaagctaat gattgacctg     600
cccgccgaca gcgcgttttt acaggccaac cttcacccca gcaaccttga tgcagcgatc     660
cgttccgtcg aaaactaa                                                  678

<210> SEQ ID NO 7
<211> LENGTH: 225
<212> TYPE: PRT
<213> ORGANISM: Enterobacter cloacae

<400> SEQUENCE: 7

Met Ser Ala Leu Leu Ser Gly Val Tyr Glu Gly Asp Thr Thr Ile Ala
1               5                   10                  15

Asp Leu Leu Ala His Gly Asp Phe Gly Leu Gly Thr Phe Asn Glu Leu
            20                  25                  30

Asp Gly Glu Met Ile Ala Phe Ser Gln Val Tyr Gln Leu Arg Ala
        35                  40                  45
```

```
Asp Gly Ser Ala Arg Ala Ala Lys Pro Glu Gln Lys Thr Pro Phe Ala
    50                  55                  60
Val Met Thr Trp Phe Gln Pro Gln Tyr Arg Lys Thr Phe Asp Ala Pro
65                  70                  75                  80
Val Ser Arg Gln Gln Ile His Asp Val Ile Asp Gln Gln Ile Pro Ser
                85                  90                  95
Asp Asn Leu Phe Cys Ala Leu Arg Ile Asp Gly Asn Phe Arg His Ala
            100                 105                 110
His Thr Arg Thr Val Pro Arg Gln Thr Pro Pro Tyr Arg Ala Met Thr
        115                 120                 125
Asp Val Leu Asp Asp Gln Pro Val Phe Arg Phe Asn Gln Arg Glu Gly
    130                 135                 140
Val Leu Val Gly Phe Arg Thr Pro Gln His Met Gln Gly Ile Asn Val
145                 150                 155                 160
Ala Gly Tyr His Glu His Phe Ile Thr Asp Asp Arg Gln Gly Gly Gly
                165                 170                 175
His Leu Leu Asp Tyr Gln Leu Glu Ser Gly Val Leu Thr Phe Gly Glu
            180                 185                 190
Ile His Lys Leu Met Ile Asp Leu Pro Ala Asp Ser Ala Phe Leu Gln
        195                 200                 205
Ala Asn Leu His Pro Ser Asn Leu Asp Ala Ala Ile Arg Ser Val Glu
    210                 215                 220
Asn
225

<210> SEQ ID NO 8
<211> LENGTH: 762
<212> TYPE: DNA
<213> ORGANISM: Bacillus licheniformis

<400> SEQUENCE: 8
atgaaaagtg caagcaaaca aaaataatt cagcccgttg ataagaaccct cgatcaagtc      60
tatcaggtct caacgatggt atctttattg gacggaattt acgacgggga tttttatatg     120
tccgaagcga aggagcacgg agacttcggg atcgaacgt tcaaccggct cgacggcgag      180
ctgatcggtt tgacggtga gttttaccgt ctccgttccg atggaaaagc ctacccagtt     240
caaggaagcg attgttctcc attttgctcg ctggcttttct tccggccgga tatctatcac   300
gaaatcaagc agcggatgcc gcttgaggcg ttcgaagaag aaatgaaacg gatcatgccg     360
agtgaaaacc tgttttacgc gattcgcatg gacggaacct ttaagaaagt caaaacgaga    420
acagttgaac ttcaggaaaa accgtatgtg ccgatggttg atgcggtaaa atcacagccg     480
atctttgatt taatgatat tacggggacg atcgtcggct tttggacacc gcaatatgcc     540
aacggaatcg cagtttccgg cttccatctt cactttatag atgaagaccg caatgtcggc   600
ggacacgttt tcgattatga aatcgaagaa tgcacggtgc aaatttctca aaaactcaat    660
atgaacctca gattgccgaa tacgcaagat ttctttcaag cggatttcaa taaacacgat   720
cttgcagccg gaattgaagc ggccgaaggc aatcccgagt aa                       762

<210> SEQ ID NO 9
<211> LENGTH: 253
<212> TYPE: PRT
<213> ORGANISM: Bacillus licheniformis
```

<400> SEQUENCE: 9

| | | | | | | | | | | | | | | |
|---|---|---|---|---|---|---|---|---|---|---|---|---|---|---|
|Met|Lys|Ser|Ala|Ser|Lys|Gln|Lys|Ile|Ile|Gln|Pro|Val|Asp|Lys|Asn
1| | | |5| | | | |10| | | | |15|

Leu Asp Gln Val Tyr Gln Val Ser Thr Met Val Ser Leu Leu Asp Gly
    20      25      30

Ile Tyr Asp Gly Asp Phe Tyr Met Ser Glu Ala Lys Glu His Gly Asp
    35      40      45

Phe Gly Ile Gly Thr Phe Asn Arg Leu Asp Gly Glu Leu Ile Gly Phe
 50      55      60

Asp Gly Glu Phe Tyr Arg Leu Arg Ser Asp Gly Lys Ala Tyr Pro Val
65      70      75      80

Gln Gly Ser Asp Cys Ser Pro Phe Cys Ser Leu Ala Phe Phe Arg Pro
     85      90      95

Asp Ile Tyr His Glu Ile Lys Gln Arg Met Pro Leu Glu Ala Phe Glu
    100      105      110

Glu Glu Met Lys Arg Ile Met Pro Ser Glu Asn Leu Phe Tyr Ala Ile
    115      120      125

Arg Met Asp Gly Thr Phe Lys Lys Val Lys Thr Arg Thr Val Glu Leu
130      135      140

Gln Glu Lys Pro Tyr Val Pro Met Val Asp Ala Val Lys Ser Gln Pro
145      150      155      160

Ile Phe Asp Phe Asn Asp Ile Thr Gly Thr Ile Val Gly Phe Trp Thr
    165      170      175

Pro Gln Tyr Ala Asn Gly Ile Ala Val Ser Gly Phe His Leu His Phe
    180      185      190

Ile Asp Glu Asp Arg Asn Val Gly Gly His Val Phe Asp Tyr Glu Ile
    195      200      205

Glu Glu Cys Thr Val Gln Ile Ser Gln Lys Leu Asn Met Asn Leu Arg
    210      215      220

Leu Pro Asn Thr Gln Asp Phe Phe Gln Ala Asp Phe Asn Lys His Asp
225      230      235      240

Leu Ala Ala Gly Ile Glu Ala Ala Glu Gly Asn Pro Glu
    245      250

<210> SEQ ID NO 10
<211> LENGTH: 768
<212> TYPE: DNA
<213> ORGANISM: Bacillus subtilis

<400> SEQUENCE: 10

```
atgaaacgtg agtcgaacat tcaagtcttg agccgaggcc aaaaggacca accagtctcc    60
cagatctacc aagtgagcac tatgacaagt ctcttggacg gagtctacga tggcgatttt   120
gagctctcgg aaattccgaa atatggggat tcggcattg ggacctttaa caaactggac   180
ggtgaactga tcggctttga tggtgagttc taccgcctgc gcagtgatgg gaccgccacg   240
ccggttcaaa atggcgaccg gagcccgttt tgcagcttta cattcttcac ccccgacatg   300
acacacaaga ttgatgctaa atgactcgc gaagatttcg agaagaaat caattcgatg   360
ttgcctagtc gtaatttgtt ttatgccatt cgcatcgacg gtctgtttaa gaaggtgcag   420
acccgcacgg ttgaactcca ggagaagccg tacgttccta tggtggaagc agtcaagacg   480
cagcccatct ttaacttcga caatgtgcgc gggaccattg tcggcttcct gacgcccgct   540
tatgcgaacg gcatcgctgt ctctggttac catctcccact ttatcgatga aggccgaaat   600
tccggaggcc atgttttga ttatgtgctc gaagattgta cggtgaccat cagccagaaa   660
```

```
atgaacatga acttgcggct gccaaatacc gcggatttct tcaatgcaaa cctggataac    720
cccgattttg ccaaagatat tgaaacgact gagggttctc ccgagtag                768
```

<210> SEQ ID NO 11
<211> LENGTH: 255
<212> TYPE: PRT
<213> ORGANISM: Bacillus subtilis

<400> SEQUENCE: 11

```
Met Lys Arg Glu Ser Asn Ile Gln Val Leu Ser Arg Gly Gln Lys Asp
  1               5                  10                  15

Gln Pro Val Ser Gln Ile Tyr Gln Val Ser Thr Met Thr Ser Leu Leu
             20                  25                  30

Asp Gly Val Tyr Asp Gly Asp Phe Glu Leu Ser Glu Ile Pro Lys Tyr
         35                  40                  45

Gly Asp Phe Gly Ile Gly Thr Phe Asn Lys Leu Asp Gly Glu Leu Ile
     50                  55                  60

Gly Phe Asp Gly Glu Phe Tyr Arg Leu Arg Ser Asp Gly Thr Ala Thr
 65                  70                  75                  80

Pro Val Gln Asn Gly Asp Arg Ser Pro Phe Cys Ser Phe Thr Phe Phe
                 85                  90                  95

Thr Pro Asp Met Thr His Lys Ile Asp Ala Lys Met Thr Arg Glu Asp
            100                 105                 110

Phe Glu Lys Glu Ile Asn Ser Met Leu Pro Ser Arg Asn Leu Phe Tyr
        115                 120                 125

Ala Ile Arg Ile Asp Gly Leu Phe Lys Lys Val Gln Thr Arg Thr Val
    130                 135                 140

Glu Leu Gln Glu Lys Pro Tyr Val Pro Met Val Glu Ala Val Lys Thr
145                 150                 155                 160

Gln Pro Ile Phe Asn Phe Asp Asn Val Arg Gly Thr Ile Val Gly Phe
                165                 170                 175

Leu Thr Pro Ala Tyr Ala Asn Gly Ile Ala Val Ser Gly Tyr His Leu
            180                 185                 190

His Phe Ile Asp Glu Gly Arg Asn Ser Gly Gly His Val Phe Asp Tyr
        195                 200                 205

Val Leu Glu Asp Cys Thr Val Thr Ile Ser Gln Lys Met Asn Met Asn
    210                 215                 220

Leu Arg Leu Pro Asn Thr Ala Asp Phe Phe Asn Ala Asn Leu Asp Asn
225                 230                 235                 240

Pro Asp Phe Ala Lys Asp Ile Glu Thr Thr Glu Gly Ser Pro Glu
                245                 250                 255
```

<210> SEQ ID NO 12
<211> LENGTH: 780
<212> TYPE: DNA
<213> ORGANISM: Aeromonas hydrophila

<400> SEQUENCE: 12

```
atggaaacta atagctcgtg cgattgtgca atcgaaatct cgcagcaatt tgcgcgctgg     60
caggcccgtc aaggtggggg cgaggtctac cagtccagcc tgatgtcggc actgctggcg    120
ggtgtttacg aaggcgaaac cacaatggcc gatctgctcc gccacgggga ctttggtctg    180
ggcacgttta accggctgga cggcgaactc attgcctttg agcggcaaat ccatcagttg    240
aaagcggatg gatctgcccg acccgctcgc gcagaacaga aaacgccgtt tgccgtgatg    300
acgcacttcc ggccgtgctt gcaacgccgg ttcgctcatc cgctgtcccg cgaagaaatt    360
```

```
caccaatggg tcgatcgcct cgtgggcact gacaacgttt tcgttgcatt tcgactggat    420
ggcttgtttg agcaagcgca ggtccgcacc gtccctgtc agagcccacc ctataagccc      480
atgttggagg ccattgaagc ccagcctctg ttcagtttca gtttgcggcg tgggacctc     540 gtcggctttc gctgcccacc cttcgtgcaa ggcattaacg tggctggcta tcatgaacat    600
ttcattaccg aggatcgccg aggtgggggt catatcttgg attacgctat gggacacggc    660
cagctccaac tgagcgtggt tcaacaccct aacatcgagt tgcctcgaaa tcctgccttt    720
caacaggcag acctcaatcc ggcggatctg gaccgcgcta tccgtgcggc tgagggttag   780
```

<210> SEQ ID NO 13
<211> LENGTH: 259
<212> TYPE: PRT
<213> ORGANISM: Aeromonas hydrophila

<400> SEQUENCE: 13

```
Met Glu Thr Asn Ser Ser Cys Asp Cys Ala Ile Glu Ile Ser Gln Gln
  1               5                  10                  15

Phe Ala Arg Trp Gln Ala Arg Gln Gly Gly Glu Val Tyr Gln Ser
             20                  25                  30

Ser Leu Met Ser Ala Leu Leu Ala Gly Val Tyr Glu Gly Glu Thr Thr
         35                  40                  45

Met Ala Asp Leu Leu Arg His Gly Asp Phe Gly Leu Gly Thr Phe Asn
     50                  55                  60

Arg Leu Asp Gly Glu Leu Ile Ala Phe Glu Arg Gln Ile His Gln Leu
 65                  70                  75                  80

Lys Ala Asp Gly Ser Ala Arg Pro Ala Arg Ala Glu Gln Lys Thr Pro
                 85                  90                  95

Phe Ala Val Met Thr His Phe Arg Pro Cys Leu Gln Arg Arg Phe Ala
            100                 105                 110

His Pro Leu Ser Arg Glu Glu Ile His Gln Trp Val Asp Arg Leu Val
        115                 120                 125

Gly Thr Asp Asn Val Phe Val Ala Phe Arg Leu Asp Gly Leu Phe Glu
    130                 135                 140

Gln Ala Gln Val Arg Thr Val Pro Cys Gln Ser Pro Pro Tyr Lys Pro
145                 150                 155                 160

Met Leu Glu Ala Ile Glu Ala Gln Pro Leu Phe Ser Phe Ser Leu Arg
                165                 170                 175

Arg Gly Thr Leu Val Gly Phe Arg Cys Pro Pro Phe Val Gln Gly Ile
            180                 185                 190

Asn Val Ala Gly Tyr His Glu His Phe Ile Thr Glu Asp Arg Arg Gly
        195                 200                 205

Gly Gly His Ile Leu Asp Tyr Ala Met Gly His Gly Gln Leu Gln Leu
    210                 215                 220

Ser Val Val Gln His Leu Asn Ile Glu Leu Pro Arg Asn Pro Ala Phe
225                 230                 235                 240

Gln Gln Ala Asp Leu Asn Pro Ala Asp Leu Asp Arg Ala Ile Arg Ala
                245                 250                 255

Ala Glu Gly
```

<210> SEQ ID NO 14
<211> LENGTH: 915
<212> TYPE: DNA
<213> ORGANISM: Acetobacter aceti

<400> SEQUENCE: 14

```
atggaaatag ctttaatat atattggacg tacgaacctg cctgcatcac cattagtctg      60
caatcacaaa tgaccgggtt gaggcgatgc catgtgccgc attgtccccc gatgcaggag    120
actgaggtcg tgaagcttaa atgctactcg gtagggatg ttgatacccg gtccagcgct     180
gctgattcga ctggcgtgcg tccgcgcatg aaccgcctgt accagacatc gaccatggcc    240
gcgctgcttg atgcggtcta tgatggcgag accacgcttg atgaactgct gatgcacggc    300
aatttcgggc tgggcacgtt caacggcctt gatggcgaga tgatcgtcaa tgacagcgta    360
atccaccagt tccgtgcaga cgggcaggcc ggtcgtgtgc cgggcgacct caggactccg    420
ttcgcctgcg ttaccttctt caacccggag aaggaataca tgatcgacac cgcgcaggat    480
aaggaaggct cgaggcgat cgtggatcac ctcgtcaaca atcccaacct gttcgccgcc     540
gtgcgcttta ccggcatgtt cgagcgggtc gagacccgca ccgtgttctg ccagtgccag    600
ccctacccac ccatgctgga agtggtggcc cgccagccca ccatgcagct tggtgcctcc    660
accggcacca tgcttggttt ccgcacgccg ggctacatgc agggcgtgaa cgtggcgggt    720
tatcacctgc acttcctgac tgaggacgga cgccgtggcg ccatgtgac cgattacggc     780
gtgctgcgcg gtcggcttga ggtgggcgtg atttccgatg tggaaatcca gctgccccgc    840
accgaacagt tcgcgcgcgc caacctgtcc ccgaaaaca ttcacgaggc cattcgcgtg     900
gccgagggcg gctga                                                     915
```

<210> SEQ ID NO 15
<211> LENGTH: 304
<212> TYPE: PRT
<213> ORGANISM: Acetobacter aceti

<400> SEQUENCE: 15

```
Met Glu Ile Gly Phe Asn Ile Tyr Trp Thr Tyr Glu Pro Ala Cys Ile
  1               5                  10                  15

Thr Ile Ser Leu Gln Ser Gln Met Thr Gly Leu Arg Arg Cys His Val
             20                  25                  30

Pro His Cys Pro Pro Met Gln Glu Thr Glu Val Val Lys Leu Lys Cys
         35                  40                  45

Tyr Ser Val Gly Asp Val Asp Thr Arg Ser Ser Ala Ala Asp Ser Thr
     50                  55                  60

Gly Val Arg Pro Arg Met Asn Arg Leu Tyr Gln Thr Ser Thr Met Ala
 65                  70                  75                  80

Ala Leu Leu Asp Ala Val Tyr Asp Gly Glu Thr Thr Leu Asp Glu Leu
                 85                  90                  95

Leu Met His Gly Asn Phe Gly Leu Gly Thr Phe Asn Gly Leu Asp Gly
            100                 105                 110

Glu Met Ile Val Asn Asp Ser Val Ile His Gln Phe Arg Ala Asp Gly
        115                 120                 125

Gln Ala Gly Arg Val Pro Gly Asp Leu Arg Thr Pro Phe Ala Cys Val
    130                 135                 140

Thr Phe Phe Asn Pro Glu Lys Glu Tyr Met Ile Asp Thr Ala Gln Asp
145                 150                 155                 160

Lys Glu Gly Phe Glu Ala Ile Val Asp His Leu Val Asn Asn Pro Asn
                165                 170                 175

Leu Phe Ala Ala Val Arg Phe Thr Gly Met Phe Glu Arg Val Glu Thr
            180                 185                 190
```

```
Arg Thr Val Phe Cys Gln Cys Gln Pro Tyr Pro Pro Met Leu Glu Val
            195                 200                 205

Val Ala Arg Gln Pro Thr Met Gln Leu Gly Ala Ser Thr Gly Thr Met
210                 215                 220

Leu Gly Phe Arg Thr Pro Gly Tyr Met Gln Gly Val Asn Val Ala Gly
225                 230                 235                 240

Tyr His Leu His Phe Leu Thr Glu Asp Gly Arg Gly His Val
                245                 250                 255

Thr Asp Tyr Gly Val Leu Arg Gly Arg Leu Glu Val Gly Val Ile Ser
            260                 265                 270

Asp Val Glu Ile Gln Leu Pro Arg Thr Glu Gln Phe Ala Arg Ala Asn
            275                 280                 285

Leu Ser Pro Glu Asn Ile His Glu Ala Ile Arg Val Ala Glu Gly Gly
            290                 295                 300

<210> SEQ ID NO 16
<211> LENGTH: 837
<212> TYPE: DNA
<213> ORGANISM: Candida parapsilosis

<400> SEQUENCE: 16
atgggggaga ttgagtccta ttgtaacaaa gagctaggtc ccttacctac taaagcaccg     60
accctgtcca aaaacgtgct cgatctattc tccttgaagg gaaaggtggc ttcggtgacg    120
ggcagcagcg gaggcattgg ttgggccgta gccgaagcat acgcccaggc cggtgcagac    180
gtcgcgattt ggtacaacag ccatcctgcg gacgagaagg cggaacacct gcagaaaact    240
tatggcgtgc acagtaaagc ctataagtgc aatatcagtg atccgaaaag tgtggaagaa    300
acgatctcac agcaagagaa ggattttggc acgatcgacg tgttcgtcgc taatgccggg    360
gtcacttgga cacagggccc agagatcgat gttgacaact atgattcgtg aacaaaatc    420 attagtgttg atttgaatgg cgtttactat tgcagccaca atattggcaa gatcttcaag    480
aagaatggga aggttctct gattatcacg tcgagtattt ctgggaaaat cgttaacatt    540
ccgcagttgc aagcgcccta caataccgcg aaggccgcgt gtacccatct cgcgaaatcg    600
ctcgccattg aatgggctcc gtttgcacgc gtcaacacga ttagccccgg atacatcgac    660
accgatatca ccgattttgc ctctaaagac atgaaagcta agtggtggca acttactcca    720
ctgggacggg aaggcctcac ccaagaactg gtcggcggct acttgtatct ggctagcaat    780
gcttcgacat ttaccaccgg ttcagatgtc gttatcgatg gcggttacac atgcccc      837

<210> SEQ ID NO 17
<211> LENGTH: 279
<212> TYPE: PRT
<213> ORGANISM: Candida parapsilosis

<400> SEQUENCE: 17

Met Gly Glu Ile Glu Ser Tyr Cys Asn Lys Glu Leu Gly Pro Leu Pro
 1               5                  10                  15

Thr Lys Ala Pro Thr Leu Ser Lys Asn Val Leu Asp Leu Phe Ser Leu
            20                  25                  30

Lys Gly Lys Val Ala Ser Val Thr Gly Ser Ser Gly Gly Ile Gly Trp
        35                  40                  45

Ala Val Ala Glu Ala Tyr Ala Gln Ala Gly Ala Asp Val Ala Ile Trp
    50                  55                  60

Tyr Asn Ser His Pro Ala Asp Glu Lys Ala Glu His Leu Gln Lys Thr
65                  70                  75                  80
```

```
Tyr Gly Val His Ser Lys Ala Tyr Lys Cys Asn Ile Ser Asp Pro Lys
                 85                  90                  95

Ser Val Glu Glu Thr Ile Ser Gln Gln Glu Lys Asp Phe Gly Thr Ile
            100                 105                 110

Asp Val Phe Val Ala Asn Ala Gly Val Thr Trp Thr Gln Gly Pro Glu
        115                 120                 125

Ile Asp Val Asp Asn Tyr Asp Ser Trp Asn Lys Ile Ile Ser Val Asp
    130                 135                 140

Leu Asn Gly Val Tyr Tyr Cys Ser His Asn Ile Gly Lys Ile Phe Lys
145                 150                 155                 160

Lys Asn Gly Lys Gly Ser Leu Ile Ile Thr Ser Ser Ile Ser Gly Lys
                165                 170                 175

Ile Val Asn Ile Pro Gln Leu Gln Ala Pro Tyr Asn Thr Ala Lys Ala
            180                 185                 190

Ala Cys Thr His Leu Ala Lys Ser Leu Ala Ile Glu Trp Ala Pro Phe
        195                 200                 205

Ala Arg Val Asn Thr Ile Ser Pro Gly Tyr Ile Asp Thr Asp Ile Thr
    210                 215                 220

Asp Phe Ala Ser Lys Asp Met Lys Ala Lys Trp Trp Gln Leu Thr Pro
225                 230                 235                 240

Leu Gly Arg Glu Gly Leu Thr Gln Glu Leu Val Gly Tyr Leu Tyr
                245                 250                 255

Leu Ala Ser Asn Ala Ser Thr Phe Thr Thr Gly Ser Asp Val Val Ile
            260                 265                 270

Asp Gly Gly Tyr Thr Cys Pro
        275
```

<210> SEQ ID NO 18
<211> LENGTH: 774
<212> TYPE: DNA
<213> ORGANISM: Leuconostoc pseudomesenteroides

<400> SEQUENCE: 18

```
atgacaaaga aagtggctat ggtgacgggt ggcgcccaag ggatcggaga ggccattgtg        60
cgacgtttgt cggcagatgg ctttgcggtc gcagtggctg atctgaacga agccaaatcc       120
aaggaagtcg ccacggacat cgaaaagaat gggggcactg cgattgcggt taagctcgat       180
gtttcagatc gcgaggggtt tttcgccgct gttaaagaag tcgcggagaa gcttggaggt       240
tttgacgtct tggtaaacaa cgctgggctc ggccccacca cccccatcga tactattacc       300
ccggaactat ttgataaggt ctatcacatc aacgtcgctg cgacatttg ggggattcaa        360
gcagccgtgg agcagttcaa gaaaaatggc aacggcggca aaatcattaa cgcgacaagt       420
caagccggcg tggtcggcaa tcctaatttg tctctgtata gctcgactaa gttcgcagtg       480
cgcggactga cgcaggtcgc agcgcgcgat ctagccgaac agaatatcac ggttaatgcg       540
tacgctccag gaattgtgaa aacgccgatg atgtttgata ttgcccatga agttggcaaa       600
aacgccggta aggatgacga gtggggtatg caaaccttcg cgaaagatat cgctctcaaa       660
cggctgagcg aacccgagga cgtcgccgct gctgttgcgt tcttagcagg tcctgacagt       720
aattacatca ccggtcagac catcgaagtg gatggtggca tgcagtttca ctag            774
```

<210> SEQ ID NO 19
<211> LENGTH: 257
<212> TYPE: PRT
<213> ORGANISM: Leuconostoc pseudomesenteroides

<400> SEQUENCE: 19

```
Met Thr Lys Lys Val Ala Met Val Thr Gly Gly Ala Gln Ile Gly
  1               5                  10                  15
Glu Ala Ile Val Arg Arg Leu Ser Ala Asp Gly Phe Ala Val Ala
                 20                  25                  30
Ala Asp Leu Asn Glu Ala Lys Ser Lys Glu Val Ala Thr Asp Ile Glu
             35                  40                  45
Lys Asn Gly Gly Thr Ala Ile Ala Val Lys Leu Asp Val Ser Asp Arg
 50                  55                  60
Glu Gly Phe Phe Ala Ala Val Lys Glu Val Ala Glu Lys Leu Gly Gly
 65                  70                  75                  80
Phe Asp Val Leu Val Asn Asn Ala Gly Leu Gly Pro Thr Thr Pro Ile
                 85                  90                  95
Asp Thr Ile Thr Pro Glu Leu Phe Asp Lys Val Tyr His Ile Asn Val
                100                 105                 110
Ala Gly Asp Ile Trp Gly Ile Gln Ala Ala Val Glu Gln Phe Lys Lys
            115                 120                 125
Asn Gly Asn Gly Gly Lys Ile Ile Asn Ala Thr Ser Gln Ala Gly Val
130                 135                 140
Val Gly Asn Pro Asn Leu Ser Leu Tyr Ser Ser Thr Lys Phe Ala Val
145                 150                 155                 160
Arg Gly Leu Thr Gln Val Ala Ala Arg Asp Leu Ala Glu Gln Asn Ile
                165                 170                 175
Thr Val Asn Ala Tyr Ala Pro Gly Ile Val Lys Thr Pro Met Met Phe
            180                 185                 190
Asp Ile Ala His Glu Val Gly Lys Asn Ala Gly Lys Asp Asp Glu Trp
            195                 200                 205
Gly Met Gln Thr Phe Ala Lys Asp Ile Ala Leu Lys Arg Leu Ser Glu
            210                 215                 220
Pro Glu Asp Val Ala Ala Ala Val Ala Phe Leu Ala Gly Pro Asp Ser
225                 230                 235                 240
Asn Tyr Ile Thr Gly Gln Thr Ile Glu Val Asp Gly Gly Met Gln Phe
                245                 250                 255
His
```

<210> SEQ ID NO 20
<211> LENGTH: 1056
<212> TYPE: DNA
<213> ORGANISM: Clostridium beijerinckii

<400> SEQUENCE: 20

```
atgaaaggtt ttgccatgct tggaatcaat aagctaggct ggattgaaaa agaacgccca    60
gtggcgggta gttatgatgc catcgttcgc ccactggcag tgtcgccctg tacgagcgat   120
atccacaccg tatttgaggg cgcgttaggg gatcgtaaga atatgattct gggccatgaa   180
gcggttggtg aggtcgtaga ggtggggtct gaagtgaaag atttcaaacc cggcgatcgc   240
gtcatcgttc catgcactac gccggactgg cgaagccttg aagtgcaggc gggattccaa   300
cagcactcaa acggcatgct cgcggggtgg aagttttcca actttaagga cggggtgttc   360
ggggaatact ccacgtcaa cgatgcggat atgaatttag ccattttgcc taaggacatg   420
cccctcgaaa atgctgttat gattaccgat atgatgacaa cgggtttcca cggcgctgag   480
ctcgctgata tccaaatggg cagcagtgtg gttgtcatcg ggattggtgc agtcggcctg   540
atgggcattg cgggagccaa attgcgggga gctggccgca tcattggtgt tggtagccgg   600
```

-continued

```
cctatttgtg tcgaagctgc aaagttttat ggggccacag acattttgaa ctacaagaat    660
ggtcatattg tggaccaggt gatgaagctc acgaatggca agggagtcga tcgcgttatc    720
atggctggcg gtggctctga aaccctgagc caagcagtct cgatggtcaa accgggaggc    780
attatctcga acatcaacta tcatggcagt ggcgatgcgc tgctgatccc ccgagtggag    840
tggggctgcg gcatggccca taagaccatt aaaggcggcc tctgcccggg tggccgtttg    900
cgcgcagaga tgctacgcga tatggtggtc tacaaccggg tggatctgtc caaactggtc    960
actcacgttt accatggttt tgatcacatc gaagaggcct tgttgttgat gaaagacaaa   1020
ccgaaagacc tcattaaagc cgtcgtaatc ctgtag                             1056
```

<210> SEQ ID NO 21
<211> LENGTH: 351
<212> TYPE: PRT
<213> ORGANISM: Clostridium beijerinckii

<400> SEQUENCE: 21

```
Met Lys Gly Phe Ala Met Leu Gly Ile Asn Lys Leu Gly Trp Ile Glu
 1               5                  10                  15

Lys Glu Arg Pro Val Ala Gly Ser Tyr Asp Ala Ile Val Arg Pro Leu
            20                  25                  30

Ala Val Ser Pro Cys Thr Ser Asp Ile His Thr Val Phe Glu Gly Ala
        35                  40                  45

Leu Gly Asp Arg Lys Asn Met Ile Leu Gly His Glu Ala Val Gly Glu
    50                  55                  60

Val Val Glu Val Gly Ser Glu Val Lys Asp Phe Lys Pro Gly Asp Arg
65                  70                  75                  80

Val Ile Val Pro Cys Thr Thr Pro Asp Trp Arg Ser Leu Glu Val Gln
                85                  90                  95

Ala Gly Phe Gln Gln His Ser Asn Gly Met Leu Ala Gly Trp Lys Phe
            100                 105                 110

Ser Asn Phe Lys Asp Gly Val Phe Gly Glu Tyr Phe His Val Asn Asp
        115                 120                 125

Ala Asp Met Asn Leu Ala Ile Leu Pro Lys Asp Met Pro Leu Glu Asn
    130                 135                 140

Ala Val Met Ile Thr Asp Met Met Thr Thr Gly Phe His Gly Ala Glu
145                 150                 155                 160

Leu Ala Asp Ile Gln Met Gly Ser Ser Val Val Ile Gly Ile Gly
                165                 170                 175

Ala Val Gly Leu Met Gly Ile Ala Gly Ala Lys Leu Arg Gly Ala Gly
            180                 185                 190

Arg Ile Ile Gly Val Gly Ser Arg Pro Ile Cys Val Glu Ala Ala Lys
        195                 200                 205

Phe Tyr Gly Ala Thr Asp Ile Leu Asn Tyr Lys Asn Gly His Ile Val
    210                 215                 220

Asp Gln Val Met Lys Leu Thr Asn Gly Lys Gly Val Asp Arg Val Ile
225                 230                 235                 240

Met Ala Gly Gly Gly Ser Glu Thr Leu Ser Gln Ala Val Ser Met Val
                245                 250                 255

Lys Pro Gly Gly Ile Ile Ser Asn Ile Asn Tyr His Gly Ser Gly Asp
            260                 265                 270

Ala Leu Leu Ile Pro Arg Val Glu Trp Gly Cys Gly Met Ala His Lys
        275                 280                 285
```

```
Thr Ile Lys Gly Gly Leu Cys Pro Gly Gly Arg Leu Arg Ala Glu Met
    290                 295                 300

Leu Arg Asp Met Val Val Tyr Asn Arg Val Asp Leu Ser Lys Leu Val
305                 310                 315                 320

Thr His Val Tyr His Gly Phe Asp His Ile Glu Glu Ala Leu Leu Leu
                325                 330                 335

Met Lys Asp Lys Pro Lys Asp Leu Ile Lys Ala Val Val Ile Leu
        340                 345                 350

<210> SEQ ID NO 22
<211> LENGTH: 1056
<212> TYPE: DNA
<213> ORGANISM: Thermoanaerobacter brockii

<400> SEQUENCE: 22
atgaagggtt tcgcaatgct gagcatcggg aaagtcggtt ggatcgaaaa agagaaacct      60
gcgccaggcc cgttcgacgc gattgttcgg cccttagctg tcgcgccgtg cacgtcggac     120
attcacacgg tattcgaagg ggctatcggc gagcggcaca atatgatcct gggccatgaa     180
gctgtcggcg aggttgtcga agtgggctct gaggtgaaag actttaaacc cggcgatcgc     240
gtcgtagttc cggcgatcac tcccgactgg cggacgagtg aagtgcaacg cggctatcac     300
cagcacagcg ggggaatgtt ggcgggctgg aagttttcaa cgtcaagga tggggttttt      360 ggcgaattct ttcatgtgaa cgatgccgat atgaatctgg cccatcttcc taaagagatt     420
ccgctggagg ctgctgtgat gattccggat atgatgacca caggcttcca tggtgctgaa     480
ctcgcggata tcgaactggg tgccaccgtg gcagtgttgg catcggccc tgttggcctc      540 atggcggtcg caggtgctaa gttacgtggg gctggccgta ttatcgccgt cggctcgcgc     600
ccagtgtgtg ttgatgcggc taagtactat ggagccactg atatcgtgaa ctacaaggat     660
ggtcccatcg agagtcagat tatgaatttg accgagggaa agggtgtcga cgccgccatt     720
atcgcaggtg aaacgccga tatcatggcc accgccgtca aaatcgttaa acctggaggt      780
acaattgcaa atgtcaacta ttttggtgaa ggcgaagtgc tgcccgttcc acgcctggaa     840
tggggatgtg ggatggccca taagaccatt aaaggcggcc tctgccccgg tggccgactg     900
cgcatggaac gcctaattga tctcgtgttc tacaaacgag tcgatccgtc aagttggtg      960 acgcacgtgt ttcgcggttt tgacaatatt gagaaggcat ttatgctaat gaaggacaaa    1020
ccgaaagatc tcatcaaacc cgtggtcatt ttggca                              1056

<210> SEQ ID NO 23
<211> LENGTH: 352
<212> TYPE: PRT
<213> ORGANISM: Thermoanaerobacter brockii

<400> SEQUENCE: 23

Met Lys Gly Phe Ala Met Leu Ser Ile Gly Lys Val Gly Trp Ile Glu
1               5                   10                  15

Lys Glu Lys Pro Ala Pro Gly Pro Phe Asp Ala Ile Val Arg Pro Leu
            20                  25                  30

Ala Val Ala Pro Cys Thr Ser Asp Ile His Thr Val Phe Glu Gly Ala
        35                  40                  45

Ile Gly Glu Arg His Asn Met Ile Leu Gly His Glu Ala Val Gly Glu
    50                  55                  60
```

Val Val Glu Val Gly Ser Glu Val Lys Asp Phe Lys Pro Gly Asp Arg
65                  70                  75                  80

Val Val Val Pro Ala Ile Thr Pro Asp Trp Arg Thr Ser Glu Val Gln
                85                  90                  95

Arg Gly Tyr His Gln His Ser Gly Gly Met Leu Ala Gly Trp Lys Phe
            100                 105                 110

Ser Asn Val Lys Asp Gly Val Phe Gly Glu Phe His Val Asn Asp
        115                 120                 125

Ala Asp Met Asn Leu Ala His Leu Pro Lys Glu Ile Pro Leu Glu Ala
    130                 135                 140

Ala Val Met Ile Pro Asp Met Met Thr Thr Gly Phe His Gly Ala Glu
145                 150                 155                 160

Leu Ala Asp Ile Glu Leu Gly Ala Thr Val Ala Val Leu Gly Ile Gly
                165                 170                 175

Pro Val Gly Leu Met Ala Val Ala Gly Ala Lys Leu Arg Gly Ala Gly
            180                 185                 190

Arg Ile Ile Ala Val Gly Ser Arg Pro Val Cys Val Asp Ala Ala Lys
            195                 200                 205

Tyr Tyr Gly Ala Thr Asp Ile Val Asn Tyr Lys Asp Gly Pro Ile Glu
    210                 215                 220

Ser Gln Ile Met Asn Leu Thr Glu Gly Lys Gly Val Asp Ala Ala Ile
225                 230                 235                 240

Ile Ala Gly Gly Asn Ala Asp Ile Met Ala Thr Ala Val Lys Ile Val
                245                 250                 255

Lys Pro Gly Gly Thr Ile Ala Asn Val Asn Tyr Phe Gly Glu Gly Glu
            260                 265                 270

Val Leu Pro Val Pro Arg Leu Glu Trp Gly Cys Gly Met Ala His Lys
            275                 280                 285

Thr Ile Lys Gly Gly Leu Cys Pro Gly Gly Arg Leu Arg Met Glu Arg
290                 295                 300

Leu Ile Asp Leu Val Phe Tyr Lys Arg Val Asp Pro Ser Lys Leu Val
305                 310                 315                 320

Thr His Val Phe Arg Gly Phe Asp Asn Ile Glu Lys Ala Phe Met Leu
                325                 330                 335

Met Lys Asp Lys Pro Lys Asp Leu Ile Lys Pro Val Val Ile Leu Ala
            340                 345                 350

<210> SEQ ID NO 24
<211> LENGTH: 37
<212> TYPE: DNA
<213> ORGANISM: Artificial Sequence
<220> FEATURE:
<223> OTHER INFORMATION: Primer Sequence

<400> SEQUENCE: 24
ctatgacgtc ggcgttttct gctacatggg ccgtgag                         37

<210> SEQ ID NO 25
<211> LENGTH: 37
<212> TYPE: DNA
<213> ORGANISM: Artificial Sequence
<220> FEATURE:
<223> OTHER INFORMATION: Primer Sequence

<400> SEQUENCE: 25
ctaacctagg ggaagtccag cgcaatcagc ggagttg                         37

<210> SEQ ID NO 26
<211> LENGTH: 40
<212> TYPE: DNA
<213> ORGANISM: Artificial Sequence
<220> FEATURE:
<223> OTHER INFORMATION: Primer Sequence

<400> SEQUENCE: 26
ctaaatgcat taagttgtta ctagtgcttg gattctcacc                            40

<210> SEQ ID NO 27
<211> LENGTH: 24
<212> TYPE: DNA
<213> ORGANISM: Artificial Sequence
<220> FEATURE:
<223> OTHER INFORMATION: Primer Sequence

<400> SEQUENCE: 27
ctagagagct ttcgttttca tgag                                            24

<210> SEQ ID NO 28
<211> LENGTH: 30
<212> TYPE: DNA
<213> ORGANISM: Artificial Sequence
<220> FEATURE:
<223> OTHER INFORMATION: Primer Sequence

<400> SEQUENCE: 28
cggggaactc atgaaaacga aagctctcta                                      30

<210> SEQ ID NO 29
<211> LENGTH: 30
<212> TYPE: DNA
<213> ORGANISM: Artificial Sequence
<220> FEATURE:
<223> OTHER INFORMATION: Primer Sequence

<400> SEQUENCE: 29
gttgggtagc agacaatgcg ggggatctgg                                      30

<210> SEQ ID NO 30
<211> LENGTH: 40
<212> TYPE: DNA
<213> ORGANISM: Artificial Sequence
<220> FEATURE:
<223> OTHER INFORMATION: Primer Sequence

<400> SEQUENCE: 30
ggttttgcac caggatcccg ctcgagttga cgcgtgctta                           40

<210> SEQ ID NO 31
<211> LENGTH: 20
<212> TYPE: DNA
<213> ORGANISM: Artificial Sequence
<220> FEATURE:
<223> OTHER INFORMATION: Primer Sequence

<400> SEQUENCE: 31
tcactgcccg ctttccagtc                                                 20

<210> SEQ ID NO 32
<211> LENGTH: 40
<212> TYPE: DNA
<213> ORGANISM: Artificial Sequence
<220> FEATURE:
<223> OTHER INFORMATION: Primer Sequence

```
<400> SEQUENCE: 32
agttgacgcg tgcttatcat aattgtgagc ggataacaat                           40

<210> SEQ ID NO 33
<211> LENGTH: 24
<212> TYPE: DNA
<213> ORGANISM: Artificial Sequence
<220> FEATURE:
<223> OTHER INFORMATION: Primer Sequence

<400> SEQUENCE: 33
ctagagagct ttcgttttca tgag                                           24

<210> SEQ ID NO 34
<211> LENGTH: 36
<212> TYPE: DNA
<213> ORGANISM: Artificial Sequence
<220> FEATURE:
<223> OTHER INFORMATION: Primer Sequence

<400> SEQUENCE: 34
taggtcgacg aggaatcacc atgaatcatg cttcag                              36

<210> SEQ ID NO 35
<211> LENGTH: 40
<212> TYPE: DNA
<213> ORGANISM: Artificial Sequence
<220> FEATURE:
<223> OTHER INFORMATION: Primer Sequence

<400> SEQUENCE: 35
aggtcgactc tagaggatct ctaactttct actgaacgga                          40

<210> SEQ ID NO 36
<211> LENGTH: 36
<212> TYPE: DNA
<213> ORGANISM: Artificial Sequence
<220> FEATURE:
<223> OTHER INFORMATION: Primer Sequence

<400> SEQUENCE: 36
taggtcgacg aggaatcacc atgagcgccc tgctaa                              36

<210> SEQ ID NO 37
<211> LENGTH: 36
<212> TYPE: DNA
<213> ORGANISM: Artificial Sequence
<220> FEATURE:
<223> OTHER INFORMATION: Primer Sequence

<400> SEQUENCE: 37
caggtcgact ctagaggatc tttagttttc gacgga                              36

<210> SEQ ID NO 38
<211> LENGTH: 36
<212> TYPE: DNA
<213> ORGANISM: Artificial Sequence
<220> FEATURE:
<223> OTHER INFORMATION: Primer Sequence

<400> SEQUENCE: 38
taggtcgacg aggaatcacc atggaaatag gcttta                              36
```

<210> SEQ ID NO 39
<211> LENGTH: 36
<212> TYPE: DNA
<213> ORGANISM: Artificial Sequence
<220> FEATURE:
<223> OTHER INFORMATION: Primer Sequence

<400> SEQUENCE: 39
caggtcgact ctagaggatc ttcagccgcc ctcggc                             36

<210> SEQ ID NO 40
<211> LENGTH: 35
<212> TYPE: DNA
<213> ORGANISM: Artificial Sequence
<220> FEATURE:
<223> OTHER INFORMATION: Primer Sequence

<400> SEQUENCE: 40
ctaggtcgac gaggaatcac catgaaaagt gcaag                              35

<210> SEQ ID NO 41
<211> LENGTH: 37
<212> TYPE: DNA
<213> ORGANISM: Artificial Sequence
<220> FEATURE:
<223> OTHER INFORMATION: Primer Sequence

<400> SEQUENCE: 41
caggtcgact ctagaggatc tttactcggg attgcct                            37

<210> SEQ ID NO 42
<211> LENGTH: 35
<212> TYPE: DNA
<213> ORGANISM: Artificial Sequence
<220> FEATURE:
<223> OTHER INFORMATION: Primer Sequence

<400> SEQUENCE: 42
taggtcgacg aggaatcacc atgaaacgtg agtcg                              35

<210> SEQ ID NO 43
<211> LENGTH: 36
<212> TYPE: DNA
<213> ORGANISM: Artificial Sequence
<220> FEATURE:
<223> OTHER INFORMATION: Primer Sequence

<400> SEQUENCE: 43
caggtcgact ctagaggatc tctactcggg agaacc                             36

<210> SEQ ID NO 44
<211> LENGTH: 35
<212> TYPE: DNA
<213> ORGANISM: Artificial Sequence
<220> FEATURE:
<223> OTHER INFORMATION: Primer Sequence

<400> SEQUENCE: 44
taggtcgacg aggaatcacc atggaaacta atagc                              35

<210> SEQ ID NO 45
<211> LENGTH: 36
<212> TYPE: DNA
<213> ORGANISM: Artificial Sequence
<220> FEATURE:
<223> OTHER INFORMATION: Primer Sequence

<400> SEQUENCE: 45
caggtcgact ctagaggatc tctaaccctc agccgc                          36

<210> SEQ ID NO 46
<211> LENGTH: 30
<212> TYPE: DNA
<213> ORGANISM: Artificial Sequence
<220> FEATURE:
<223> OTHER INFORMATION: Primer Sequence

<400> SEQUENCE: 46
cgggatcctg gtgcaaaacc tttcgcggta                                 30

<210> SEQ ID NO 47
<211> LENGTH: 40
<212> TYPE: DNA
<213> ORGANISM: Artificial Sequence
<220> FEATURE:
<223> OTHER INFORMATION: Primer Sequence

<400> SEQUENCE: 47
gtacctttct cctcttctaa ctttctactg aacggatggc                      40

<210> SEQ ID NO 48
<211> LENGTH: 35
<212> TYPE: DNA
<213> ORGANISM: Artificial Sequence
<220> FEATURE:
<223> OTHER INFORMATION: Primer Sequence

<400> SEQUENCE: 48
tagaagagga gaaaggtaca tgaaaggttt tgcca                           35

<210> SEQ ID NO 49
<211> LENGTH: 36
<212> TYPE: DNA
<213> ORGANISM: Artificial Sequence
<220> FEATURE:
<223> OTHER INFORMATION: Primer Sequence

<400> SEQUENCE: 49
caggtcgact ctagaggatc tctacaggat tacgac                          36

<210> SEQ ID NO 50
<211> LENGTH: 35
<212> TYPE: DNA
<213> ORGANISM: Artificial Sequence
<220> FEATURE:
<223> OTHER INFORMATION: Primer Sequence

<400> SEQUENCE: 50
gttagaagag gagaaaggta catgaagggt ttcgc                           35

<210> SEQ ID NO 51
<211> LENGTH: 36
<212> TYPE: DNA
<213> ORGANISM: Artificial Sequence
<220> FEATURE:
<223> OTHER INFORMATION: Primer Sequence

<400> SEQUENCE: 51
caggtcgact ctagaggatc tctatgccaa aatgac                          36

```
<210> SEQ ID NO 52
<211> LENGTH: 35
<212> TYPE: DNA
<213> ORGANISM: Artificial Sequence
<220> FEATURE:
<223> OTHER INFORMATION: Primer Sequence

<400> SEQUENCE: 52
ttagaagagg agaaaggtac atgggggaga ttgag                              35

<210> SEQ ID NO 53
<211> LENGTH: 37
<212> TYPE: DNA
<213> ORGANISM: Artificial Sequence
<220> FEATURE:
<223> OTHER INFORMATION: Primer Sequence

<400> SEQUENCE: 53
caggtcgact ctagaggatc tctaggggca tgtgtaa                            37

<210> SEQ ID NO 54
<211> LENGTH: 34
<212> TYPE: DNA
<213> ORGANISM: Artificial Sequence
<220> FEATURE:
<223> OTHER INFORMATION: Primer Sequence

<400> SEQUENCE: 54
ttagaagagg agaaaggtac atgacaaaga aagt                               34

<210> SEQ ID NO 55
<211> LENGTH: 36
<212> TYPE: DNA
<213> ORGANISM: Artificial Sequence
<220> FEATURE:
<223> OTHER INFORMATION: Primer Sequence

<400> SEQUENCE: 55
aggtcgactc tagaggatct ctagtgaaac tgcatg                             36

<210> SEQ ID NO 56
<211> LENGTH: 39
<212> TYPE: DNA
<213> ORGANISM: Artificial Sequence
<220> FEATURE:
<223> OTHER INFORMATION: Primer Sequence

<400> SEQUENCE: 56
ggtcgactct agaggatctt gtacctttct cctctttaa                          39

<210> SEQ ID NO 57
<211> LENGTH: 40
<212> TYPE: DNA
<213> ORGANISM: Artificial Sequence
<220> FEATURE:
<223> OTHER INFORMATION: Primer Sequence

<400> SEQUENCE: 57
gtacctttct cctcttctaa ccctcagccg cacggatagc                         40

<210> SEQ ID NO 58
<211> LENGTH: 21
<212> TYPE: DNA
<213> ORGANISM: Artificial Sequence
<220> FEATURE:
<223> OTHER INFORMATION: Primer Sequence
```

```
<400> SEQUENCE: 58
agatcctcta gagtcgacct g                                                 21
```

METHODS OF PRODUCING ACETOIN AND 2,3-BUTANEDIOL USING PHOTOSYNTHETIC MICROORGANISMS

CROSS-REFERENCE TO RELATED APPLICATION(S)

The present application is a U.S. National Phase of PCT/US2013/062459, filed Sep. 28, 2013, which claims priority from U.S. Provisional Application No. 61/707,866, filed Sep. 28, 2012, each of which is incorporated herein by reference in its entirety for all purposes.

SUBMISSION OF SEQUENCE LISTING ON ASCII TEXT FILE

The content of the following submission on ASCII text file is incorporated herein by reference in its entirety: a computer readable form (CRF) of the Sequence Listing (file name:514112006300Seq.List.txt, date recorded: Mar. 26, 2015, size: 48 KB).

FIELD

The present disclosure provides recombinant cyanobacteria having acetolactate synthase activity and acetolactate decarboxylase activity, as well as recombinant cyanobacteria having acetolactate synthase activity, acetolactate decarboxylase activity, and secondary alcohol dehydrogenase activity. Methods for the production of the recombinant cyanobacteria, as well as for use thereof for production of acetoin and 2,3-butanediol from carbon dioxide and light are also provided.

BACKGROUND

Amid rising global energy demands, interest is growing in the production of fuels and chemicals from renewable resources. Petroleum consumption reached 37.1 quadrillion BTU in the United States in 2008, of which a large majority (71%) was liquid fuel in the transportation sector. Petroleum and natural gas account for 99% of the feedstocks for chemicals such as plastics, fertilizers and pharmaceuticals in chemical industry (McFarlane et al.,"Survey of Alternative Feedstocks for Commodity Chemical Manufacturing." Oak Ridge National Laboratory, 2007). Considering rapidly increasing world population and exhaustion of fossil fuels, the development of sustainable processes for energy and carbon capture (ECC) to produce fuels and chemicals is crucial for the human society.

In addition to increasing energy demands, renewable energy resources are of interest to address growing environmental issues. According to the United States Energy Information Administration (Serferlein, "Annual Energy Review, USEIA 2008), world energy-related $CO_2$ emissions in 2006 were 29 billion metric tons, which is an increase of 35% from 1990. Accelerating accumulation of atmospheric $CO_2$ is not only due to increased emissions from world growth and intensifying carbon use, but also from a possible attenuation in the efficiency of the world's natural carbon sinks (Raupach et al., *Proc Natl Acad Sci USA*, 104:10288-10293, 2007). As a result, atmospheric levels of $CO_2$ have increased by ~25% over the past 150 years. Thus, it has become increasingly important to develop new technologies to reduce $CO_2$ emissions.

Previous methods of producing renewable energies have involved converting terrestrial plant biomass into biochemicals. However, these methods present undesirable complications, such as harsh chemical pretreatments of the biomass resulting in toxic byproducts and large land-use requirements to grow the plants. Photosynthetic microorganisms possess many advantages over traditional terrestrial plants with regard to biochemical production. For example, the photosynthetic efficiency of photosynthetic microorganisms is higher than plants, and photosynthetic microorganisms can be cultivated in locations that do not compete with traditional agricultural crops (Scharlemann et al., *Science*, 281:237-240, 2008).

An example of a photosynthetic microorganism with potential for biochemical production is cyanobacteria. Cyanobacteria are collectively responsible for almost 50% of global photosynthesis and are found in a wide range of environments (Field et al., *Science*, 281:237-240, 1998). While cyanobacteria have many similar features with algae in this context, many cyanobacterial species feature simpler genetic structures and faster growth rates (Ruffing, *Bioeng Bugs*, 2:136-149, 2011). As a result, genetic engineering methods for cyanobacteria are also more advanced in terms of genetic manipulation efforts than those for algae (Golden et al., *Methods Enzymol*, 153:215-231, 1987; Huang et al., *Nucleic Acids Res*, 38:2577-2593, 2010; and Heidorn et al., *Methods Enzymol*, 497:539-579, 2011).

Cyanobacteria have the biochemical machinery required to fix $CO_2$, but lack the critical components to generate fuels and chemicals efficiently. Thus to produce valuable chemicals, cyanobacteria host strains must be equipped with new biosynthetic pathways (Keasling, *ACS Chem Biol*, 3:64-76, 2008; Ducat et al., *Trends Biotechnol*, 29:95-103, 2011; and Machado and Atsumi, *J Biotechnol*, 2012). Unfortunately, this approach in cyanobacteria is significantly less developed compared to a model organism such as *Escherichia coli*. Further, results in *E. coli* cannot be directly translated into cyanobacteria. For example, an engineered *E. coli* strain containing the 1-butanol pathway produced more than 30 g/L 1-butanol (Shen et al., *Appl Environ Microbiol*, 77:2905-2915, 2011), while a cyanobacterial strain with the same pathway produced only trace amounts of 1-butanol (Lan et al., *Metab Eng*, 13:353-363, 2011). Thus, there exists a need for construction of a biosynthetic pathway in cyanobacteria leading to significant production of a commodity chemical from $CO_2$.

BRIEF SUMMARY

The present disclosure provides recombinant cyanobacteria having acetolactate synthase activity and acetolactate decarboxylase activity, as well as recombinant cyanobacteria having acetolactate synthase activity, acetolactate decarboxylase activity, and secondary alcohol dehydrogenase activity. Methods for the production the recombinant cyanobacteria, as well as methods for use thereof for production of acetoin and 2,3-butanediol from carbon dioxide and light are also provided.

The present disclosure provides cyanobacteria comprising a recombinant (e.g., heterologous) polynucleotide encoding an acetolactate synthase (ALS) and an acetolactate decarboxylase (ALDC), wherein expression of the ALS and the ALDC results in an increase in production of acetoin as compared to a corresponding cyanobacterium lacking the polynucleotide. The present disclosure further provides cyanobacteria comprising a recombinant (e.g., heterologous) polynucleotide encoding an acetolactate synthase (ALS), an acetolactate decarboxylase (ALDC) and a secondary alcohol dehydrogenase (sADH), wherein expression of the ALS, the ALDC and the sADH results in an increase in production of one or both of acetoin and 2,3-butanediol (23BD) as compared to a corresponding cyanobacterium lacking the polynucleotide. In some embodiments, the corresponding cyanobacterium is a control cyanobacterium such as a parent cyanobacterium or a cell of the same genus, or the same species. In some embodiments, the ALS is a bacterial ALS. In some preferred embodiments, the ALS is a *Bacillus* sp. ALS (e.g., a *Bacillus subtilis* ALS). In some embodiments, the ALDC is a bacterial ALDC or a fungal ALDC. In some preferred embodiments, the ALDC is selected from the group consisting of an *Enterobacter* sp. ALDC, a *Bacillus* sp. ALDC, an *Aeromonas* sp. ALDC, and a *Gluconacetobacter* sp. ALDC. In a subset of these embodiments, the ALDC is selected from the group consisting of an *Enterobacter aerogenes* ALDC, an *Enterobacter cloacae* ALDC, a *Bacillus licheniformis* ALDC, a *Bacillus subtilis* ALDC, an *Aeromonas hydrophila* ALDC, and a *Gluconacetobacter xylinus* ALDC. In some embodiments, the sADH is a bacterial sADH or a fungal sADH. In some embodiments, the sADH is selected from the group consisting of an ascomycetes sADH, a firmicutes sADH and a saccharomycetes sADH. In some preferred embodiments, the sADH is selected from the group consisting of a *Candida* sp. sADH, a *Leuconostoc* sp. sADH, a *Clostridium* sp. sADH, and a *Thermoanaerobacter* sp. sADH. In a subset of these embodiments, the sADH is selected from the group consisting of a *Candida parapsilosis* sADH, a *Leuconostoc pseudomesenteroides* sADH, a *Clostridium beijerinckii* sADH, and a *Thermoanaerobacter brockii* sADH. In some embodiments, the expression of the ALS and the ALDC, or the expression of the ALS, the ALDC and the sADH is driven by an inducible promoter. In some embodiments, the expression of the ALS and the ALDC, or the expression of the ALS, the ALDC and the sADH is driven by a constitutive promoter. In some embodiments, the polynucleotide is stably integrated into the genome of the cyanobacterium. In some embodiments, the polynucleotide is transiently maintained (e.g., as a plasmid) within the cyanobacterium. In some embodiments, the cyanobacterium is of an order selected from the group consisting of chroococcales and nostocales. In some preferred embodiments, the cyanobacterium is selected from the group consisting of *Nostoc* sp., *Synechococcus* sp., *Synechocystis* sp., and *Thermosynechococcus* sp. In a subset of these embodiments, the cyanobacterium is selected from the group consisting of *Nostoc punctiforme* ACCS 074, *Synechococcus elongates* PCC 7942, *Synechococcus* sp. WH 8102, *Synechocystis* sp. PCC 6803, and *Thermosynechococcus elongates* BP-1. In some embodiments, the production of one or both of acetoin and 2,3-butanediol (23BD) occurs as a result of culturing the cyanobacterium under constant light. In some embodiments, the production of one or both of acetoin and 2,3-butanediol (23BD) occurs as a result of culturing the cyanobacterium in the presence of bicarbonate. In some embodiments, wherein the ALDC is essentially insensitive to oxygen (undetectable or low oxygen sensitivity). In some embodiments, the sADH is essentially insensitive to oxygen (undetectable or low oxygen sensitivity) and is NADPH-dependent.

Additionally, the present disclosure provides methods of producing acetoin, comprising: providing a cyanobacterium; and culturing the cyanobacterium in a photosynthetic environment comprising $CO_2$ and light whereby the expression of the ALS and the ALDC results in production of acetoin. In some embodiments, the production of acetoin occurs at a higher level than that produced by culturing the corresponding (e.g., control) cyanobacterium lacking the polynucleotide under the same conditions. The present disclosure further provides methods of producing 2,3-butanediol, comprising: providing a cyanobacterium; and culturing the cyanobacterium in a photosynthetic environment comprising $CO_2$ and light whereby expression of the ALS, the ALDC and the sADH results in production of 2,3-butanediol (23BD). In some embodiments, the production of 23BD occurs at a higher level than that produced by culturing the corresponding (e.g., control) cyanobacterium lacking the polynucleotide under the same conditions. The cyanobacterium that produces one or both of acetoin and 23BD through the use of these methods is a cyanobacterium of the preceding paragraph or a recombinant cyanobacterium as otherwise provided in the description of the present disclosure.

BRIEF DESCRIPTION OF THE DRAWINGS

FIG. 5A shows time courses for growth. FIG. 5B shows total 23BD production. FIG. 5C shows photosynthetic efficiency. FIG. 5D shows total biomass production per day. Error bars indicate standard deviation (n=3).

DESCRIPTION

Figure 1:
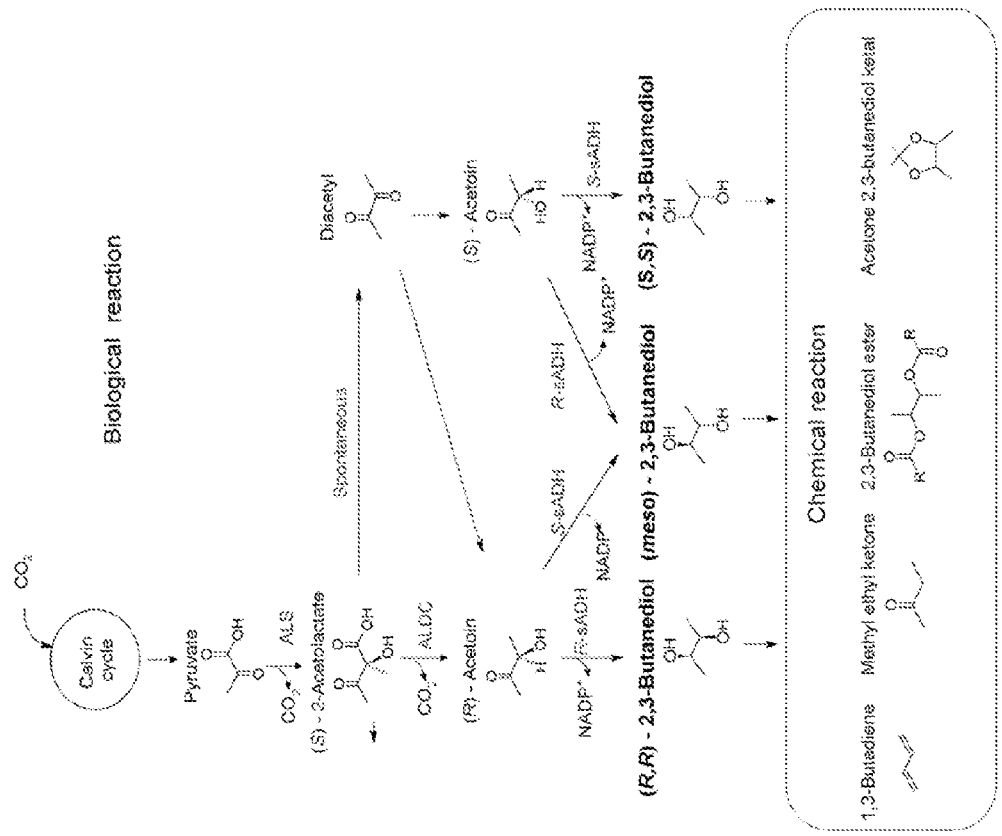
FIG. 1 illustrates how $CO_2$ can be used in the biological synthesis of acetoin and 2,3-butanediol, as well as other industrially important chemicals. ALS: acetolactate synthase, ALDC: acetolactate decarboxylase, sADH: secondary alcohol dehydrogenase.

There exists a need to curb $CO_2$ emissions into the atmosphere and/or reduce the $CO_2$ concentrations already in the atmosphere. Photosynthetic microorganisms have the capability of removing this compound from the atmosphere, but generally lack the capability to synthesize commodity chemicals using $CO_2$ as a starting material. A useful commodity chemical is the compound acetoin. Acetoin is cited as one of the top 30 most valuable chemical building blocks suitable for use by biorefineries (U.S. Department of Energy). Additionally, acetoin is a widely used perfuming agent and flavorant with important applications in the food industry. Prior to development of the present disclosure, there were no known methods for producing acetoin from $CO_2$ nor were there any known methods for producing acetoin from $CO_2$ and sun light with the use of photosynthetic microorganisms.

Another useful commodity chemical is 2,3-butanediol (23BD); a versatile building block molecule for the synthesis of valuable chemicals. 23BD can be converted by dehydrogenation to methyl ethyl ketone (MEK), which is a liquid fuel additive and useful industrial solvent (Tran et al., *Biotechnol Bioeng*, 29:343-351, 1987). Furthermore, the catalytic conversion of 23BD to 1,3-butadiene, which is a precursor for a diversity of polymer and copolymer materials, has been well established (van Haveren et al., *Biofuels Bioprod Bioref*, 2:41-57, 2008). 23BD has also been used in the manufacturing of plasticizers, inks, fumigants, and explosives (Syu, *Appl Microbiol Biotechnol*, 55:10-18, 2001). Importantly, 23BD can be synthesized from the starting compound acetoin. While microbial fermentation of 23BD has also been developed for many years (Ji et al., *Biotechnol Adv*, 29:351-364, 2011; and Celinska and Grajek, *Biotechnol Adv*, 27:715-725, 2009), existing methods fail to additionally address the need to reduce $CO_2$ emissions from the atmosphere.

Conversion of $CO_2$ by photosynthetic organisms is an attractive target for establishment of fossil fuel reserve-independent synthesis of chemicals. As described herein, a 2,3-butanediol (23BD) biosynthetic pathway has been systematically developed in *Synechococcus elongatus* PCC7942. This model system demonstrates that cyanobacteria can be employed for efficient production of commodity chemicals. 23BD was selected as a target chemical with low host toxicity, which permitted the design of an oxygen-insensitive, cofactor-matched biosynthetic pathway coupled with irreversible enzymatic steps to create a driving force toward 23BD production. Exemplary methods resulted in the production of 23BD from $CO_2$ to a level of 2.38 g/L, which is a significant increase for chemical production from exogenous pathways in cyanobacteria.

Recombinant Polynucleotides, Vectors, Source, and Host Organisms

The present disclosure provides cyanobacteria for use in the production of acetoin and 2,3-butanediol (23BD). These cyanobacteria contain a recombinant polynucleotide encoding an acetolactate synthase (ALS) and an acetolactate decarboxylase (ALDC). Expression of the ALS and ALDC results in an increase in production of acetoin as compared to a cyanobacterium lacking this polynucleotide.

The present disclosure further provides cyanobacteria for use in the production acetoin and/or 2,3-butanediol. These cyanobacteria contain a recombinant polynucleotide encoding and acetolactate synthase (ALS), an acetolactate decarboxylase (ALDC), and a secondary alcohol dehydrogenase (sADH). Expression of the ALS, ALDC, and sADH results in an increase in production of acetoin and/or 2,3-butanediol as compared to a cyanobacterium lacking this polynucleotide.

Also provided herein are recombinant vectors, expression cassettes, and polynucleotides comprising coding sequences of one or more of ALS, ALDC, and sADH. In some embodiments, these nucleic acids are used to produce bacteria (e.g., cyanobacteria), which in turn can be used to produce one or both of acetoin and 2,3-butanediol.

Provided herein are polynucleotides comprising coding sequences for an acetolactate synthase and an acetolactate decarboxylase. Also provided herein are polynucleotides comprising coding sequences for an acetolactate synthase, an acetolactate decarboxylase, and a secondary alcohol dehydrogenase. In some embodiments, the coding sequences are operably linked to a promoter as part of a vector or an expression cassette.

As used herein, "vector" refers to a polynucleotide compound and/or composition that once introduced into a host cell, transforms a host cell, thereby causing the cell to express polynucleotides and/or polypeptides other than those native to the organism, or in a manner not native to the organism. Preferred vectors are plasmids or similar genetic constructs, particularly those with restriction sites that have been well documented to ease the cloning step of introducing polynucleotide sequences of interest into the plasmid. Such plasmids, as well as other vectors, are well known to those of ordinary skill in the art and may be used in the compositions and methods of the present disclosure as appropriate.

As used herein, "coding sequence" refers to a polynucleotide sequence that, when expressed, can be translated into a polypeptide.

As used herein, "operably linked" refers to a configuration in which a control sequence is placed at an appropriate position relative to the coding sequence of the polynucleotide sequence such that the control sequence directs expression of the polynucleotide.

In preferred embodiments, the acetolactate synthase coding sequence of the present disclosure corresponds to an alsS polynucleotide or a homolog thereof. In preferred embodiments, the acetolactate decarboxylase coding sequence corresponds to an alsD polynucleotide or a homolog thereof. In preferred embodiments, the secondary alcohol dehydrogenase coding sequence corresponds to an adh polynucleotide or a homolog thereof.

In preferred embodiments, the alsS polynucleotide produces a polypeptide having acetolactate synthase activity. In preferred embodiments, the alsD polynucleotide produces a polypeptide having acetolactate decarboxylase activity. In preferred embodiments, the adh polynucleotide produces a polypeptide having secondary alcohol dehydrogenase activity.

Acetolactate synthase (ALS) is part of an amino acid biosynthesis pathway responsible for the synthesis of valine, leucine, and isoleucine. Overall, acetolactate synthase enzymes catalyze the conversion of two pyruvate molecules into 2-acetolacate and $CO_2$. Specifically, the enzyme catalyzes the aldo condensation of two molecules of pyruvate to 2-acetolactate. The overall reaction catalyzed by ALS is irreversible because of $CO_2$ evolution. The first step in catalysis is the ionization of the thiazolium ring of thiamine pyrophosphate (TPP). Overall, TPP is involved in the linkage of the two pyruvate molecules. The highly reactive tricyclic intermediate first forms and this reacts with the first pyruvate that then decarboxylates to give the relatively non-reactive enamine. Because this intermediate is stable, the enzyme can pause midway through the catalytic cycle while releasing $CO_2$ and admitting the second molecule of pyruvate. The tricyclic-carbanion then forms, followed by reacting with the second pyruvate. Deprotonation followed by carbon-carbon bond breakage completes the reaction, producing 2-acetolactate (see, e.g. US 2011/0262982).

Enzymatic reactions can be classified according to their Enzyme Commission (EC) number. The EC number associated with a given enzyme specifies the classification of the type of enzymatic reaction that a given enzyme is capable of catalyzing. EC numbers do not specify identities of enzymes, but instead specify the identity of the chemical reaction that a given enzyme catalyzes. Similarly, proteins can also be assigned Gene Ontology (GO) terms. GO terms attempt to further define the given role and/or function of a protein in a living organism by specifying protein function in terms of a cellular component, a biological process, and/or a molecular function. For example, two enzymes from two different species of organisms that catalyze the same chemical reaction could be assigned the same EC classification and GO term annotation, despite that the respective enzymes are endogenous to different organisms. EC and GO term classifications are helpful to those skilled in the art in identifying the molecular function and/or activity of a given protein outside of knowing its unique identifying classification with regard to the organism it came from, such as its NCBI (National Council for Biotechnology) identifier.

Acetolactate synthase enzymes catalyze the enzymatic reaction belonging to the classification EC 2.2.1.6 (acetolactate synthase activity) and gene ontology (GO) term ID of GO: 0003984. The GO term ID specifies that any protein characterized as having this associated GO term encodes an enzyme with catalytic acetolactate synthase activity.

Various acetolactate synthase (alsS) genes, which encode acetolactate synthase enzymes, are known in the art. Examples of alsS genes include but are not limited to gi|83644996|ref|YP_433431.1| acetolactate synthase [*Hahella chejuensis* KCTC 2396]; gi|32141318|ref|NP_733719.1| acetolactate synthase [*Streptomyces coelicolor* A3(2)]; gi|238917299|ref|YP_002930816.1| acetolactate synthase [*Eubacterium eligens* ATCC 27750]; gi|312136848|ref|YP_004004185.1| acetolactate synthase [*Methanothermus fervidus* DSM 2088]; gi|311224567|gb|ADP77423.1| Acetolactate synthase [*Methanothermus fervidus* DSM 2088]; gi|238872659|gb|ACR72369.1| acetolactate synthase [*Eubacterium eligens* ATCC 27750]; gi|19671178|emb|CAL95091.1| acetolactate synthase [*Azo-*
*arcus* sp. BH72]; gi|384250777|gb|EIE24256.1| acetolactate synthase [*Coccomyxa subellipsoidea* C-169]; gi|365857129|ref|ZP_09397126.1| acetolactate synthase [*Acetobacteraceae bacterium* AT-5844]; gi|363716653|gb|EHM00051.1| acetolactate synthase [*Acetobacteraceae bacterium* AT-5844]; gi|357547224|gb|EHJ29116.1| acetolactate synthase [*Lactobacillus rhamnosus* ATCC 21052]; gi|312898921|ref|ZP_07758309.1| acetolactate synthase [*Megasphaera micronuciformis* F0359]; gi|310620083|gb|EFQ03655.1| acetolactate synthase [*Megasphaera micronuciformis* F0359]; gi|392978028|ref|YP_006476616.1| acetolactate synthase [*Enterobacter cloacae* subsp. *dissolvens* SDM]; gi|387878229|ref|YP_006308533.1| acetolactate synthase [*Mycobacterium* sp. MOTT36Y]; gi|387619850|ref|YP_006127477.1| acetolactate synthase [*Escherichia coli* DH1]; gi|386760231|ref|YP_006233448.1| acetolactate synthase [*Bacillus* sp. JS]; gi|386732742|ref|YP_006206238.1| acetolactate synthase [*Listeria monocytogenes* 07PF0776]; gi|386035198|ref|YP_005955111.1| acetolactate synthase [*Klebsiella pneumoniae* KCTC 2242]; gi|384259770|YP_005403704.1| acetolactate synthase [*Rahnella aquatilis* HX2]; gi|384267136|ref|YP_005422843.1| acetolactate synthase [*Bacillus amyloliquefaciens* subsp. *plantarum* YAU B9601-Y2]; gi|384170312|ref|YP_005551690.1| acetolactate synthase [*Bacillus amyloliquefaciens* XH7]; gi|379741437|ref|YP_005333406.1| acetolactate synthase [*Vibrio cholerae* IEC224]; gi|375364038|ref|YP_005132077.1| acetolactate synthase [*Bacillus amyloliquefaciens* subsp. *plantarum* CAU B946]; gi|375261263|ref|YP_005020433.1| acetolactate synthase [*Klebsiella oxytoca* KCTC 1686]; gi|375009759|ref|YP_004983392.1| acetolactate synthase [*Geobacillus thermoleovorans* CCB_US3_UF5]; gi|374323653|ref|YP_005076782.1| acetolactate synthase [*Paenibacillus terrae* HPL-003]; gi|344207293|ref|YP_004792434.1| acetolactate synthase [*Stenotrophomonas maltophilia* JV3]; gi|338534039|ref|YP_004667373.1| acetolactate synthase [*Myxococcus fulvus* HW-1]; gi|336249979|ref|YP_004593689.1| acetolactate synthase [*Enterobacter aerogenes* KCTC 2190]; gi|334144738|ref|YP_004537894.1| acetolactate synthase [*Thioalkalimicrobium cyclicum* ALM1]; gi|333895383|ref|YP_004469258.1| acetolactate synthase [*Alteromonas* sp. SN2]; gi|332297456|ref|YP_004439378.1| Acetolactate synthase [*Treponema brennaborense* DSM 12168]; gi|330838389|ref|YP_004412969.1| Acetolactate synthase [*Selenomonas sputigena* ATCC 35185]; gi|328950467|ref|YP_004367802.1| acetolactate synthase [*Marinithermus hydrothermalis* DSM 14884]; gi|326780667|ref|ZP_08239932.1| Acetolactate synthase [*Streptomyces griseus* XylebKG-1]; gi|325298954|ref|YP_004258871.1| Acetolactate synthase [*Bacteroides salanitronis* DSM 18170]; gi|321313145|ref|YP_004205432.1| acetolactate synthase [*Bacillus subtilis*BSn5]; gi|311070109|ref|YP_003975032.1| acetolactate synthase [*Bacillus atrophaeus* 1942]; gi|53721452|ref|YP_110437.1| acetolactate synthase [*Burkholderia pseudomallei* K96243]; gi|21221221|ref|NP_627000.1| acetolactate synthase

[*Streptomyces coelicolor*A3(2)]. Each sequence associated with the foregoing accession numbers is incorporated herein by reference.

Acetolactate decarboxylase (ALDC) is an enzyme that belongs to the family of carboxy lyases, which are responsible for cleaving carbon-carbon bonds. Acetolactate decarboxylase catalyzes the conversion of 2-acetolactate (also known as 2-hydroxy-2-methyl-3-oxobutanoate) to 2-acetoin and releasing $CO_2$.

Acetolactate decarboxylase enzymes catalyze the enzymatic reaction belonging to the classification EC 4.1.1.5 (acetolactate decarboxylase activity) and gene ontology (GO) term ID of GO: 0047605. The GO term ID specifies that any protein characterized as having this associated GO term encodes an enzyme with catalytic acetolactate decarboxylase activity.

Various acetolactate decarboxylase (alsD) genes, which encode acetolactate decarboxylase enzymes, are known in the art. Examples of alsD genes include but are not limited to gi|375143627|ref|YP_005006068.1| Acetolactate decarboxylase [*Niastella koreensis* GR20-10]; gi|361057673|gb|AEV96664.1| Acetolactate decarboxylase [*Niastella koreensis* GR20-10]; gi|218763415|gb|ACL05881.1| Acetolactate decarboxylase [*Desulfatibacillum alkenivorans* AK-01]; gi|220909520|ref|YP_002484831.1| acetolactate decarboxylase [*Cyanothece* sp. PCC 7425]; gi|218782031|ref|YP_002433349.1| acetolactate decarboxylase [*Desulfatibacillum alkenivorans* AK-01]; gi|213693090|ref|YP_002323676.1| Acetolactate decarboxylase [*Bifidobacterium longum* subsp. *infantis*ATCC 15697 =JCM 1222]; gi|189500297|ref|YP_001959767.1| Acetolactate decarboxylase [*Chlorobium phaeobacteroides* BS1]; gi|189423787|ref|YP_001950964.1| acetolactate decarboxylase [*Geobacter lovleyi* SZ]; gi|172058271|ref|YP_001814731.1| acetolactate decarboxylase [*Exiguobacterium sibiricum* 255-15]; gi|163938775|ref|YP_001643659.1| acetolactate decarboxylase [*Bacillus weihenstephanensis* KBAB4]; gi|158522304|ref|YP_001530174.1| acetolactate decarboxylase [*Desulfococcus oleovorans* Hxd3]; gi|57371670|ref|YP_001479659.1| acetolactate decarboxylase [*Serratia proteamaculans* 568]; gi|150395111|ref|YP_001317786.1| acetolactate decarboxylase [*Staphylococcus aureus* subsp. *aureus* JH1]; gi|150394715|ref|YP_001317390.1| acetolactate decarboxylase [*Staphylococcus aureus* subsp. *aureus* JH1]; gi|146311679|ref|YP_001176753.1| acetolactate decarboxylase [*Enterobacter* sp. 638]; gi|109900061|ref|YP_663316.1| acetolactate decarboxylase [*Pseudoalteromonas atlantica* T6c]; gi|219866131|gb|ACL46470.1| Acetolactate decarboxylase [*Cyanothece* sp. PCC 7425]; gi|213524551|gb|ACJ53298.1| Acetolactate decarboxylase [*Bifidobacterium longum* subsp. *infantis* ATCC 15697=JCM 1222]; gi|189420046|gb|IACD94444.1| Acetolactate decarboxylase [*Geobacter lovleyi* SZ]; gi|158511130|gb|ABW68097.1| Acetolactate decarboxylase [*Desulfococcus oleovorans* Hxd3]; gi|157323434|gb|ABV42531.1| Acetolactate decarboxylase [*Serratia proteamaculans* 568]; gi|145318555|gb|ABP60702.1| Acetolactate decarboxylase [*Enterobacter* sp. 638]; gi|149947563|gb|ABR53499.1| Acetolactate decarboxylase [*Staphylococcus aureus* subsp. *aureus* JH1]; gi|149947167|gb|ABR53103.1 | Acetolactate decarboxylase [*Staphylococcus aureus* subsp. *aureus*JH1]; l gi|163860972|gb|ABY42031.1| Acetolactate decarboxylase [*Bacillus weihenstephanensis* KBAB4]; gi|109702342|gb|ABG42262.1| Acetolactate decarboxylase [*Pseudoalteromonas atlantica* T6c]; gi|189495738|gb|ACE04286.1| Acetolactate decarboxylase [*Chlorobium phaeobacteroides* BS1]; gi|171990792|gb|ACB61714.1| Acetolactate decarboxylase [*Exiguobacterium sibiricum* 255-15]; gi|223932563|ref|ZP_03624564.1| Acetolactate decarboxylase [*Streptococcus suis* 89/1591]; gi|194467531|ref|ZP_03073518.1| Acetolactate decarboxylase [*Lactobacillus reuteri* 100-23]; gi|223898834|gb|EEF65194.1| Acetolactate decarboxylase [*Streptococcus suis* 89/1591]; gi|194454567|gb|EDX43464.1| Acetolactate decarboxylase [*Lactobacillus reuteri* 100-23]; gi|384267135|ref|YP_005422842.1| acetolactate decarboxylase [*Bacillus amyloliquefaciens* subsp. *plantarum* YAU B9601-Y2]; gi|375364037|ref|YP_005132076.1| acetolactate decarboxylase [*Bacillus amyloliquefaciens* subsp. *plantarum* CAU B946]; gi|34079323|ref|YP_004758694.1| acetolactate decarboxylase [*Corynebacterium variabile* DSM 44702]; gi|336325119|ref|YP_004605085.1| acetolactate decarboxylase [*Corynebacterium resistens* DSM 45100]; gi|148269032|ref|YP_001247975.1| acetolactate decarboxylase [*Staphylococcus aureus* subsp. *aureus JH9*]; gi|148268650|ref|YP_001247593.1| acetolactate decarboxylase [*Staphylococcus aureus* subsp. *aureus* JH9]; gi|148543372|ref|YP_001270742.1| acetolactate decarboxylase [*Lactobacillus reuteri* DSM 20016]; gi|380500488|emb|CCG51526.1| acetolactate decarboxylase [*Bacillus amyloliquefaciens* subsp. *plantarum YAU B9601-Y2*]; gi|371570031|emb|CCF06881.1| acetolactate decarboxylase [*Bacillus amyloliquefaciens* subsp. *plantarum* CAU B946]; gi|340533141|gb|AEK35621.1| acetolactate decarboxylase [*Corynebacterium variabile* DSM 44702]; gi|336101101|gb|AE108921.1| acetolactate decarboxylase [*Corynebacterium resistens* DSM 45100]; gi|148530406|gb|ABQ82405.1| Acetolactate decarboxylase [*Lactobacillus reuteri* DSM 20016]; gi|147742101|gb|ABQ50399.1| Acetolactate decarboxylase [*Staphylococcus aureus* subsp. *aureus* JH9]; gi|147741719|gb|ABQ50017.1| Acetolactate decarboxylase [*Staphylococcus aureus* subsp. *aureus* JH9]; gi|392529510|ref|ZP_10276647.1| acetolactate decarboxylase [*Carnobacterium maltaromaticum* ATCC 35586]; gi|366054074|ZP_09451796.1| acetolactate decarboxylase [*Lactobacillus suebicus* KCTC 3549]; gi|339624147|ref|ZP_08659936.1| acetolactate decarboxylase [*Fructobacillus fructosus* KCTC 3544]; gi|336393727|ref|ZP_08575126.1| acetolactate decarboxylase [*Lactobacillus coryniformis* subsp. *torquens* KCTC 3535]. Each sequence associated with the foregoing accession numbers is incorporated herein by reference.

Alcohol dehydrogenase (ADH) is an enzyme that catalyzes the reduction of aldehydes and/or ketones into alcohols. Secondary alcohol dehydrogenases specifically have catalytic activity on substrates capable of producing secondary alcohols. Secondary alcohols are those alcohols in which the carbon bound to the hydroxyl (alcohol) functional group is covalently bonded to two other carbon atoms. Depending on the specific ADH, some alcohol dehydrogenases can also catalyze the opposite reaction, catalyzing the oxidation of alcohols into aldehydes and/or ketones. Alcohol dehydrogenases typically use NAD-containing molecules (such as NAP+, NADH, and NADPH) as cofactors in the enzymatic redox reaction with their substrates. With regard to the methods of the present disclosure, the secondary alcohol dehydrogenase catalyzes the reduction of an aldehyde and/or ketone into an alcohol.

Alcohol dehydrogenase enzymes catalyze the enzymatic reaction belonging to the classification EC 1.1.1.1 (alcohol dehydrogenase activity) and gene ontology (GO) term ID of GO: 0004025. The GO term ID specifies that any protein characterized as having this associated GO term encodes an enzyme with catalytic alcohol dehydrogenase activity.

Various alcohol dehydrogenase (adh) genes, which encode alcohol dehydrogenase enzymes, are known in the art. Examples of adh genes include but are not limited to gi|223587866|emb|CAX36647.1| alcohol dehydrogenase [*Arthrobacter* sp. JEK-2009]; gi|343083017|ref|YP_004772312.1| alcohol dehydrogenase [*Cyclobacterium marinum* DSM 745]; gi|375146863|ref|YP_005009304.1| Alcohol dehydrogenase [*Niastella koreensis* GR20 10]; gi|332296134|ref|YP_004438057.1| Alcohol dehydrogenase [*Thermodesulfobium narugense* DSM 14796]; gi|327403757|ref|YP_004344595.1| Alcohol dehydrogenase (NADP(+)) [*Fluviicola taffensis* DSM 16823]; gi|325287739|ref|YP_004263529.1| alcohol dehydrogenase [*Cellulophaga lyticab* DSM 7489]; gi|325295143|ref|YP_004281657.1| Alcohol dehydrogenase [*Desulfurobacterium thermolithotrophum* DSM 11699]; gi|325289753|ref|YP_004265934.1| alcohol dehydrogenase [*Syntrophobotulus glycolicus* DSM 8271]; gi|325289499|ref|YP_004265680.1| alcohol dehydrogenase [*Syntrophobotulus glycolicus* DSM 8271]; gi|325110410|ref|YP_004271478.1| alcohol dehydrogenase [*Planctomyces brasiliensis* DSM 5305]; gi|325108594|ref|YP_004269662.1| alcohol dehydrogenase [*Planctomyces brasiliensis* DSM 5305]; gi|1319955560|ref|YP_004166827.1| alcohol dehydrogenase [*Cellulophaga algicola* DSM 14237]; gi|325065591|gb|ADY73598.1| Alcohol dehydrogenase [*Desulfurobacterium thermolithotrophum* DSM 11699]; gi|332179237|gb|AEE14926.1| Alcohol dehydrogenase [*Thermodesulfobium narugense* DSM 14796]; gi|324970678|gb|ADY61456.1| Alcohol dehydrogenase [*Planctomyces brasiliensis* DSM 5305]; gi|324968862|gb|ADY59640.1| Alcohol dehydrogenase [*Planctomyces brasiliensis* DSM 5305]; gi|324965154|gb|ADY55933.1| Alcohol dehydrogenase [*Syntrophobotulus glycolicus* DSM 8271]; gi|324964900|gb|ADY55679.1| Alcohol dehydrogenase [*Syntrophobotulus glycolicus* DSM 8271]; gi|374373821|ref|ZP_09631481.1|Alcohol dehydrogenase [*Niabella soli* DSM 19437]; gi|373234794|gb|EHP54587.1| Alcohol dehydrogenase [*Niabella soli* DSM 19437]; gi|361060909|gb|AEV99900.1| Alcohol dehydrogenase [*Niastella koreensis*GR20-10]; gi|375144658|ref|YP_005007099.1| alcohol dehydrogenase [*Niastella koreensis* GR20-10]; gi|332981006|ref|YP_004462447.1| alcohol dehydrogenase zinc-binding domain-containing protein [*Mahella australiensis* 50-1 BON]; gi|332666040|ref|YP_004448828.1| alcohol dehydrogenase [*Haliscomenobacter hydrossis* DSM 1100]; gi|330837587|ref|YP_004412228.1| alcohol dehydrogenase [*Sphaerochaeta coccoides* DSM 17374]; gi|330837463|ref|YP_004412104.1| alcohol dehydrogenase [*Sphaerochaeta coccoides* DSM 17374]; gi|330836315|ref|YP_004410956.1| alcohol dehydrogenase [*Sphaerochaeta coccoides* DSM 17374]; gi|327405514|ref|YP_004346352.1| Alcohol dehydrogenase zinc-binding domain-containing protein [*Fluviicola taffensis* DSM 16823]; gi|325298359|ref|YP_004258276.1| Alcohol dehydrogenase [*Bacteroides salanitronis* DSM 18170]; gi|325291396|ref|YP_004267577.1| alcohol dehydrogenase [*Syntrophobotulus glycolicus* DSM 8271]; gi|325281283|ref|YP_004253825.1| Alcohol dehydrogenase (NADP(+)) [*Odoribacter splanchnicus* DSM 20712]; gi|325299524|ref|YP_004259441.1| Alcohol dehydrogenase [*Bacteroides salanitronis* DSM 18170]; gi|325106236|YP_004275890.1| alcohol dehydrogenase [*Pedobacter saltans* DSM 12145]; gi|320333315|ref|YP_004170026.1| alcohol dehydrogenase [*Deinococcus maricopensis* DSM 21211]; gi|329749366|gb|AEC2722.1| Alcohol dehydrogenase [*Sphaerochaeta coccoides* DSM 17374]; gi|324319077|ADY36968.1| Alcohol dehydrogenase [*Bacteroides salanitronis* DSM 18170]; gi|324317912|ADY35803.1| Alcohol dehydrogenase [*Bacteroides salanitronis* DSM 18170]; gi|384129895|YP_005512508.1| alcohol dehydrogenase [*Hydrogenobacter thermophilus* TK-6]; gi|357419011|ref|YP_004932003.1| alcohol dehydrogenase [*Thermovirga lienii* DSM 17291]; gi|332981068|ref|YP_004462509.1| alcohol dehydrogenase zinc-binding domain-containing protein [*Mahella australiensis* 50-1 BON]; gi|330837556|YP_004412197.1| alcohol dehydrogenase [*Sphaerochaeta coccoides* DSM 17374]; gi|330836856|ref|YP_004411497.1| alcohol dehydrogenase [*Sphaerochaeta coccoides* DSM 17374]; gi|327398952|ref|YP_004339821.1| Alcohol dehydrogenase [*Hippea maritima* DSM 10411]; gi|325290821|ref|YP_004267002.1| alcohol dehydrogenase [*Syntrophobotulus glycolicus* DSM 8271]; gi|322833567|ref|YP_004213594.1| alcohol dehydrogenase [*Rahnella* sp. Y9602]; gi|308049202|ref|YP_003912768.1| alcohol dehydrogenase [*Ferrimonas balearica* DSM 9799]; gi|302392706|ref|YP_003828526.1| alcohol dehydrogenase [*Acetohalobium arabaticum* DSM 5501]; gi|302336054|YP_003801261.1| alcohol dehydrogenase [*Olsenella uli* DSM 7084]; gi|302335092|ref|YP_003800299.1| alcohol dehydrogenase [*Olsenella uli* DSM 7084]; gi|152966730|ref|YP_001362514.1| alcohol dehydrogenase [*Kineococcus radiotolerans* SRS30216]. Each sequence associated with the foregoing accession numbers is incorporated herein by reference.

In preferred embodiments, the acetolactate decarboxylase polypeptide is insensitive to oxygen. In this embodiment, the acetolactate decarboxylase would have enzyme activity on its substrates even in the absence of oxygen in the environment. In some embodiments, the secondary alcohol dehydrogenase is essentially insensitive to oxygen. In this embodiment, the secondary alcohol dehydrogenase would have enzyme activity on its substrates even in the absence of oxygen in the environment.

In some embodiments, the secondary alcohol dehydrogenase polypeptide requires NADPH as a cofactor. This means that the secondary alcohol dehydrogenase (sADH) is NADPH-dependent.

In some embodiments, the secondary alcohol dehydrogenase polypeptide induces S-installing chirality on its substrates. In some embodiments, the secondary alcohol dehydrogenase polypeptide induces R-installing chirality on its substrates.

As used herein, "chiral" refers to a molecular compound that is not superimposable on its mirror image. The molecule and its mirror image are thus referred to in terms of their "chirality," often referred to as S or R. Different enzymes have the capacity to induce an S configuration on its substrate to form an S-product or to induce an R configuration on its substrate to form an R-product. If a given molecule has more than one asymmetric carbon, then different enzymes can induce multiple S and R configurations on the different asymmetric carbons in the target molecule.

The present disclosure identifies specific polynucleotides/genes useful in the methods, compositions and organisms of the disclosure. However, it should be recognized that absolute identity to such genes is not necessary, as substantially similar polynucleotides/genes that perform substantially similar functions can also be used in the compositions and methods of the present disclosure. For example, changes in a particular gene or polynucleotide containing a sequence encoding a polypeptide or enzyme can be performed and screened for activity. Typically such changes include conservative mutation and silent mutations. Such modified or mutated polynucleotides and polypeptides can be screened for expression or function of enzymes using methods known in the art. Additionally, homologs of the polynucleotides/genes of the present disclosure are suitable for use in the compositions and methods disclosed herein.

Due to the inherent degeneracy of the genetic code, polynucleotides which encode substantially the same or a functionally equivalent polypeptide can also be used to clone and express the same polypeptides or enzymes. As will be understood by those of skill in the art, it can be advantageous to modify a coding sequence to enhance its expression in a particular host. The genetic code is redundant with 64 possible codons, but most organisms typically use a subset of these codons. The codons that are utilized most often in a species are called optimal codons, and those not utilized very often are classified as rare or low-usage codons. Codons can be substituted to reflect the preferred codon usage of *E. coli* or *S. elongatus*, a process sometimes called "codon optimization" or "controlling for species codon bias" (See Murray et al. 1989 Nucl. Acids Res. 17:477-508). An example of codon optimization of a polynucleotide is present in Example 1 of the present disclosure (also see Table 4).

Those of skill in the art will recognize that, due to the degenerate nature of the genetic code, a variety of DNA compounds differing in their nucleotide sequences can be used to encode a given polypeptide or enzyme of the disclosure. The present disclosure includes DNA compounds of any sequence that encode the amino acid sequences of the polypeptides and proteins of the enzymes utilized in the compositions and methods of the disclosure. In similar fashion, a polypeptide can typically tolerate one or more amino acid substitutions, deletions, and insertions in its amino acid sequence without loss or significant loss of a desired activity.

Homologs of polypeptides or enzymes useful for generating metabolites are encompassed by the microorganisms and methods provided herein. The term "homologs" used with respect to an original enzyme or gene of a first family or species refers to distinct enzymes or genes of a second family or species which are determined by functional, structural or genomic analyses to be an enzyme or gene of the second family or species which corresponds to the original enzyme or gene of the first family or species. Most often, homologs will have functional, structural or genomic similarities. Techniques are known by which homologs of an enzyme or gene can readily be cloned using genetic probes and PCR. Homologs can be identified by reference to various databases and identity of cloned sequences as homolog can be confirmed using functional assays and/or by genomic mapping of the genes.

A protein has "homology" or is "homologous" to a second protein if the nucleic acid sequence that encodes the protein has a similar sequence to the nucleic acid sequence that encodes the second protein. Alternatively, a protein has homology to a second protein if the two proteins have "similar" amino acid sequences. Thus, the term "homologous proteins" is defined to mean that the two proteins have similar amino acid sequences.

As used herein, two proteins (or a region of the proteins) are substantially homologous when the amino acid sequences have at least about 30%, 40%, 50% 60%, 65%, 70%, 75%, 80%, 85%, 90%, 91%, 92%, 93%, 94%, 95%, 96%, 97%, 98%, or 99% identity. Similarly, two polynucleotides (or a region of the polynucleotides) are substantially homologous when the nucleic acid sequences have at least about 30%, 40%, 50% 60%, 65%, 70%, 75%, 80%, 85%, 90%, 91%, 92%, 93%, 94%, 95%, 96%, 97%, 98%, or 99% identity . To determine the percent identity of two amino acid sequences, or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

In some embodiments of the disclosure, the coding sequences of the polynucleotides are operably linked to a promoter. In some embodiments, the promoter is an inducible promoter. In some embodiments, the promoter is a constitutive promoter.

As used herein, "inducible promoter" refers to a promoter that drives expression of a polynucleotide to which it is operably linked upon cellular perception of a stimulus. Likewise, inducible promoters can terminate expression of a polynucleotide to which it is operably linked upon removal of a stimulus. An example of an inducible promoter in the present disclosure is the isopropyl-β-D-thiogalactoside (IPTG) inducible promoter, in which this promoter drives expression of a polynucleotide to which it is operably linked upon perception of IPTG, an exogenous chemical. Any appropriate inducible promoter that has use in the compositions and methods of the present disclosure may be used accordingly. One of skill in the art will recognize that many characterized inducible promoters exist and can be used according to the compositions and methods disclosed herein.

Constitutive promoters are those promoters that are substantially insensitive to regulation by external stimuli and promote expression of a given polynucleotide in an essentially constant manner.

The present disclosure provides recombinant vectors containing recombinant polynucleotides for use in host microorganisms such as cyanobacteria.

As used herein, "recombinant" or "heterologous" or "heterologous polynucleotide" or "recombinant polynucleotide" refers to a polynucleotide wherein the exact nucleotide sequence of the polynucleotide is foreign to (i.e., not naturally found in) a given host. These terms may also refer to a polynucleotide sequence that may be naturally found in a given host, but in an unnatural (e.g., greater than or less than expected) amount, or additionally if the sequence of a polynucleotide comprises two or more subsequences that are not found in the same relationship to each other in nature. For example, regarding the latter, a recombinant polynucleotide could have two or more sequences from unrelated polynucleotides or from homologous nucleotides arranged to make a new polynucleotide. Specifically, the present disclosure describes the introduction of a recombinant vector into a microorganism, wherein the vector contains a polynucleotide coding for a polypeptide that is not normally found in the microorganism or contains a foreign polynucleotide coding for a substantially homologous polypeptide that is normally found in the host organism. With reference to the host cell's genome, then, the polynucleotide sequence that encodes the polypeptide is recombinant or heterologous.

In some embodiments, the recombinant polynucleotides of the present disclosure are stably integrated into the genome of the host organism. In some embodiments, the host organism is a cyanobacterium that has had the recombinant polynucleotides of the present disclosure stably integrated into its genome. As used herein, "stably integrated," as used with reference to the stable integration of a recombinant polynucleotide into a genome, refers to the phenomenon where the recombinant polynucleotide has become physically integrated into the organism's genomic DNA such that mitotic and reproductive events that require genomic DNA replication pass on the genetic information contained in the recombinant polynucleotide as a physical unit of the host genome.

In other embodiments, the recombinant polynucleotides of the present disclosure are not stably integrated in the host organism such as a cyanobacterium. In this sense, the recombinant polynucleotide is expressed in a host cell without becoming stably integrated into the host genome.

In some embodiments, the recombinant vector or expression cassette includes coding sequences for an acetolactate synthase and an acetolactate decarboxylase operably linked to a promoter. In preferred embodiments, the acetolactate synthase coding sequence of the present disclosure corresponds to an alsS polynucleotide or a homolog thereof. In preferred embodiments, the acetolactate decarboxylase coding sequence corresponds to an alsD polynucleotide or a homolog thereof.

It should be noted that with regard to recombinant molecules, the polynucleotides and coding sequences are always associated with their respective polypeptides. An acetolactate synthase alsS polynucleotide will produce an ALS polypeptide. An acetolactate decarboxylase alsD polynucleotide will produce an ALDC polypeptide. A secondary alcohol dehydrogenase adh polynucleotide will produce a sADH polypeptide. By definition, a polynucleotide or coding sequence from a given organism also implies the respective polypeptide is from the given organism.

In preferred embodiments, the alsS polynucleotide is derived from *Bacillus subtilis*. In some embodiments, the alsD polynucleotide is derived from a source organism selected from *Enterobacter aerogenes, Enterobacter cloacae, Bacillus licheniformis, Bacillus subtilis, Aeromonas hydrophila*, and *Gluconacetobacter xylinus*.

In some embodiments, the recombinant polynucleotide contains an alsS polynucleotide from *Bacillus subtilis* and an alsD polynucleotide from *Enterobacter aerogenes*. In some embodiments, the recombinant vector contains an alsS polynucleotide from *Bacillus subtilis* and an alsD polynucleotide from *Enterobacter cloacae*. In some embodiments, the recombinant polynucleotide contains an alsS polynucleotide from *Bacillus subtilis* and an alsD polynucleotide from *Bacillus licheniformis*. In some embodiments, the recombinant polynucleotide contains an alsS polynucleotide from *Bacillus subtilis* and an alsD polynucleotide from *Bacillus subtilis*. In some embodiments, the recombinant polynucleotide contains an alsS polynucleotide from *Bacillus subtilis* and an alsD polynucleotide from *Aeromonas hydrophila*. In some embodiments, the recombinant polynucleotide contains an alsS polynucleotide from *Bacillus subtilis* and an alsD polynucleotide from *Gluconacetobacter xylinus*.

In some embodiments, the recombinant polynucleotide includes coding sequences for an acetolactate synthase, an acetolactate decarboxylase, and a secondary alcohol dehydrogenase. In preferred embodiments, the acetolactate synthase coding sequence corresponds to an alsS polynucleotide or a homolog thereof. In preferred embodiments, the acetolactate decarboxylase coding sequence corresponds to an alsD polynucleotide or a homolog thereof. In preferred embodiments, the secondary alcohol dehydrogenase coding sequence corresponds to an adh polynucleotide or a homolog thereof.

In preferred embodiments, the alsS polynucleotide is derived from *Bacillus subtilis*. In some embodiments, the alsD polynucleotide is derived from a source organism selected from *Enterobacter aerogenes, Enterobacter cloacae, Bacillus licheniformis, Bacillus subtilis, Aeromonas hydrophila*, and *Gluconacetobacter xylinus*. In some embodiments, the adh polynucleotide is derived from a source organism selected from *Candida parapsilosis, Leuconostoc pseudomesenteroides, Clostridium beijerinckii*, and *Thermoanaerobacter brockii*.

In some embodiments, the recombinant polynucleotide contains an alsS polynucleotide from *Bacillus subtilis*, an alsD polynucleotide from *Enterobacter aerogenes*, and an adh polynucleotide from *Candida parapsilosis*. In some embodiments, the recombinant polynucleotide contains an alsS polynucleotide from *Bacillus subtilis*, an alsD polynucleotide from *Enterobacter aerogenes*, and an adh polynucleotide from *Leuconostoc pseudomesenteroides*. In some embodiments, the recombinant polynucleotide contains an alsS polynucleotide from *Bacillus subtilis*, an alsD polynucleotide from *Enterobacter aerogenes*, and an adh polynucleotide from *Clostridium beijerinckii*. In some embodiments, the recombinant polynucleotide contains an alsS polynucleotide from *Bacillus subtilis*, an alsD polynucleotide from *Enterobacter aerogenes*, and an adh polynucleotide from *Thermoanaerobacter brockii*.

In some embodiments, the recombinant polynucleotide contains an alsS polynucleotide from *Bacillus subtilis*, an alsD polynucleotide from *Enterobacter cloacae*, and an adh polynucleotide from *Candida parapsilosis*. In some embodiments, the recombinant polynucleotide contains an alsS polynucleotide from *Bacillus subtilis*, an alsD polynucleotide from *Enterobacter cloacae*, and an adh polynucleotide from *Leuconostoc pseudomesenteroides*. In some embodiments, the recombinant polynucleotide contains an alsS polynucleotide from *Bacillus subtilis*, an alsD polynucleotide from *Enterobacter cloacae*, and an adh polynucleotide from *Clostridium beijerinckii*. In some embodiments, the recombinant polynucleotide contains an alsS polynucleotide from *Bacillus subtilis*, an alsD polynucleotide from *Enterobacter cloacae*, and an adh polynucleotide from *Thermoanaerobacter brockii*.

In some embodiments, the recombinant polynucleotide contains an alsS polynucleotide from *Bacillus subtilis*, an alsD polynucleotide from *Bacillus licheniformis*, and an adh polynucleotide from *Candida parapsilosis*. In some embodiments, the recombinant polynucleotide contains an alsS polynucleotide from *Bacillus subtilis*, an alsD polynucleotide from *Bacillus licheniformis*, and an adh polynucleotide from *Leuconostoc pseudomesenteroides*. In some embodiments, the recombinant polynucleotide contains an alsS polynucleotide from *Bacillus subtilis*, an alsD polynucleotide from *Bacillus licheniformis*, and an adh polynucleotide from *Clostridium beijerinckii*. In some embodiments, the recombinant polynucleotide contains an alsS polynucleotide from *Bacillus subtilis*, an alsD polynucleotide from *Bacillus licheniformis*, and an adh polynucleotide from *Thermoanaerobacter brockii*.

In some embodiments, the recombinant polynucleotide contains an alsS polynucleotide from *Bacillus subtilis*, an alsD polynucleotide from *Bacillus subtilis*, and an adh polynucleotide from *Candida parapsilosis*. In some embodiments, the recombinant polynucleotide contains an alsS polynucleotide from *Bacillus subtilis*, an alsD polynucleotide from *Bacillus subtilis*, and an adh polynucleotide from *Leuconostoc pseudomesenteroides*. In some embodiments, the recombinant polynucleotide contains an alsS polynucleotide from *Bacillus subtilis*, an alsD polynucleotide from *Bacillus subtilis*, and an adh polynucleotide from *Clostridium beijerinckii*. In some embodiments, the recombinant polynucleotide contains an alsS polynucleotide from *Bacillus subtilis*, an alsD polynucleotide from *Bacillus subtilis*, and an adh polynucleotide from *Thermoanaerobacter brockii*.

In some embodiments, the recombinant polynucleotide contains an alsS polynucleotide from *Bacillus subtilis*, an alsD polynucleotide from *Aeromonas hydrophila*, and an adh polynucleotide from *Candida parapsilosis*. In some embodiments, the recombinant polynucleotide contains an alsS polynucleotide from *Bacillus subtilis*, an alsD polynucleotide from *Aeromonas hydrophila*, and an adh polynucleotide from *Leuconostoc pseudomesenteroides*. In some embodiments, the recombinant polynucleotide contains an alsS polynucleotide from *Bacillus subtilis*, an alsD polynucleotide from *Aeromonas hydrophila*, and an adh polynucleotide from *Clostridium beijerinckii*. In some embodiments, the recombinant polynucleotide contains an alsS polynucleotide from *Bacillus subtilis*, an alsD polynucleotide from *Aeromonas hydrophila*, and an adh polynucleotide from *Thermoanaerobacter brockii*.

In some embodiments, the recombinant polynucleotide contains an alsS polynucleotide from *Bacillus subtilis*, an alsD polynucleotide from *Gluconacetobacter xylinus*, and an adh polynucleotide from *Candida parapsilosis*. In some embodiments, the recombinant polynucleotide contains an alsS polynucleotide from *Bacillus subtilis*, an alsD polynucleotide from *Gluconacetobacter xylinus*, and an adh polynucleotide from *Leuconostoc pseudomesenteroides*. In some embodiments, the recombinant polynucleotide contains an alsS polynucleotide from *Bacillus subtilis*, an alsD polynucleotide from *Gluconacetobacter xylinus*, and an adh polynucleotide from *Clostridium beijerinckii*. In some embodiments, the recombinant polynucleotide contains an alsS polynucleotide from *Bacillus subtilis*, an alsD polynucleotide from *Gluconacetobacter xylinus*, and an adh polynucleotide from *Thermoanaerobacter brockii*.

In some embodiments, recombinant polynucleotides of the present disclosure are introduced into a host organism. In some embodiments, the host organism is *E. coli*. In preferred embodiments, the host organism is a cyanobacterium. In preferred embodiments, the host organism is *S. elongatus*.

Introduction of the recombinant polynucleotides into the host organism results in transformation of the host, producing a transformed organism.

As used herein, "transformed" organisms are those organisms that have been provided a recombinant polynucleotide molecule. Transformed organisms therefore differ from wild-type organisms in that they contain exogenous genetic information. Transformed organisms, by this definition, are also recombinant organisms. Methods of transforming host organisms are elaborated upon in Example 1. However, one of skill in the art will recognize that additional methods of transformation may exist and may be used in the methods and compositions of the present disclosure where appropriate.

In preferred embodiments of the disclosure, the transformed organisms produce acetoin. In preferred embodiments, the transformed organisms produce higher levels of acetoin as compared to a wild-type organism. In preferred embodiments of the disclosure, the transformed organisms produce 2,3-butanediol. In preferred embodiments, the transformed organisms produce higher levels of 2,3-butanediol as compared to a wild-type organism.

Methods of Producing Acetoin and 2,3-Butanediol

In some embodiments, a method of producing acetoin is provided in the disclosure. The method involves the step of providing a cyanobacteria with a recombinant vector including coding sequences for an acetolactate synthase (ALS) and an acetolactate decarboxylase (ALDC) operably linked to a promoter to form a transformed cyanobacteria. The method further involves culturing the transformed cyanobacteria in a photosynthetic environment including $CO_2$ and light whereby expression of the ALS and the ALDC results in the production of acetoin.

In some embodiments, a method of producing 2,3-butanediol is provided in the disclosure. The method involves the step of providing a cyanobacterium with a recombinant vector including coding sequences for an acetolactate synthase (ALS), an acetolactate decarboxylase (ALDC), and a secondary alcohol dehydrogenase (sADH) operably linked to a promoter to form a transformed cyanobacteria. The method further involves culturing the transformed cyanobacteria in a photosynthetic environment including $CO_2$ and light whereby expression of the ALS, the ALDC, and the sADH results in the production of 2,3-butanediol.

In some embodiments, the acetolactate synthase coding sequence, the acetolactate decarboxylase coding sequence, and the secondary alcohol dehydrogenase coding sequence in the recombinant polynucleotides of the present disclosure are from a bacterial or a fungal source. In some embodiments, the acetolactate synthase (ALS) is a bacterial ALS or a fungal ALS. In some embodiments, the acetolactate decarboxylase (ALDC) is a bacterial ALDC or a fungal ALDC. In some embodiments, the secondary alcohol dehydrogenase (sADH) is a bacterial sADH or a fungal sADH.

In some embodiments, the ALS is of bacterial origin. In some embodiments, the ALS is an ALS from a *Bacillus* sp. In some embodiments, the ALS is an ALS from *Bacillus subtilis*.

"Bacteria", or "eubacteria", refers to a domain of prokaryotic organisms. The recombinant polynucleotides and coding sequences of the present disclosure may be of bacterial origin. Bacteria include at least 11 distinct groups as follows: (1) Gram-positive (gram+) bacteria, of which there are two major subdivisions: (1) high G+C group (Actinomycetes, Mycobacteria, *Micrococcus*, others) (2) low G+C group (*Bacillus, Clostridia, Lactobacillus*, Staphylococci, Streptococci, Mycoplasmas); (2) Proteobacteria, e.g., Purple photosynthetic+non-photosynthetic Gram-negative bacteria (includes most "common" Gram-negative bacteria); (3) Cyanobacteria, e.g., oxygenic phototrophs; (4) Spirochetes and related species; (5) Planctomyces; (6) *Bacteroides, Flavobacteria*; (7) *Chlamydia*; (8) Green sulfur bacteria; (9) Green non-sulfur bacteria (also anaerobic phototrophs); (10) Radioresistant micrococci and relatives; (11) *Thermotoga* and *Thermosipho thermophiles* (see, e.g. US 2011/0250060).

"Fungi" or "fungal" refers to members of a large group of eukaryotic organisms including yeasts, molds, and mushrooms. Fungi are abundant and diverse organisms that fall under the classification of *Eumycota*. The recombinant polynucleotides and coding sequences of the present disclosure may be of fungal origin. The fungal origin of the recombinant polynucleotides may be from fungi including species from the groups *Blastocladiomycetes, Chytridiomycetes, Glomeromycetes, Microsporidia, Neocallimastigomycetes, Ascomycetes*, and *Basidiomycetes*.

In some embodiments, the sADH is a fungal sADH. In some embodiments, the sADH is an ascomycete sADH, a firmicutes sADH, or a saccharomycete sADH.

The present disclosure relates to cyanobacteria, which are a type of photoautotrophic bacteria. Photoautotrophic bacteria are typically Gram—negative rods which obtain their energy from sunlight through the processes of photosynthesis. In this process, sunlight energy is used in the synthesis of carbohydrates, which in recombinant photoautotrophs can be further used as intermediates in the synthesis of biofuels. In other embodiment, the photoautotrophs serve as a source of carbohydrates for use by nonphotosynthetic microorganism (e.g., recombinant *E. coli*) to produce biofuels by a metabolically engineered microorganism. Certain photoautotrophs called anoxygenic photoautotrophs grow only under anaerobic conditions and neither use water as a source of hydrogen nor produce oxygen from photosynthesis. Other photoautotrophic bacteria are oxygenic photoautotrophs. These bacteria are typically cyanobacteria. They use chlorophyll pigments and photosynthesis in photosynthetic processes resembling those in algae and complex plants. During the process, they use water as a source of hydrogen and produce oxygen as a product of photosynthesis (see, e.g. US 2011/0250060).

In some embodiments, the present disclosure provides cyanobacteria that contain recombinant polynucleotides for use in the production of acetoin and 2,3-butanediol. In some embodiments, the cyanobacteria are a *Synechococcus* sp. In some embodiments, the *Synechococcus* sp. is *Synechococcus elongatus*. In some embodiments, the *Synechococcus elongatus* is *Synechococcus elongatus* PCC7942. One of skill in the art will recognize that other cyanobacteria can be used according to the present disclosure. Examples of other exemplary cyanobacteria include marine cyanobacteria such as *Synechococcus* sp. WH8102, thermostable cyanobacteria such as *Thermosynechococcus elongatus* BP-1, photoheterotrophic cyanobacteria such as *Synechocystis* sp. PCC6803 and filamentous cyanobacteria such as *Nostoc punctiforme*.

Cyanobacteria include various types of bacterial rods and cocci, as well as certain filamentous forms. The cells contain thylakoids, which are cytoplasmic, platelike membranes containing chlorophyll. The organisms produce heterocysts, which are specialized cells believed to function in the fixation of nitrogen compounds (see, e.g. US 2011/0250060).

As used herein, "photosynthetic environment" refers to any environment where the environmental conditions are suitable to allow a photosynthetic cell to perform photosynthesis. Notably, such an environment would contain sufficient quantities of carbon dioxide ($CO_2$) and light to allow photosynthesis to occur.

The $CO_2$ may be provided to the organism in a variety of means. $CO_2$ is naturally present in the atmosphere, so no additional supplementation of this compound to the organism may be necessary as long as the environment surrounding the organism contains sufficient quantities of $CO_2$ to allow a photosynthetic organism to perform photosynthesis. This is preferred, as this method removes $CO_2$ from the environment and uses it as a starting molecule in the biological synthesis of a commodity chemical.

The light used in the methods of the present disclosure may be of any quality, quantity, and from any source known in the art sufficient to allow a photosynthetic organism to perform photosynthesis. The quality of light used may be of any wavelength in the visible light spectrum, such as from 400 nm to 800 nm, or any other quality of light suitable to promote photosynthesis. The quantity of light in the photosynthetic environment may be of any quantity as long as the quantity of light is sufficient to allow photosynthesis to occur. Quantities of light suitable for use in the methods of the present disclosure are provided in Example 1. However, these quantities of light are merely exemplary and are in no way limiting of the quantity of light that could be used in the disclosed methods. One of skill in the art would readily understand the scope of light quantities suitable for use in the disclosed methods.

The source of light may be from any light-emitting source such that the light is sufficient to promote photosynthesis in a photosynthetic organism. The light may be from a fluorescent bulb or a light-emitting diode. Alternatively, the light may be from natural sunlight. One of skill would readily understand that many different light sources could be used in the methods of the present disclosure. Possible light sources are provided in Example 1, but these are mere possibilities and in no way limit the scope of light sources applicable to the methods of the present disclosure.

In some embodiments, the production of one or more of acetoin and 2,-3 butanediol occurs as a result of culturing recombinant cyanobacteria of the present disclosure under constant light. One of skill will readily recognize that constant light energy is only one method of providing light to drive photosynthesis. Other light duration regimes also have use in the present disclosure and will be apparent to those of skill in the art.

In some embodiments, the production of one or more of acetoin and 2,3-butanediol occurs as a result of culturing recombinant cyanobacteria of the present disclosure in the presence of bicarbonate.

In preferred embodiments, the methods of the disclosure produce transformed cyanobacteria that produce higher levels of acetoin as compared to control cyanobacteria lacking the recombinant polynucleotide under the same conditions. In preferred embodiments, the methods of the disclosure produce a transformed cyanobacteria that produces higher levels of 2,3-butanediol as compared to a control cyanobacteria lacking the recombinant polynucleotide under the same conditions.

As used herein, control cyanobacteria refer to cyanobacteria that are substantially the same as the recombinant cyanobacteria, but that the control cyanobacteria lack the recombinant polynucleotides of the recombinant cyanobacteria described in the present disclosure. Examples of control cyanobacteria include wild-type cyanobacteria of the same species as the recombinant cyanobacteria. Such wild-type cyanobacteria could include the parent of the recombinant cyanobacteria. Other control cyanobacteria include those carrying the vectors of the present disclosure but without the recombinant polynucleotides located in the vector. Other types of control cyanobacteria or organisms will be apparent to those skilled in the art.

Exemplary methods of detecting acetoin and 2,3-butanediol concentrations from organisms are provided in Example 1. However, one of skill in the art would recognize that many different methods of detecting metabolite concentrations are known and practiced. Any method that can quantify the concentration of acetoin and/or 2,3-butanediol in a sample could have application in the present disclosure.

The 2,3-butanediol molecule has two asymmetric carbons, and thus can have differential chirality at each stereocenter. The 2,3-butanediol produced in the methods of the present disclosure may be (R,R)-2,3-butanediol, it may be (S,S)-2,3-butanediol, or it may be *meso*-2,3-butanediol in which one asymmetric carbon of the molecule has an S-configuration and one asymmetric carbon of the molecule has an R-configuration.

Supplemental Information

The practice of the present disclosure will employ, unless otherwise indicated, conventional techniques of molecular biology (including recombinant techniques), microbiology, cell biology, biochemistry and immunology, which are within the skill of the art. Such techniques are explained fully in the literature, such as, Molecular Cloning: A Laboratory Manual, second edition (Sambrook et al., 1989); Oligonucleotide Synthesis (Gait, ed., 1984); Animal Cell Culture (Freshney, ed., 1987); Handbook of Experimental Immunology (Weir & Blackwell, eds.); Gene Transfer Vectors for Mammalian Cells (Miller & Calos, eds., 1987); Current Protocols in Molecular Biology (Ausubel et al., eds., 1987); PCR: The Polymerase Chain Reaction, (Mullis et al., eds., 1994); Current Protocols in Immunology (Coligan et al., eds., 1991); The Immunoassay Handbook (Wild ed., Stockton Press NY, 1994); Bioconjugate Techniques (Hermanson, ed., Academic Press, 1996); and Methods of Immunological Analysis (Masseyeff, Albert, and Staines, eds., Weinheim: VCH Verlags gesellschaft mbH, 1993).

The percent identity between the two sequences is a function of the number of identical positions shared by the sequences, taking into account the number of gaps, and the length of each gap, which need to be introduced for optimal alignment of the two sequences. For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters. When comparing two sequences for identity, it is not necessary that the sequences be contiguous, but any gap would carry with it a penalty that would reduce the overall percent identity. For blastn, the default parameters are Gap opening penalty=5 and Gap extension penalty=2. For blastp, the default parameters are Gap opening penalty=11 and Gap extension penalty=1.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted using known algorithms (e.g., by the local homology algorithm of Smith and Waterman, Adv Appl Math, 2:482, 1981; by the homology alignment algorithm of Needleman and Wunsch, J Mol Biol, 48:443, 1970; by the search for similarity method of Pearson and Lipman, Proc Natl Acad Sci USA, 85:2444, 1988; by computerized implementations of these algorithms FASTDB (Intelligenetics), BLAST (National Center for Biomedical Information), GAP, BESTFIT, FASTA, and TFASTA in the Wisconsin Genetics Software Package (Genetics Computer Group, Madison, Wis.), or by manual alignment and visual inspection.

A preferred example of an algorithm that is suitable for determining percent sequence identity and sequence similarity is the FASTA algorithm (Pearson and Lipman, Proc Natl Acad Sci USA, 85:2444, 1988; and Pearson, Methods Enzymol, 266:227-258, 1996). Preferred parameters used in a FASTA alignment of DNA sequences to calculate percent identity are optimized, BL50 Matrix 15:-5, k-tuple=2; joining penalty=40, optimization=28; gap penalty-12, gap length penalty=-2; and width=16.

Another preferred example of algorithms suitable for determining percent sequence identity and sequence similarity are the BLAST and BLAST 2.0 algorithms (Altschul et al., Nuc Acids Res, 25:3389-3402, 1977; and Altschul et al., J Mol Biol, 215:403-410, 1990, respectively). BLAST and BLAST 2.0 are used, with the parameters described herein, to determine percent sequence identity for the nucleic acids and proteins of the disclosure. Software for performing BLAST analyses is publicly available through the National Center for Biotechnology Information website. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold. These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a word length (W) of 11, an expectation (E) of 10, M=5, N=-4 and a comparison of both strands. For amino acid sequences, the BLASTP program uses as defaults a word length of 3, and expectation (E) of 10, and the BLOSUM62 scoring matrix (Henikoff and Henikoff, Proc Natl Acad Sci USA, 89:10915, 1989) alignments (B) of 50, expectation (E) of 10, M=5, N=-4, and a comparison of both strands.

The BLAST algorithm also performs a statistical analysis of the similarity between two sequences (See, e.g., Karlin and Altschul, Proc Natl Acad Sci USA, 90:5873-5787, 1993). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

Another example of a useful algorithm is PILEUP. PILEUP creates a multiple sequence alignment from a group of related sequences using progressive, pairwise alignments to show relationship and percent sequence identity. It also plots a tree or dendogram showing the clustering relationships used to create the alignment. PILEUP uses a simplification of the progressive alignment method (Feng and Doolittle, J Mol Evol, 35:351-360, 1987), employing a method similar to a published method (Higgins and Sharp, CABIOS 5:151-153, 1989). The program can align up to 300 sequences, each of a maximum length of 5,000 nucleotides or amino acids. The multiple alignment procedure begins with the pairwise alignment of the two most similar sequences, producing a cluster of two aligned sequences. This cluster is then aligned to the next most related sequence or cluster of aligned sequences. Two clusters of sequences are aligned by a simple extension of the pairwise alignment of two individual sequences. The final alignment is achieved by a series of progressive, pairwise alignments. The program is run by designating specific sequences and their amino acid or nucleotide coordinates for regions of sequence comparison and by designating the program parameters. Using PILEUP, a reference sequence is compared to other test sequences to determine the percent sequence identity relationship using the following parameters: default gap weight (3.00), default gap length weight (0.10), and weighted end gaps. PILEUP can be obtained from the GCG sequence analysis software package, e.g., version 7.0 (Devereaux et al., Nuc Acids Res, 12:387-395, 1984).

Another preferred example of an algorithm that is suitable for multiple DNA and amino acid sequence alignments is the CLUSTALW program (Thompson et al., Nucl Acids. Res, 22:4673-4680, 1994). ClustalW performs multiple pairwise comparisons between groups of sequences and assembles them into a multiple alignment based on homology. Gap open and Gap extension penalties were 10 and 0.05 respectively. For amino acid alignments, the BLOSUM algorithm can be used as a protein weight matrix (Henikoff and Henikoff, Proc Natl Acad Sci USA, 89:10915-10919, 1992).

Polynucleotides of the disclosure further include polynucleotides that encode conservatively modified variants of the polypeptides of Table 4 and the nucleic acid and amino acid sequences of SEQS ID NOS:1-23. "Conservatively modified variants" as used herein include individual mutations that result in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the disclosure. The following eight groups contain amino acids that are conservative substitutions for one another: 1. Alanine (A), Glycine (G); 2. Aspartic acid (D), Glutamic acid (E); 3. Asparagine (N), Glutamine (Q); 4. Arginine (R), Lysine (K); 5. Isoleucine (I), Leucine (L), Methionine (M), Valine (V); 6. Phenylalanine (F), Tyrosine (Y), Tryptophan (W); 7. Serine (S), Threonine (T); and 8. Cysteine (C), Methionine (M).

The terms "derived from" or "of" when used in reference to a nucleic acid or protein indicates that its sequence is identical or substantially identical to that of an organism of interest.

The term "corresponding" when used in reference to a cyanobacterium, refers to a cynaobacterium of the same genus and species as the cynaobacterium of interest. For instance in regard to an S. elongates comprising a recombinant polynucleotide encoding an ALS and an ALDC, a "corresponding cynaobacterium" is an S. elongates cell (wild type, parental, or otherwise comparable) lacking the recombinant polynucleotide.

The terms "decrease," "reduce" and "reduction" as used in reference to biological function (e.g., enzymatic activity, production of compound, expression of a protein, etc.) refer to a measurable lessening in the function by preferably at least 10%, more preferably at least 50%, still more preferably at least 75%, and most preferably at least 90%. Depending upon the function, the reduction may be from 10% to 100%. The term "substantial reduction" and the like refers to a reduction of at least 50%, 75%, 90%, 95% or 100%.

The terms "increase," "elevate" and "elevation" as used in reference to biological function (e.g., enzymatic activity, production of compound, expression of a protein, etc.) refer to a measurable augmentation in the function by preferably at least 10%, more preferably at least 50%, still more preferably at least 75%, and most preferably at least 90%. Depending upon the function, the elevation may be from 10% to 100%; or at least 10-fold, 100-fold, or 1000-fold up to 100-fold, 1000-fold or 10,000-fold or more. The term "substantial elevation" and the like refers to an elevation of at least 50%, 75%, 90%, 95% or 100%.

The terms "isolated" and "purified" as used herein refers to a material that is removed from at least one component with which it is naturally associated (e.g., removed from its original environment). The term "isolated," when used in reference to a biosythetically-produced chemical, refers to a chemical that has been removed from the culture medium of the bacteria that produced the chemical. As such an isolated chemical is free of extraneous or unwanted compounds (e.g., substrate molecules, bacterial components, etc.).

As used herein, the singular form "a", "an", and "the" includes plural references unless indicated otherwise. For example, "an" ALD includes one or more ALDs.

The phrase "comprising" as used herein is open-ended, indicating that such embodiments may include additional elements. In contrast, the phrase "consisting of" is closed, indicating that such embodiments do not include additional elements (except for trace impurities). The phrase "consisting essentially of" is partially closed, indicating that such embodiments may further comprise elements that do not materially change the basic characteristics of such embodiments. It is understood that aspects and embodiments described herein as "comprising" include "consisting" and/or "consisting essentially of" aspects and embodiments.

EXAMPLES

To better facilitate an understanding of the embodiments of the disclosure, the following examples are presented. The following examples are merely illustrative and are not meant to limit any embodiments of the present disclosure in any way.

Abbreviations: ALDC (acetolactate decarboxylase); ALS (acetolactate synthase); sADH (secondary alcohol dehydrogenase); and 23BD (2,3-butanediol).

Example 1

Production of Acetoin and 2,3-Butanediol in Recombinant Microorganisms

The following example describes the engineering of heterologous acetoin and 2,3-butanediol biosynthetic pathways in an exemplary photosynthetic microorganism (e.g., Synechococcus elongatus), as well as the successful production of these commodity chemicals from carbon dioxide and light energy.

Materials and Methods

Reagents. The chemicals (R,R)-2,3-butanediol, meso-2,3-butanediol, (S,S)-2,3-butanediol and acetoin were obtained from Sigma-Aldrich (St. Louis, Mo.). NADH and IPTG were obtained from Fisher Scientific (Hanover Park, Ill). Phusion polymerase was purchased from NEB (Ipswich, Mass.). KOD polymerase and NADPH were purchased from EMD4Biosciences (San Diego, Calif.). Gentamicin was purchased from Teknova (Hollister, Calif.). Oligonucleotides were synthesized from Integrated DNA Technologies, Inc. (San Diego, Calif.).

Strains and Plasmids. Strains described herein are listed in Table 1, while plasmids described herein are listed in Table 2. All plasmids except pAL60 were constructed using sequence and ligase independent cloning (SLIC)(50) in *E. coli* XL1-Blue (Agilent Technologies, Santa Clara, Calif.). Primers for construction and genotype verification are listed in Table 3.

TABLE 1

Microorganism Strains

| Strains | Genotype/Description^ |
|---|---|
| *E. coli* Strain | |
| XL-1 Blue | recA1 endA1 gyrA96 thi-1 hsdR17 supE44 relA1 lac [F' proAB lacIqZΔM15 Tn10 (Tetr)] |
| *S. elongatus* Strains | |
| PCC7942 | Wild Type |
| AL723 | $P_{LlacO1}$ and Gent$^R$ integrated at NS |
| AL762 | alsS (*B. s.*) integrated at NS |
| AL763 | alsS (*B. s.*)-alsD (*E. a.*) integrated at NS |
| AL764 | alsS (*B. s.*)-alsD (*E. c.*) integrated at NS |
| AL765 | alsS (*B. s.*)-alsD (*B. l.*) integrated at NS |
| AL766 | alsS (*B. s.*)-alsD (*B. s.*) integrated at NS |
| AL767 | alsS (*B. s.*)-alsD (*A. h.*) integrated at NS |

TABLE 1-continued

Microorganism Strains

| Strains | Genotype/Description^ |
|---|---|
| AL768 | alsS (*B. s.*)-alsD (*G. x.*) integrated at NS |
| AL769 | alsS (*B. s.*)-alsD (*E. a.*)-adh (*C. p.*) integrated at NS |
| AL770 | alsS (*B. s.*)-alsD (*E. a.*)-adh (*L. p.*) integrated at NS |
| AL771 | alsS (*B. s.*)-alsD (*E. a.*)-adh (*C. b.*) integrated at NS |
| AL753 | alsS (*B. s.*)-alsD (*A. h.*)-adh (*T. b.*) integrated at NS |
| AL756 | alsS (*B. s.*)-alsD (*E. a.*)-adh (*C. b.*) integrated at NS |
| AL757 | alsS (*B. s.*)-alsD (*A. h.*)-adh (*T. b.*) integrated at NS |

^All strains this study except XL-1 Blue (Agilent Technologies) and PCC7942 (Golden et al., *Methods Enzymol*, 153: 215-231, 1987).

TABLE 2

Plasmids

| Plasmid | Description^ |
|---|---|
| pAL60 | NS targeting vector; ColE1 ori; Ptrc; Amp$^R$ |
| pSA69 | P15A ori; Kan$^R$, $P_L$lacO$_1$:alsS (*B. s.*)-ilvC (*E. coli*)-ilvD (*E. coli*) |
| pAL299 | As pAL60, but $P_{LlacO1}$ :: alsS (*B. s.*)-alsD (*A. h.*)-adh (*T. b.*); Gent$^R$ |
| pAL300 | As pAL60, but $P_{LlacO1}$:: alsS (*B. s.*)-alsD (*A. h.*)-adh (*C. b.*); Gent$^R$ |
| pAL301 | As pAL60, but $P_{LlacO1}$:: alsS (*B. s.*); Gent$^R$ |
| pAL302 | As pAL60, but $P_{LlacO1}$:: alsS (*B. s.*)-alsD (*E. a.*); Gent$^R$ |
| pAL303 | As pAL60, but $P_{LlacO1}$:: alsS (*B. s.*)-alsD (*E. c.*); Gent$^R$ |
| pAL304 | As pAL60, but $P_{LlacO1}$:: alsS (*B. s.*)-alsD (*B. l.*); Gent$^R$ |
| pAL305 | As pAL60, but $P_{LlacO1}$:: alsS (*B. s.*)-alsD (*B. s.*); Gent$^R$ |
| pAL306 | As pAL60, but $P_{LlacO1}$:: alsS (*B. s.*)-alsD (*A. h.*); Gent$^R$ |
| pAL307 | As pAL60, but $P_{LlacO1}$c:: alsS (*B. s.*)-alsD (*G. x.*); Gent$^R$ |
| pAL308 | As pAL60, but $P_{LlacO1}$:: alsS (*B. s.*)-alsD (*E. a.*)-adh (*C. p.*); Gent$^R$ |
| pAL309 | As pAL60, but $P_{LlacO1}$:: alsS (*B. s.*)-alsD (*E. a.*)-adh (*L. p.*); Gent$^R$ |
| pAL310 | As pAL60, but $P_{LlacO1}$:: alsS (*B. s.*)-alsD (*E. a.*)-adh (*C. b.*); Gent$^R$ |
| pAL312 | As pAL60, but $P_{LlacO1}$; Gent$^R$ |
| pAL315 | As pAL60, but $P_{LlacO1}$:: alsS (*B. s.*)-alsD (*E. a.*)-adh (*T. b.*); Gent$^R$ |

^All plasmids this study except pSA69 (Atsumi et al., *Nature*, 451: 86-89, 2008)

TABLE 3

Oligonucleotides used in Plasmid Construction and Verification of Integration

| Name | Sequence (5' → 3') | Plasmid |
|---|---|---|
| MC173 | CTATGACGTCGGCGTTTTCTGCTACATGGGCCGTGAG (SEQ ID NO: 24) | pAL60 |
| MC176 | CTAACCTAGGGGAAGTCCAGCGCAATCAGCGGAGTTG (SEQ ID NO: 25) | pAL60 |
| MC181 (P1) | CTAAATGCATTAAGTTGTTACTAGTGCTTGGATTCTCACC (SEQ ID NO: 26) | |
| IM15 (P2) | CTAGAGAGCTTTCGTTTTCATGAG (SEQ ID NO: 27) | |
| IM88 (P3) | CGGGGAACTCATGAAAACGAAAGCTCTCTA (SEQ ID NO: 28) | |
| IM89 (P4) | GTTGGGTAGCAGACAATGCGGGGGATCTGG (SEQ ID NO: 29) | |
| AK1 | GGTTTTGCACCAGGATCCCGCTCGAGTTGACGCGTGCTTA (SEQ ID NO: 30) | pAL301 |
| AK3 | TCACTGCCCGCTTTCCAGTC (SEQ ID NO: 31) | pAL301 |

TABLE 3-continued

Oligonucleotides used in Plasmid Construction and Verification of Integration

| Name | Sequence (5' → 3') | Plasmid |
|------|--------------------|---------|
| IM103 | AGTTGACGCGTGCTTATCATAATTGTGAGCGGATAACAAT (SEQ ID NO: 32) | pAL301 |
| IM15 | CTAGAGAGCTTTCGTTTTCATGAG (SEQ ID NO: 33) | pAL302 |
| IM16 | TAGGTCGACGAGGAATCACCATGAATCATGCTTCAG (SEQ ID NO: 34) | pAL302 |
| IM17 | AGGTCGACTCTAGAGGATCTCTAACTTTCTACTGAACGGA (SEQ ID NO: 35) | pAL302 |
| IM19 | TAGGTCGACGAGGAATCACCATGAGCGCCCTGCTAA (SEQ ID NO: 36) | pAL303 |
| IM20 | CAGGTCGACTCTAGAGGATCTTTAGTTTTCGACGGA (SEQ ID NO: 37) | pAL303 |
| IM21 | TAGGTCGACGAGGAATCACCATGGAAATAGGCTTTA (SEQ ID NO: 38) | pAL307 |
| IM22 | CAGGTCGACTCTAGAGGATCTTCAGCCGCCCTCGGC (SEQ ID NO: 39) | pAL307 |
| IM23 | CTAGGTCGACGAGGAATCACCATGAAAAGTGCAAG (SEQ ID NO: 40) | pAL304 |
| IM24 | CAGGTCGACTCTAGAGGATCTTTACTCGGGATTGCCT (SEQ ID NO: 41) | pAL304 |
| IM27 | TAGGTCGACGAGGAATCACCATGAAACGTGAGTCG (SEQ ID NO: 42) | pAL305 |
| IM28 | CAGGTCGACTCTAGAGGATCTCTACTCGGGAGAACC (SEQ ID NO: 43) | pAL305 |
| IM29 | TAGGTCGACGAGGAATCACCATGGAAACTAATAGC (SEQ ID NO: 44) | pAL306 |
| IM30 | CAGGTCGACTCTAGAGGATCTCTAACCCTCAGCCGC (SEQ ID NO: 45) | pAL306 |
| IM39 | CGGGATCCTGGTGCAAAACCTTTCGCGGTA (SEQ ID NO: 46) | pAL301 |
| IM44 | GTACCTTTCTCCTCTTCTAACTTTCTACTGAACGGATGGC (SEQ ID NO: 47) | pAL308, pAL309, pAL310, pAL315 |
| IM45 | TAGAAGAGGAGAAAGGTACATGAAAGGTTTTGCCA (SEQ ID NO: 48) | pAL310 |
| IM46 | CAGGTCGACTCTAGAGGATCTCTACAGGATTACGAC (SEQ ID NO: 49) | pAL310 |
| IM47 | GTTAGAAGAGGAGAAAGGTACATGAAGGGTTTCGC (SEQ ID NO: 50) | pAL315 |
| IM48 | CAGGTCGACTCTAGAGGATCTCTATGCCAAAATGAC (SEQ ID NO: 51) | pAL315 |
| IM49 | TTAGAAGAGGAGAAAGGTACATGGGGGAGATTGAG (SEQ ID NO: 52) | pAL308 |
| IM50 | CAGGTCGACTCTAGAGGATCTCTAGGGGCATGTGTAA (SEQ ID NO: 53) | pAL308 |
| IM51 | TTAGAAGAGGAGAAAGGTACATGACAAAGAAAGT (SEQ ID NO: 54) | pAL309 |
| IM52 | AGGTCGACTCTAGAGGATCTCTAGTGAAACTGCATG (SEQ ID NO: 55) | pAL309 |
| IM114 | GGTCGACTCTAGAGGATCTTGTACCTTTCTCCTCTTTAA (SEQ ID NO: 56) | pAL312 |

TABLE 3-continued

Oligonucleotides used in Plasmid Construction and Verification of Integration

| Name | Sequence (5' → 3') | Plasmid |
|---|---|---|
| IM125 | GTACCTTTCTCCTCTTCTAACCCTCAGCCGCACGGATAGC (SEQ ID NO: 57) | pAL299, pAL300 |
| IM11 | AGATCCTCTAGAGTCGACCTG (SEQ ID NO: 58) | pAL299, pAL300, pAL312 |

A neutral site (NS) located between Synpcc7942_0893 (903,564-904,283 bp) and Synpcc7942_0894 (904,845-905,417 bp) in the S. elongatus chromosome was used for insertion of an expression cassette. This region was amplified with primers MC173 and MC176. PCR products were digested with AatII and AvrII and cloned into pZE12-luc (51) cut with the same enzyme, creating pAL60.

The fragment containing $P_{LlacO1}$ and alsS (B.s.) genes was amplified with primers IM103 and IM11 and $lacI^q$ was amplified with primers IM39 and AK3 from pSA69 (52). The resulting fragments were inserted into pAL60 by SLIC, creating pAL301.

To clone alsD (E. a.), we used genomic DNA of E. aerogenes ATCC13048 (ATCC) as a PCR template with primers IM16 and IM 17. To clone alsD (E. c.), genomic DNA of E. cloacae ATCC 13047 (ATCC) was used as a PCR template with primers IM19 and IM20. To clone alsD (B. 1. ), genomic DNA of B. licheniformis ATCC 14580 (ATCC) was used as a PCR template with primers IM23 and IM24. To clone alsD (G. x.), genomic DNA of G. xylinus (NBRC 3288) was used as a PCR template with primers IM21 and IM22. alsD (B. s) and alsD (A. h.) were chemically synthesized by DNA2.0 Inc. (Menlo Park, Calif.) to optimize codon usage for S. elongatus. Each alsD gene was cloned into downstream of alsS (B. s.) on pAL301 by SLIC, creating pAL302, pAL303, pAL304, pAL305, pAL306 and pAL307. To construct plasmid pAL312, we used plasmid pAL301 as a PCR template and primers IM114 and IM11 to amplify the entire plasmid, without the alsS gene. The resulting fragment was assembled by SLIC. All four adh genes were chemically synthesized by DNA2.0 Inc. (Menlo Park, Calif.) to optimize codon usage for S. elongatus. Each adh gene was cloned into downstream of alsD (E. a.) on pAL302 by SLIC, creating pAL308, pAL309, pAL310 and pAL315. The adh (T.b.) and adh (C. b.) genes were clone into downstream of alsD (A. h.) on pAL306 by SLIC, creating pAL299 and pAL300, respectively.

Transformation of S. elongatus. Transformation of S. elongatus was performed as described (53). Strains were segregated several times by transferring colonies to fresh selective plates. Correct recombinants were confirmed by PCR to verify integration of targeting genes into the chromosome. The strains used and constructed are listed in Table 1. NS between Synpcc7942_0893 (903,564-904,283 bp) and Synpcc7942_0894 (904,845-905,417 bp) on the S. elongatus chromosome was used as a targeting site for recombination. It was confirmed that insertion of the gentamicin resistance gene at this site does not affect the growth of cells.

Oxygen Evolution. Evolution of $O_2$ was measured using a clark-type electrode with the Oxygraph system (Hansatech Instruments Ltd, Norfolk, UK). Under ambient light conditions, 1 ml of cells was transferred to the 4 ml borosilicate glass chamber and headspace gas was expelled using a center bored contact plunger with rubber cap. Cells were stirred at 100 rpm using a magnetic flea, and subjected to 2 minutes of darkness to allow the cells to equilibrate with the surrounding water jacket to 25° C. A constant negative rate over at least 30 s was recorded after equilibration. Cells were then subjected to excess light (60 µE $s^{-1}$ $m^{-2}$) and allowed to equilibrate for at least 2 minutes until a constant rate could be measured over at least 60 s.

Enzyme Assays. S. elongatus cells were collected 72 h after induction by centrifugation (4000 g, 5 min, washed in 50 mM potassium phosphate buffer (pH 7.5) and resuspended in the same buffer. Crude extract were prepared with 0.1-mm glass beads and a Mini bead beater (Mini Bead Beater 8 (BioSpec Products, Inc., Bartlesville, Okla.)). The total protein determination was performed by Advanced Protein Assay Reagent from Cytoskeleton, Inc. (Denver, Colo.).

Acetolactate synthase (ALS) activity was determined as described (54). The concentration of acetoin produced was measured by a standard curve using pure acetoin. One specific unit of AlsS activity corresponds to the formation of 1 nmol of acetoin per mg of protein per minute.

Alcohol dehydrogenase (ADH) activity was determined by measuring the oxidation of NAD(P)H. The reaction mixture contained 50 mM 3-(N-morpholino) propanesulfonic acid (MOPS) pH 7.0, 25 mM acetoin and 0.2 mM NAD(P)H. The consumption of NAD(P)H was monitored at 340 nm. One specific unit of ADH activity corresponds to the oxidation of 1 nmol of NAD(P)H per minute per mg of protein.

Figure 7:
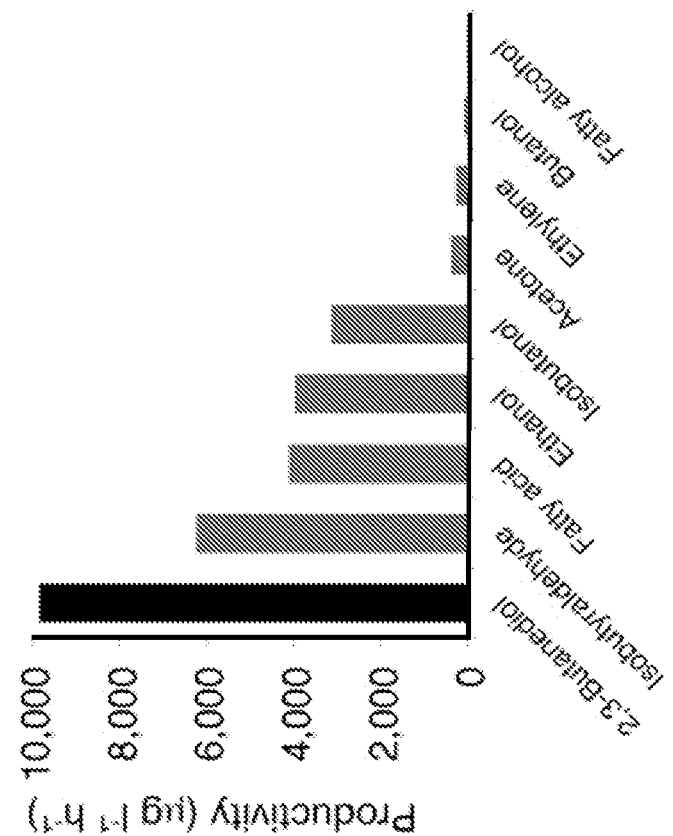
FIG. 7 shows a comparison of productivities for various chemicals produced from exogenous pathways in cyanobacteria. Source data is obtained from: 23BD (this disclosure), isobutyraldehyde and isobutanol (Atsumi et al., *Nat Biotechnol*, 27:1177-1180, 2009), fatty acid (Liu et al., *Proc Natl Acad Sci USA*, 108:6899-6904, 2011), ethanol (Dexter and Pengcheng, *Energy Environ Sci*, 2:857-864, 2009), acetone (Zhou et al., *Metab Eng*, 14:394-400, 2012), ethylene (Takahama et al., *J Biosci Bioeng*, 95:302-305, 2003), butanol (Lan and Liao, *Proc Natl Acad Sci USA*, 109:6018-6023, 2012), fatty alcohol (Tan et al., *Metab Eng*, 13:169-176, 2011). The detailed calculations are described in Example 1.

Calculation of Productivities. The following narrative provides a summary of how productivity calculations were made for specific compounds (FIG. 7).

For 2,3-butanediol, productivity per day was averaged over 3 days. Per day yields were 175 mg $l^{-1}$, 297 mg $l^{-1}$, and 237 mg $l^{-1}$ for the time periods from 24 h-48 h, 48 h-72 h, and 72 h-96 h respectively. By converting units this becomes 7292 µg $l^{-1}$ $h^{-1}$, 12375 µg $l^{-1}$ $h^{-1}$, and 9875 µg $l^{-1}$ $h^{-1}$ respectively. The average of these rates is 9847 µg $l^{-1}$ $h^{-1}$.

For isobutyraldehyde, the rate is calculated in literature (55).

For fatty acids, the apparent maximum titer was 197 mg $l^{-1}$ which was produced over a minimum of 2 days—converting units gives 4104.2 µg $l^{-1}$ $h^{-1}$ (56).

For ethanol, the apparent maximum is 13 millimoles $l^{-1}$ produced in 145 hours. Using the Molar mass of ethanol (46.07 g $mol^{-1}$), this becomes 575.9 mg $l^{-1}$ over 145 hours. Converting units gives 3972 µg $l^{-1}$ (57).

For isobutanol, published titer is 450 mg $l^{-1}$ over 6 days. Converting units gives 3125 µg $l^{-1}$ $h^{-1}$ (55).

For acetone, the apparent maximum titer was 36 mg $l^{-1}$ over 4 days. Converting units gives 375 µg $l^{-1}$ $h^{-1}$ (58).

For ethylene, the apparent maximum rate was 240 nl $ml^{-1}$ $h^{-1}$. This can be approximated as 9.81 µmol $l^{-1}$ $h^{-1}$ using the molar volume of an ideal gas at ambient temperature and pressure (24.465 1 mol$^{-1}$ at 25° C. and 1 atm) and converting units. Using the molar mass of ethylene (28.05 g mol$^{-1}$) this becomes 275.17 µg l$^{-1}$ h$^{-1}$(59).

For 1-butanol, the apparent maximum titer was 19 mg l$^{-1}$ over 10 days. Converting units gives 79.2 µgl$^{-1}$ (60).

For fatty alcohol, the apparent maximum titer was 137.63 µg l$^{1-1}$ over 4 days. Converting units gives 0.48 µg l$^{-1}$ h$^{-1}$ (61).

Culture Conditions. Unless otherwise specified, *S. elongatus* strains were cultured in BG-11 medium (45) with the addition of 50 mM NaHCO$_3$. Cells were grown at 30° C. with rotary shaking (100 rpm) and light (55 µE s$^{-1}$ m$^{-2}$) provided by four 86 cm 20 W fluorescent tubes 5 cm above the cell cultures. Cell growth was monitored by measuring OD$_{730}$.

For acetoin and 23BD production in *S. elongatus*, cells in exponential phase were diluted to an OD$_{730}$ of 0.1 in 25 ml BG-11 medium including 50 mM NaHCO$_3$, 10 mg/L thiamine, and 10 mg/L gentamicin in 125 ml baffled shake flasks. Cultures were grown to an OD$_{730}$ of 0.4-0.6 before induction with 1 mM IPTG. Every 24 hours, the pH was adjusted to 7.5 +/--0.4 with 10N HCl. 10% of the culture volume was removed and an equal volume of BG-11 containing 0.5 M NaHCO$_3$ was added achieving a final concentration of 50 mM NaHCO$_3$ in the culture.

For acetoin and 2,3-butanediol production in *E. coli*, overnight cultures were diluted 1:100 into 5 ml of modified M9 medium (33) containing 50 g/L glucose, 5 g/L yeast extract and 5 mg/L gentamicin in a 30-ml test tube. Cells were grown at 37° C. to an OD of 0.2-0.4 followed by addition of 0.1 mM IPTG. Production was continued at 30° C. on a rotary shaker (250 rpm) for 40 hours.

Acetoin Quantification. Acetoin was quantified by the method of Voges and Proskauer (46-47), adapted to small volume on 96 well plates. Sample concentration was varied between 1-10% of final volume to achieve a result within the linear range of detection. This was achieved by dilution in H$_2$O$_2$O to 100 µl initial volume. For an assay containing 2% sample (most common), 98 µl water and 2 µl of the supernatant were added to wells and mixed. To this was added 100 µl of a solution, prepared at the time of use, consisting of one part 5% Naphthol dissolved in 2.5N NaOH and one part 0.5% Creatine in water. The assay was monitored every 5 minutes and final readings were taken after 40 min, when the slope of the absorbance curve matched the background oxidation rate of Naphthol. Triplicate measurements of no less than 3 standards, including at least one value each above, below and within the desired range, were included in every assay.

2,3-Butanediol Quantification. Supernatant samples from cultures were analyzed with gas chromatography (GC) (Shimadzu) equipped with flame ionization detector and an HP-chiral 20b column (30 m, 0.32-mm internal diameter, 0.25-mm film thickness; Agilent Technologies). Samples were prepared by mixing 9 parts supernatant (diluted as necessary in H$_2$O) with 1 part internal standard. For each analysis the GC oven temperature was held at 40° C. for 4 min, increased with a gradient of 15° C. min until 235° C., and held for 4 min. Ultra high purity Helium was used as the carrier gas. The temperature of the injector and detector were set at 250° C. The stereoisomers were identified by matching retention time to standards for (R,R)-23BD, meso-23BD and (S,S)-23BD.

Results

23BD exhibits low toxicity in *S. elongatus*. To increase the titer and duration of chemical production, low toxicity or constant removal of the product is necessary. Because constant removal and purification of small concentrations during production is not cost-effective on an industrial scale, it was a prerequisite of this study that the chemical target be tolerated at an acceptable volume of greater than 1% (10 g/L) by production strains.

Figure 2:
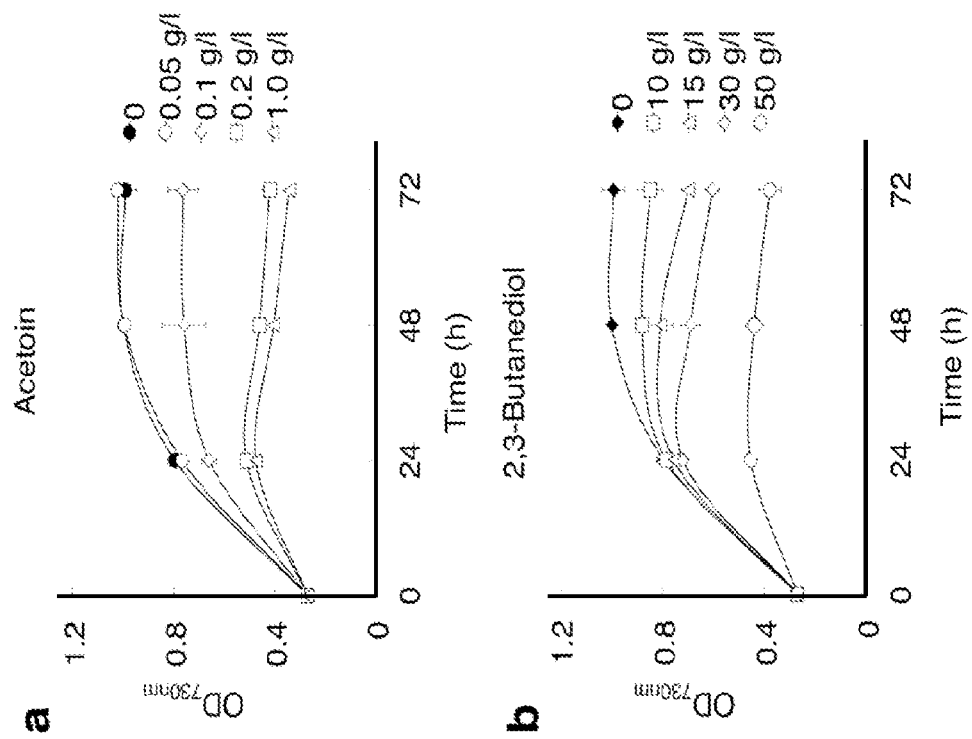
FIG. 2*a-b* illustrate how various concentrations of acetoin and 2,3-butanediol impact the growth rate of *S. elongatus*.

To evaluate acetoin and 23BD toxicity, we tested the growth of *S. elongatus* over 72 h in the presence of 23BD or acetoin. Growth decreased approximately 50% in the presence of 0.2 g/L acetoin, and stopped at 1.0 g/L (FIG. 2A) indicating acute toxicity for this precursor. This is comparable to isobutyraldehyde and isobutanol, which prevent growth of *S. elongatus* at 1 g/L (14). Conversely growth of *S. elongatus* was barely inhibited in the presence of 10 g/L 23BD (FIG. 2B), and still exhibited growth in the presence of 30 g/L 23BD, surpassing our benchmark goal for product tolerance. These results indicate that 23BD is a suitable target for high titer and long-term cyanobacterial production, as long as high flux through acetoin can be maintained to prevent accumulation of the toxic intermediate.

Construction of the Acetoin Biosynthetic Pathway. Acetoin can be produced by the decarboxylation of 2-acetolactate. In this pathway (FIG. 1) two pyruvate molecules are converted into 2-acetolactate by acetolactate synthase (ALS) encoded by alsS. 2-Acetolactate is then decarboxylated to yield acetoin by 2-acetolactate decarboxylase (ALDC) encoded by alsD. Pyruvate, the source of carbon for the pathway, is produced naturally through the fixation of three CO$_2$ molecules in the Calvin-Benson-Bassham cycle (32). Conversion of pyruvate to 2-acetolactate occurs naturally during valine/leucine biosynthesis, albeit in low amounts (33). Previously the alsS gene which encodes ALS from *Bacillus subtilis* (B. s.) was overexpressed to increase carbon flux to 2-acetolactate for the production of isobutyraldehyde and was reported to have relatively high activity (14).

To identify strong ALDC candidates, we used the bioinformatics tool, BRaunschweig ENzyme DAtabase (BRENDA)(34) and a comprehensive literature review. We limited our search to O$_2$ insensitive enzymes, and looked for reports of strong acetoin production. We were further restricted by the need to match pre-sequencing literature reports to chronologically consistent strain names, which now match currently available gene sequences. Based on these criteria six alsD genes were selected (Table 4).

TABLE 4

Acetolactate Decarboxylase (ALDC) and Secondary Alcohol Dehydrogenase (ADH) Genes

| Enzyme | Source Organism | Source | Cofactor | Chirality | Reference |
|---|---|---|---|---|---|
| ALDC | *Enterobacter aerogenes* (E. a.) | ATCC 13048 | | | (48) |
| ALDC | *Enterobacter cloacae* (E. c.) | ATCC 13047 | | | (48) |
| ALDC | *Bacillus licheniformis* (B. l.) | ATCC 14580 | | | (48) |
| ALDC | *Bacillus subtilis* (B. s.)* | str 168 | | | (48) |

TABLE 4-continued

Acetolactate Decarboxylase (ALDC) and Secondary Alcohol Dehydrogenase (ADH) Genes

| Enzyme | Source Organism | Source | Cofactor | Chirality | Reference |
|---|---|---|---|---|---|
| ALDC | Aeromonas hydrophila (A. h.)* | ATCC 7966 | | | (48) |
| ALDC | Gluconacetobacter xylinus (G. x.) | NBRC 3288 | | | (48) |
| ADH | Candida parapsilosis (C. p.)* | M203011 | NADPH | S-installing | (42) |
| ADH | Leuconostoc pseudomesenteroides (L. p.)* | CHCC 2114 | NADPH | S-installing | (43) |
| ADH | Clostridium beijerinckii (C. b.)* | NRRL B593 | NADPH | R-installing | (41) |
| ADH | Thermoanaerobacter brockii (T. b.)* | HTD4 | NADPH | R-installing | (41) |

*Genes were synthesized with codon optimization for expression in S. elongatus

Figure 3:
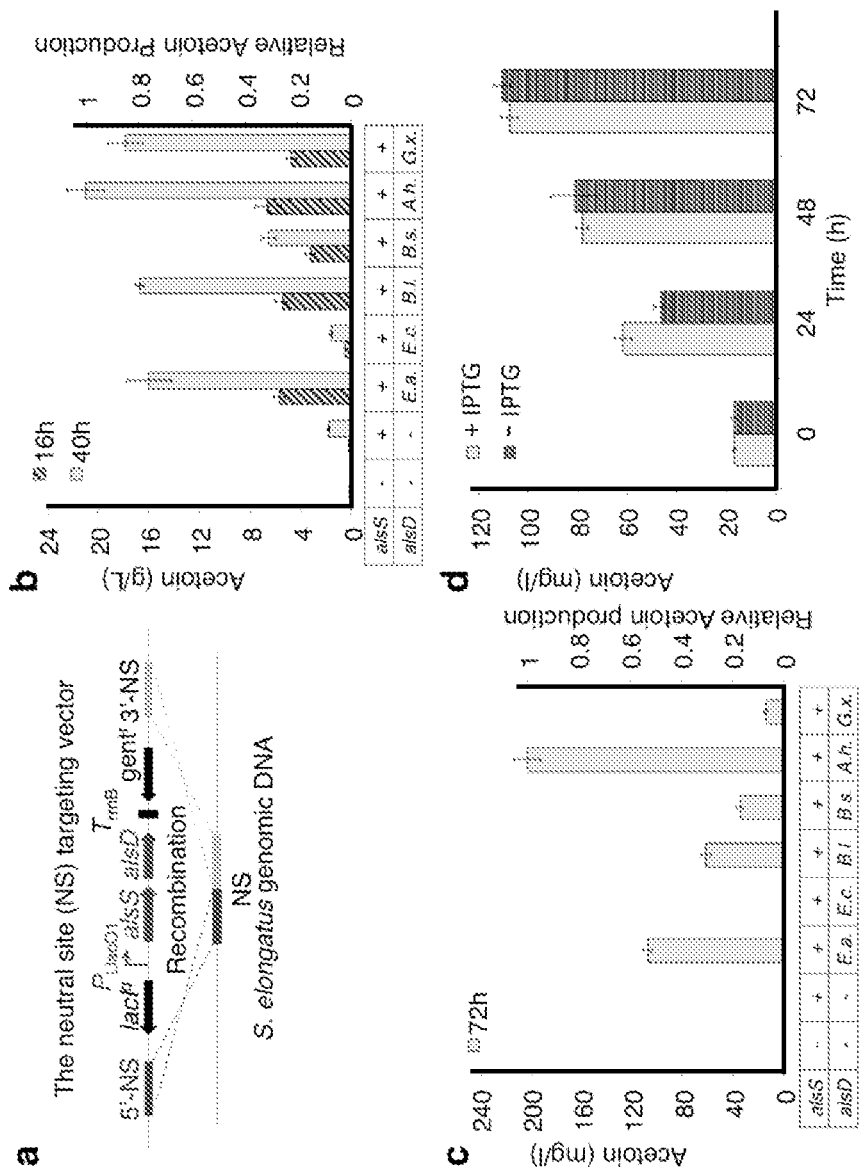
FIG. 3A provides a schematic representation of recombination to integrate alsS and alsD genes into the *S. elongatus* chromosome.
FIG. 3B shows acetoin production in modified *E. coli* cells grown for 16 h (dark) and 40 h (light).
FIG. 3C shows acetoin production in modified *S. elongatus* cells grown for 72 h. alsS indicates inclusion of (+) alsS (B.s.) or absence of (-) the gene. alsD indicates the source organism for the alsD gene (Table 1).
FIG. 3D shows the Effect of IPTG (1 mM) on the production of acetoin in *S. elongatus* containing alsS (B.s.) and alsD (E. a.) under $P_{LlacO1}$. Error bars indicate s.d. (n=3).

To test acetoin production each alsD gene was overexpressed with alsS (B. s.) under the isopropylβ-D-thiogalactoside (IPTG) inducible promoter $P_{LlacO1}$ (35) in E. coli. The cells were cultured in modified M9 medium, containing 50 g/L of glucose, at 30° C. for 16 and 40 h. A control strain expressing only alsS (B. s.) produced 0.2 g/L acetoin indicating that 2-acetolactate decomposes to acetoin in small amounts, which is consistent with previous observations (36-37). When alsD was coexpressed more than 20 g/L of acetoin was produced indicating that autodecarboxylation is not a major contributor to 2-acetolactate conversion (FIG. 3B). All ALDC except that from Enterobacter cloacae (E. c.) were active in E. coli, and displayed a pattern of activity that was consistent through 16 h and 40 h of production (FIG. 3B). The strain expressing alsD from Aeromonas hydrophila (A. h.) was the highest producer (21.0 g/L) followed by the strains expressing alsD from Gluconacetobacter xylinus (G. x.)(17.8 g/L), alsD from Bacillus licheniformis (B. l.)(16.7 g/L) and alsD from Enterobacter aerogenes (E. a.)(16.0 g/L)(FIG. 3B). The strain expressing codon optimized alsD (B. s.), which is the natural gene partner to the alsS (B. s.) used in the production operon, produced the least acetoin (6.6 g/L) which demonstrates that native pathways do not necessarily maintain their integrity when transferred to new hosts. Thus screening of multiple candidates revealed the optimal genes for pathway optimization in each new host (FIG. 3B).

Acetoin production in S. elongatus from $CO_2$. Following our screening strategy for pathway optimization ALDC activity was compared in the photosynthetic cell environment of S. elongatus, based on production of acetoin during heterologous alsS and alsD expression. Each strain was cultured in 125 ml shake flasks with 25 ml BG-11 containing 50 mM $NaHCO_3$ in constant light (55 $\mu Es^{-1}$ $m^{-2}$) at 30 ° C. for 72 h (FIG. 3C). Strains expressing alsD from E. a., B. l., B. s., A. h., and G. x., produced 108 mg/L, 62 mg/L, 35 mg/L, 203 mg/L, and 14 mg/L respectively (FIG. 3C). Control strains, and the strain expressing alsD (E. c.) did not produce a measureable amount of acetoin in this host. Based on these results, we had two alsD genes (from E. a. and A. h.) capable of moderate and high production of acetoin respectively in S. elongatus. To avoid excessive acetoin toxicity we chose alsD (E. a.) as a starting point for sADH analysis.

In order to have an inducible expression system, lacI$^q$, which encodes the E. coli lac repressor, was cloned upstream of $P_{LlacO1}$ (FIG. 3A). The efficiency of LacI repression in the S. elongatus strain containing alsS (B. s) and alsD (E. a.) was investigated by testing acetoin production with or without 1 mM of IPTG (FIG. 3D). Interestingly, acetoin production without IPTG was similar to that with 1 mM IPTG (FIG. 3D), suggesting that $P_{LlacO1}$ was not repressed well by LacI in this construct. The promoter and coding region of lacI$^q$ were verified by Sanger sequencing. This phenomena has been reported with other IPTG-inducible promoters in S. elongatus PCC7942 (38-39) and Synechocystis sp. PCC6803 (40).

Constructing the 23BD biosynthetic pathway. Acetoin can be reduced by a secondary alcohol dehydrogenase (sADH) to produce 23BD (FIG. 1). Identification of strong sADH candidates followed the same method used for ALDC, but in addition to low oxygen sensitivity, two more criteria were added. First, we limited our search to NADPH-dependent sADH as this cofactor is expected to have higher bioavailability during photosynthesis (22). Second, reduction of acetoin by sADH is a diastereoselective reaction, allowing us to choose enzymes to install either an R or S stereocenter. Two NADPH utilizing sADH with R-installing reaction sites had been characterized previously in E. coli (41). The availability of sADH with S-installing reaction sites and NADPH as a cofactor, however, was limited. In the end we chose four adh genes, two with R-installing reaction sites, two with S-installing reaction sites (Table 4). Plasmids were constructed harboring alsS (B. s.), alsD (E. a.) and each of the four adh under $P_{LlacO1}$(FIG. 4A).

Figure 4:
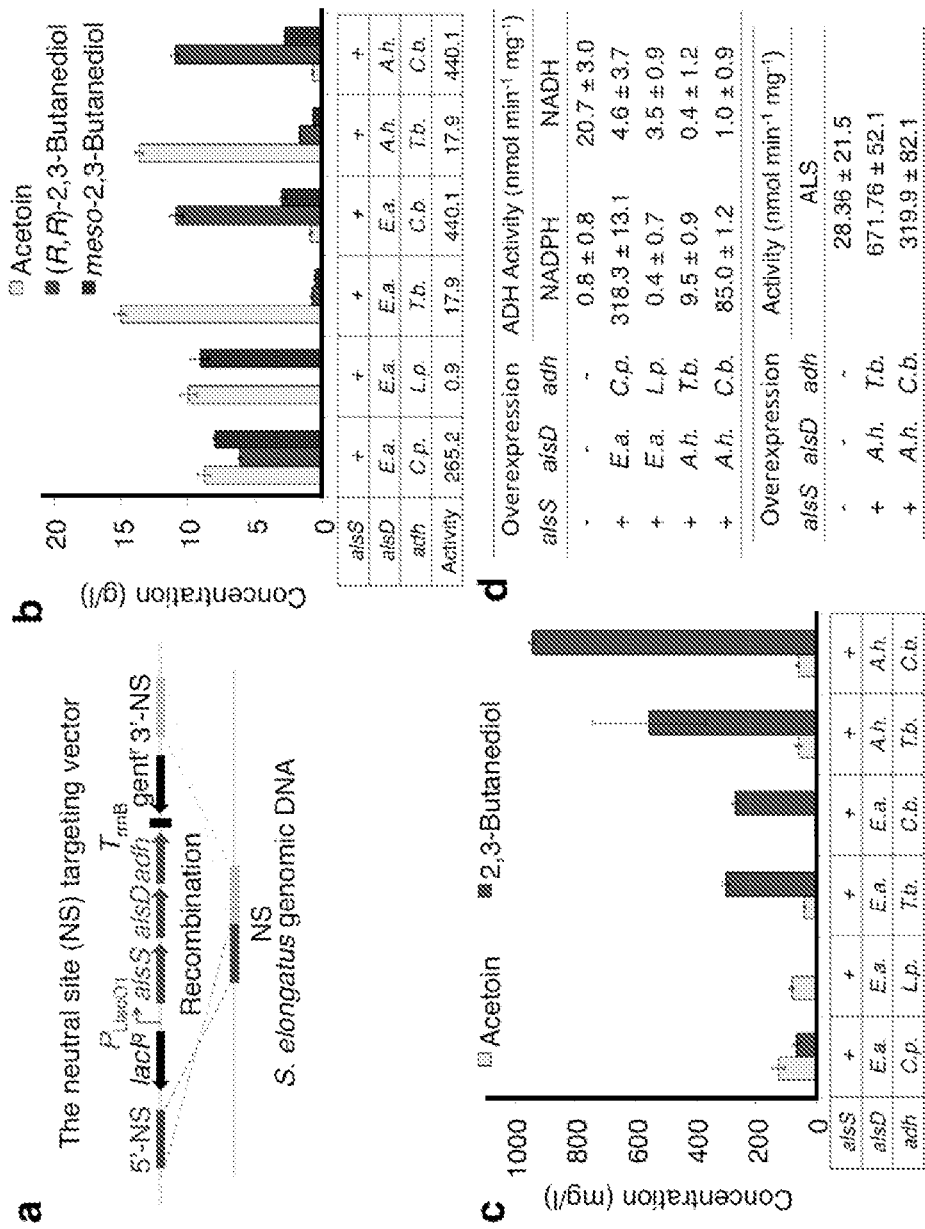
FIG. 4A provides a schematic representation of recombination to integrate alsS, alsD, and adh genes into the *S. elongatus* chromosome.
FIG. 4B shows acetoin production in modified *E. coli* cells were grown for 40 hours. Light bars show acetoin, while dark bars show butanediol (middle bars: meso-23BD, right bars: (R,R)-23BD). alsS indicates inclusion of (+) alsS (B.s.). alsD and adh rows indicate the source organism for the gene (Table 1). Activity is that of sADH expressed in *E. coli* and measured in cell extract (nmol NADPH $min^{-1}$ $mg^{-1}$).
FIG. 4C shows 23BD production in modified *S. elongatus* cells grown for 72 h.
FIG. 4D shows specific activities of ALS and ADH in cell extracts from modified *S. elongatus* strains. Error bars indicate standard deviation.

The resulting E. coli strains were cultured in modified M9 medium, containing 50 g/L glucose, at 30° C. for 40 h (FIG. 4B). The concentration of acetoin remained high for three out of the four strains indicating that sADH activity is limiting in this cell environment. The fourth strain, expressing adh (C. b.), maintained a relatively low acetoin concentration (less than 6% of total production) and produced 13.8 g/L total 23BD as a mixture of (R,R)-23BD and meso-23BD stereoisomers forming 74% and 21% of total production respectively (FIG. 4B). The strains expressing adh (T. b.) and adh (C. p.) produced 2.4 g/L and 14.2 g/L 23BD respectively with both isomers formed in roughly equal amounts in each. High stereoselectivity was achieved in the strain expressing adh (L. p.), which produced 9.1 g/L meso-23BD exclusively. Enzyme activities measured from crude cell lysate isolated during production were high for both sADH (C. p.) and sADH (C. b.), at 265 and 440 nmol min$^{-1}$ mg$^{-1}$ respectively, when excess substrate was used (FIG. 4B). However for the strain expressing adh (C. p.), accumulation of acetoin in the supernatant during production indicates that the enzyme turnover rate at the substrate concentrations present within the cell is slower than the rate of secretion. Relatively low activity of sADH (T. b.) was consistent with accumulation of acetoin in the strain indicating that sADH activity is a bottleneck for production in this E. coli strain (FIG. 4B). The major 23BD product of each of the adh expressing strains matched the stereochemistry predicted by previous characterization (41-43).

23BD production in S. elongatus from $CO_2$. To screen the differences in 23BD productivity in S. elongatus, each of the plasmids used for 23BD production in E. coli was used for transformation of S. elongatus. The engineered strains were cultured in 125 ml baffled shake flasks with 25 ml BG-11 containing 50 mM NaHCO$_3$ in constant light (55 µEs$^{-1}$ m$^{-2}$) at 30° C.

23BD production was detected in three out of four *S. elongatus* strains (FIG. 4C). Measurement of sADH performance in *S. elongatus* was made by comparison of acetoin and 23BD concentrations after 72 hours of growth, using the less active ALDC (E. a.) to lower toxicity in cases when acetoin conversion was low. The strain expressing adh (T. b.) produced 301 mg/L (R,R)-23BD with trace amounts of meso-23BD but also allowed for accumulation of acetoin (FIG. 4C). The strain expressing adh (C. b.) produced 270 mg/L (R,R)-23BD (major) and undetectable levels of acetoin, indicating high flux through the intermediate. The strain expressing adh (C. p.) produced 65 mg L$^{-1}$ 23BD, with meso-23BD as the primary product and accumulated toxic levels of acetoin. The remaining S-installing adh (L. p.) was not active in *S. elongatus*, resulting only in accumulation of acetoin. Enzyme activities measured in crude cell lysate isolated during production showed a roughly 10-fold higher activity for adh (C. b.) than for adh (T. b.), 56.3 and 6.3 nmol min$^{-1}$ mg$^{-1}$ respectively, which could explain the accumulation of acetoin in the less active strain (FIGS. 4C and 4D). Activity for adh (C. p.) was roughly 5-fold higher again than adh (C. b.), however low production and acetoin accumulation was observed, similar to the result in *E. coli*. Enzyme activity could not be detected for the strain expressing adh (L. p.), indicating that the sADH enzyme is responsible for lack of production (FIGS. 4C and 4D). The two sADH with highest production and lowest acetoin accumulation were further tested with the stronger ALDC gene alsD (A. h.). Both strains increased production, yielding 568 mg L$^{-1}$ from adh (T. b.) and 952 mg L$^{-1}$ from adh (C. b.), the latter of which is 3 fold higher than production with alsD (E. a.) over 72 hours (FIG. 4C). Both strains also showed increased acetoin concentrations, although neither reached toxic levels, accumulating 59 mg L$^{-1}$ and 61 mg L$^{-1}$ respectively.

Figure 5:
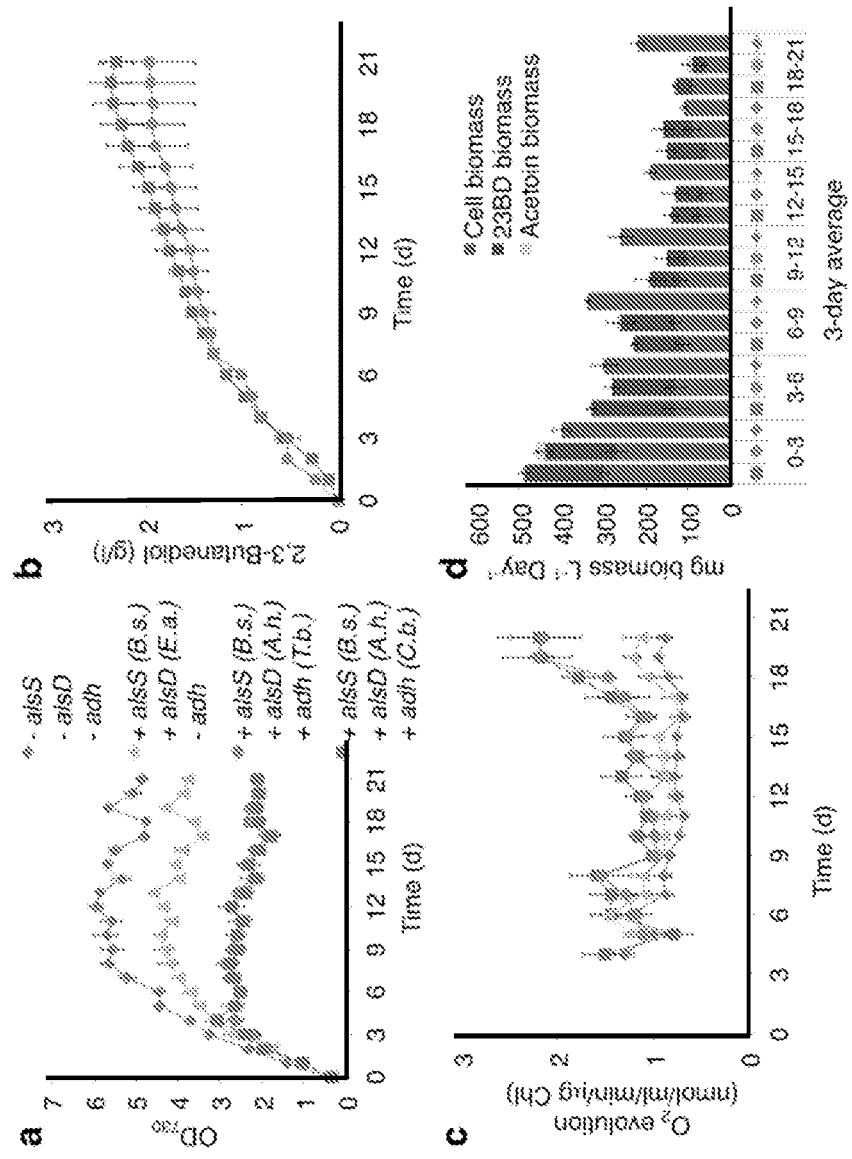
FIG. 5 provides a summary of long-term 2,3-butanediol production by recombinant *S. elongatus* in continuous cultures. Squares: *S. elongatus* containing alsS (B. s.), alsD (A. h.) and adh (C. b.). Circles: *S. elongatus* containing alsS (B. s.), alsD (A. h.) and adh (T. b.). Triangles: *S. elongatus* containing alsS (B. s.) and alsD (E. a.). Diamonds: *S. elongatus* without alsS, alsD or adh.

Long-term production of 23BD in *S. elongatus*. The stability of the highest producing strains was verified by maintaining continuous production in 25 ml cultures at 30° C. in the presence of constant light. The strain containing adh (C. b.) reached a total yield of 2.38 g/L (R,R)-23BD and a maximum production rate of 9847 µg L$^{-1}$ h$^{-1}$ (3 day average)(FIG. 5B). Production was sustained for 21 days. The strain containing adh (T. b.), showed similar results, reaching a total yield of 1.97 g L$^{-1}$, maximum production rate of 7757 µg L$^{-1}$ h$^{-1}$ (3 day average), and sustaining production for 21 days (FIG. 5B). After 21 days, production in both cultures dropped off sharply and was not restored when cells were resuspended in fresh medium, indicating that changes in the culture population such as spontaneous mutations, which restore flux to metabolism, fundamentally impair production over time. Strains containing the 23BD biosynthetic pathway showed reduced growth compared to control strains, as expected mirroring the rate of carbon redirection from central metabolism (FIGS. 5A, 5B and 5D). A second control strain containing only alsS (B. s.) and alsD (E. a.) produced acetoin up to toxic levels after the stationary phase was reached and showed impaired growth beyond what is attributable to carbon redirection.

Evaluating the photosynthetic efficiency of production strains. Evolution of O$_2$ from illuminated cells during continuous production was measured to verify whether the 23BD overproduction pathway could affect the photosynthetic system (FIG. 5C). Both strains expressing the 23BD biosynthetic pathway displayed a slightly higher rate of O$_2$ evolution per µg of chlorophyll compared to control strains (FIG. 5C). This rate increased during late stages of production. Both control strains, each with no production pathway, or only the acetoin production pathway expressed, displayed similar rates of O$_2$ evolution (FIG. 5C). This trend follows the amount of fixed carbon diverted away from central metabolism, indicating that the burden placed on the cell by overproduction could stimulate a positive effect on the cells photosynthetic efficiency (FIGS. 5C and 5D).

CONCLUSIONS

As described herein for the first time, production of 23BD and acetoin directly from CO$_2$ and light was accomplished through engineering of the cyanobacterium, *S. elongatus*. Pathway design was approached so as to match the production pathway to a photosynthetic host. Engineered strains achieved a production rate of 9847 µg l$^{-1}$ h$^{-1}$ and final titer of 2.4 g l$^{-1}$, with sustained production lasting for 21 days. These values, achieved during continuous production from CO$_2$ and light, compare favorably with other studies. The rate is 1.6 fold higher than that for isobutyraldehyde (6,230 µg l$^{-1}$ h$^{-1}$), and significantly higher than other products overproduced from exogenous pathways (FIG. 7). The percentage of biomass produced as 23BD ranges from 30% to 60% (FIG. 5D), which compares favorably to the maximum of 80% achieved during endogenous sucrose overproduction (38).

Figure 6:
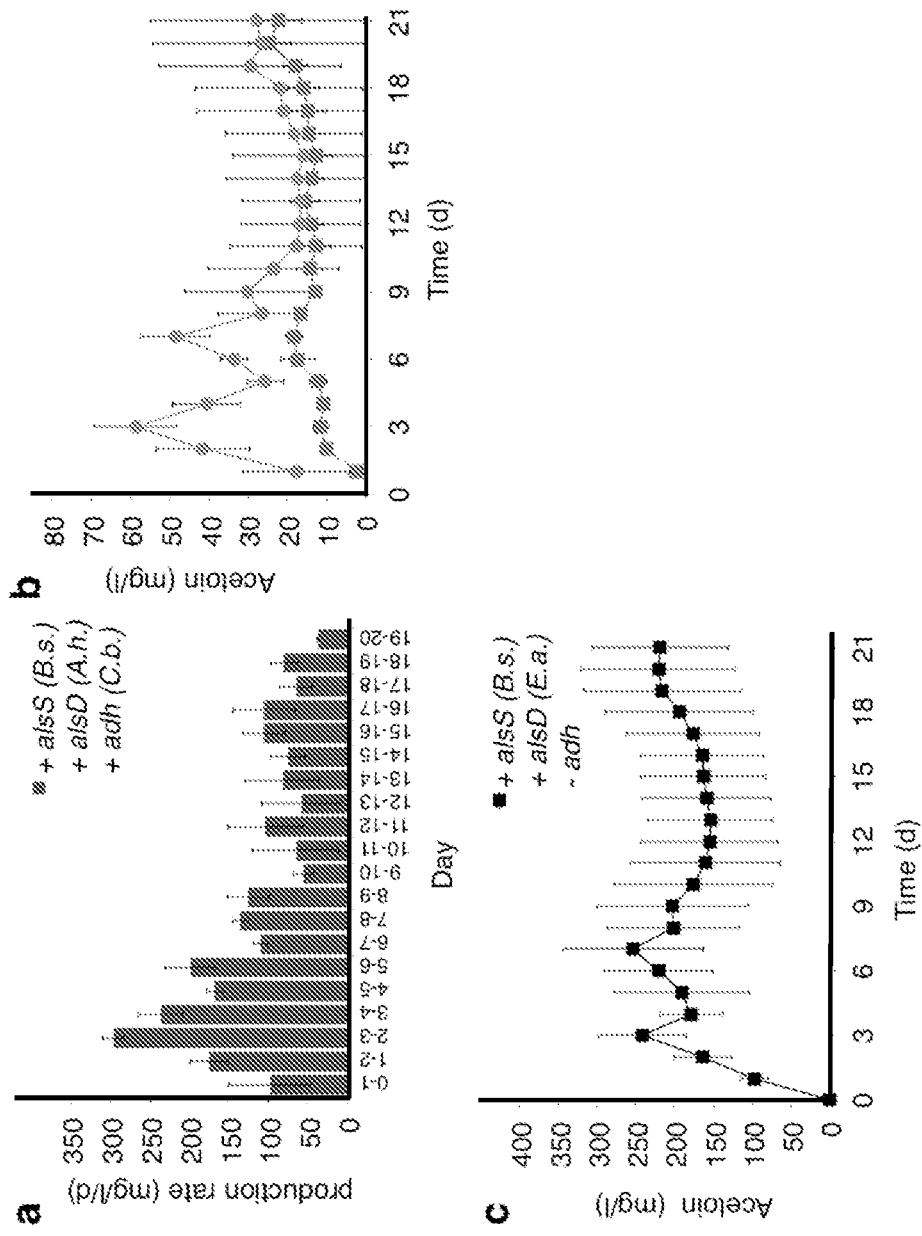
FIG. 6A shows daily 2,3-butanediol production by AL757 (with integrated alsS, alsD (A. h.), and adh (C. b.)).
FIG. 6B shows acetoin concentration during long-term 23BD production experiments. Squares: AL757 (with integrated alsS (B. s.), alsD (A. h.) and adh (C. b.)). Circles: AL756 (with integrated alsS (B. s.), alsD (A. h.) and adh (T. b.)).
FIG. 6C shows long-term acetoin production by AL763 (with integrated alsS and alsD (E. a.)).

To construct the 23BD pathway, low toxicity was a priority for improved culture sustainability and thus commodity chemical production in *S. elongatus*. The negative effect of toxicity on pathway flux is reinforced by low production of acetoin, which is toxic above 0.1 g/L in *S. elongatus* (FIG. 2A), from the 23BD pathway without coexpression of adh (FIG. 6C). Addition of a strong adh to the operon to convert acetoin to 23BD increases total production of the pathway 10-fold (FIGS. 5B and 6C), even though reduction by Adh is not an irreversible step, while production of acetoin is. Thus matching genes to their host provides a means for optimizing pathway function. All genes were screened for production in *E. coli* concurrently with cyanobacteria using identical operons. The patterns of production exhibited by the genes were different between hosts. The productivities of strains expressing alsD (B.l. ) and alsD (G. x. ) in *S. elongatus* were much lower (30% and 7% of top production respectively)(FIG. 3C), than strains overexpressing the same genes in *E. coli* (80% and 85% of top production respectively)(FIG. 3B). Conversely sADH (T. b.), which displayed severely attenuated production in *E. coli* achieved significant production in *S. elongatus*. Additionally the enzyme encoded by adh (L. p.) was entirely inactive in *S. elongatus* despite production of 9.1 g/L meso-23BD in *E. coli*.

Using 23BD production as a model system allowed for inclusion of stereoselectivity as part of the pathway design (FIG. 1). Chirality can be costly to install in chemical synthesis; however biological control offers a much simpler route to these products. In all known cases in nature, acetoin is generated from 2-acetolactate containing an R-stereocenter resulting in (S,S)-23BD not being observed. However autodecarboxylation of 2-acetolactate, or enolate racemization of acetoin, could possibly form (S)-acetoin in the cell and result in (S,S)-23BD production in the presence of S-installing sADH enzymes. Two pathways were designed, one for each stereoisomer (Table 4). In *S. elongatus* both R-installing strains tested in long-term production consistently produced (R,R)-23BD as the major product, although a trace amount of meso-23BD was observed in production by the strain expressing adh (T. b.). Additionally the strain expressing adh (C. p.), which produced mixed isomers in *E. coli*, produced only meso-23BD in *S. elongatus*. In this study no production of (S,S)-23BD was detected, indicating that degradation products do not contribute significantly to the pathway.

During long-term production, evolution of $O_2$ per µg of chlorophyll increased in production strains relative to a control containing the recombination cassette but no alsS, alsD, or adh genes (FIG. 6C). This indicates that the stress imposed on metabolism by production elicits an increase in photosynthetic efficiency. Chlorophyll and $O_2$ production have been seen to increase in roughly equal amounts during similar overproduction of sucrose in engineered *S. elongatus*. Defining the engineering principles for photosynthetic organisms is an important landmark in the search for sustainable technologies. Biological production of 23BD by heterotrophic microbes has attracted attention for many years because of the existence of natural fermentative producers, and the chemical's potential as a versatile carbon feedstock for plastics, solvents, and fuel. The biosynthetic production rate and titer achieved using the tools of the present disclosure mark a large increase in cyanobacterial yields.

REFERENCES

1. McFarlane J & Robinson S (2007) Survey of Alternative Feedstocks for Commodity Chemical Manufacturing. Oak Ridge National Laboratory.
2. Serferlein K E (2008) Annual Energy Review (E.I Administration).
3. Raupach M R, et al. (2007) Global and regional drivers of accelerating CO2 emissions. Proc Natl Acad Sci USA 104(24): 10288-10293.
4. Herzog H & Golomb D (2004) In Encyclopedia of Energy. Edited by Cleveland C J. New York. 277-287.
5. Ruffing A M (2011) Engineered cyanobacteria: teaching an old bug new tricks. Bioeng Bugs 2(3):136-149.
6. Machado I M & Atsumi S (2012) Cyanobacterial biofuel production. J Biotechnol doi:10.1016/j.jbiotec.2012.03.005.
7. Ducat D C, Way J C, & Silver P A (2011) Engineering cyanobacteria to generate high-value products. Trends Biotechnol 29(2):95-103.
8. Scharlemann J P & Laurance W F (2008) Environmental science. How green are biofuels? Science 319 (5859):43-44.
9. Field C B, Behrenfeld M J, Randerson J T, & Falkowski P (1998) Primary production of the biosphere: integrating terrestrial and oceanic components. Science 281 (5374):237-240.
10. Golden S S, Brusslan J, & Haselkorn R (1987) Genetic engineering of the cyanobacterial chromosome. Methods Enzymol 153:215-231.
11. Heidorn T, et al. (2011) Synthetic biology in cyanobacteria engineering and analyzing novel functions. Methods Enzymol 497:539-579.
12. Huang H H, Camsund D, Lindblad P, & Heidorn T (2010) Design and characterization of molecular tools for a Synthetic Biology approach towards developing cyanobacterial biotechnology. Nucleic Acids Res 38(8):2577-2593.
13. Keasling J D (2008) Synthetic biology for synthetic chemistry. ACS Chem Biol 3(1):64-76.
14. Atsumi S, Higashide W, & Liao J C (2009) Direct photosynthetic recycling of carbon dioxide to isobutyraldehyde. Nat Biotechnol 27(12):1177-1180.
15. Lan E I & Liao J C (2012) ATP drives direct photosynthetic production of 1-butanol in cyanobacteria. Proc Natl Acad Sci USA 109(16):6018-6023.
16. Takahama K, Matsuoka M, Nagahama K, & Ogawa T (2003) Construction and analysis of a recombinant cyanobacterium expressing a chromosomally inserted gene for an ethylene-forming enzyme at the psbAI locus. J Biosci Bioeng 95(3):302-305.
17. Lindberg P, Park S, & Melis A (2010) Engineering a platform for photosynthetic isoprene production in cyanobacteria, using Synechocystis as the model organism. Metab Eng 12(1):70-79.
18. Zhou J, Zhang H, Zhang Y, Li Y, & Ma Y (2012) Designing and creating a modularized synthetic pathway in cyanobacterium Synechocystis enables production of acetone from carbon dioxide. Metab Eng 14(4): 394-400.
19. Liu X, Sheng J, & Curtiss R, 3rd (2011) Fatty acid production in genetically modified cyanobacteria. Proc Natl Acad Sci USA 108(17):6899-6904.
20. Tan X, et al. (2011) Photosynthesis driven conversion of carbon dioxide to fatty alcohols and hydrocarbons in cyanobacteria. Metab Eng 13(2):169-176.
21. Shen C R, et al. (2011) Driving forces enable high-titer anaerobic 1-butanol synthesis in *Escherichia coli*. Appl Environ Microbiol 77(9): 2905-2915.
22. Lan E I & Liao J C (2011) Metabolic engineering of cyanobacteria for 1-butanol production from carbon dioxide. Metab Eng 13(4):353-363.
23. Bond-Watts B B, Bellerose R J, & Chang M C (2011) Enzyme mechanism as a kinetic control element for designing synthetic biofuel pathways. Nat Chem Biol 7(4):222-227.
24. Tran A V & Chambers R P (1987) The dehydration of fermentative 2,3-butanediol into methyl ethyl ketone. Biotechnol Bioeng 29(3):343-351.
25. van Haveren J, Scott E L, & Sanders J (2008) Bulk chemicals from biomass. Biofuels Bioprod Bioref 2:41-57.
26. Syu M J (2001) Biological production of 2,3-butanediol. Appl Microbiol Biotechnol 55(1):10-18.
27. Ji X J, Huang H, & Ouyang P K (2011) Microbial 2,3-butanediol production: a state-of-the-art review. Biotechnol Adv 29(3):351-364.
28. Celinska E & Grajek W (2009) Biotechnological production of 2,3-butanediol-current state and prospects. Biotechnol Adv 27(6):715-725.
29. Wijffels R H & Barbosa M J (2010) An outlook on microalgal biofuels. Science 329(5993):796-799.
30. Greenwell H C, Laurens L M, Shields R J, Lovitt R W, & Flynn K J (2010) Placing microalgae on the biofuels priority list: a review of the technological challenges. J R Soc Interface 7(46):703-726.
31. Eiteman M A & Gainer J L (1989) In situ extraction versus the use of an external column in fermentation. Appl Microbiol Biotechnol 30:614-618.
32. Blankenship R E (2002) Carbon Metabolism. Molecular Mechanisms of Photosynthesis, (Blackwell Science Ltd), pp 172-203.
33. Atsumi S, Hanai T, & Liao J C (2008) Non-fermentative pathways for synthesis of branched-chain higher alcohols as biofuels. Nature 451(7174):86-89.

34. Scheer M, et al. (2011) BRENDA, the enzyme information system in 2011. Nucleic Acids Res. 39:D670-676.
35. Lutz R & Bujard H (1997) Independent and tight regulation of transcriptional units in *Escherichia coli* via the LacR/O, the TetR/O and AraC/I1-I2 regulatory elements. Nucleic Acids Res 25(6):1203-1210.
36. Aristidou A A, San K Y, & Bennett G N (1994) Modification of central metabolic pathway in *escherichia coli* to reduce acetate accumulation by heterologous expression of the *bacillus subtilis* acetolactate synthase gene. Biotechnol Bioeng 44(8):944-951.
37. Park H S, Xing R, & Whitman W B (1995) Nonenzymatic acetolactate oxidation to diacetyl by flavin, nicotinamide and quinone coenzymes. Biochim Biophys Acta 1245(3):366-370.
38. Ducat D C, Avelar-Rivas J A, Way J C, & Silver P A (2012) Rerouting carbon flux to enhance photosynthetic productivity. Appl Environ Microbiol 78(8): 2660-2668.
39. Mutsuda M, Michel K P, Zhang X, Montgomery B L, & Golden S S (2003) Biochemical properties of CikA, an unusual phytochrome-like histidine protein kinase that resets the circadian clock in *Synechococcus elongatus* PCC 7942. J Biol Chem 278(21):19102-19110.
40. Ng W O, Zentella R, Wang Y, Taylor J S, & Pakrasi H B (2000) PhrA, the major photoreactivating factor in the cyanobacterium *Synechocystis* sp. strain PCC 6803 codes for a cyclobutane-pyrimidine-dimer-specific DNA photolyase. Arch Microbiol 173(5-6):412-417.
41. Yan Y, Lee C C, & Liao J C (2009) Enantioselective synthesis of pure (R,R)-2,3-butanediol in *Escherichia coli* with stereospecific secondary alcohol dehydrogenases. Org Biomol Chem 7(19):3914-3917.
42. Zhang R, et al. (2008) Crystal structure of a carbonyl reductase from Candida parapsilosis with anti-Prelog stereospecificity. Protein Sci 17(8):1412-1423.
43. Rattray F P, Walfridsson, M.' Nilsson, D. (2000) Purification and characterization of a diacetyl reductase from *Leuconostoc paseudomesenteroides*. International Dairy Journal 10.
44. Najmudin S, et al. (2003) Purification, crystallization and preliminary X-ray crystallographic studies on acetolactate decarboxylase. Acta Crystallogr D Biol Crystallogr 59(Pt 6):1073-1075.
45. Rippka R D, J.; Waterbury, J. B.; Herdman. M. Stainer, R. Y (1979) Generic Assignments, Strain Histories and Properties of Pure Cultures of Cyanobacteria. Journal of General Microbiology 111:1-61.
46. Voges O. Proskauer, B. (1898) Beitraege zur Ernaehrungsphysiologie und zur Differential Diagnose der Bakterien der hemmorrhagischen Septicamie. Z. Hyg. 28.
47. Westerfeld W W (1945) A colorimetric determination of blood acetoin. J Biol Chem 161:495-502.
48. Godtfredsen S E, Lorck H, & Sigsgaard P (1983) On the occurrence of a-acetolactate decarboxylases among microorganims. Carlsberg Res, Commun. 48:239-247.
49. Dexter J & Pengcheng F (2009) Metabolic engineering of cyanobacteria for ethanol production. Energy & Environ. Sci. 2:857-864.
50. Li M Z & Elledge S J (2007) Harnessing homologous recombination in vitro to generate recombinant DNA via SLIC. Nat Methods 4(3):251-256.
51. Lutz R & Bujard H (1997) Independent and tight regulation of transcriptional units in *Escherichia coli* via the LacR/O, the TetR/O and AraC/I1-I2 regulatory elements. Nucleic Acids Res 25(6):1203-1210.
52. Atsumi S, Hanai T, & Liao J C (2008) Non-fermentative pathways for synthesis of branched-chain higher alcohols as biofuels. Nature 451(7174):86-89.
53. Golden S S, Brusslan J, & Haselkorn R (1987) Genetic engineering of the cyanobacterial chromosome. Methods Enzymol 153:215-231.
54. Yang Y T, Peredelchuk M, Bennett G N, & San K Y (2000) Effect of variation of Klebsiella pneumoniae acetolactate synthase expression on metabolic flux redistribution in *Escherichia coli*. Biotechnol Bioeng 69(2):150-159.
55. Atsumi S, Higashide W, & Liao J C (2009) Direct photosynthetic recycling of carbon dioxide to isobutyraldehyde. Nat Biotechnol 27(12):1177-1180.
56. Liu X, Sheng J, & Curtiss R, 3rd (2011) Fatty acid production in genetically modified cyanobacteria. Proc Natl Acad Sci USA 108(17):6899-6904.
57. Dexter J & Pengcheng F (2009) Metabolic engineering of cyanobacteria for ethanol production. Energy & Environ. Sci. 2:857-864.
58. Zhou J, Zhang H, Zhang Y, Li Y, & Ma Y (2012) Designing and creating a modularized synthetic pathway in cyanobacterium *Synechocystis* enables production of acetone from carbon dioxide. Metab Eng 14(4): 394-400.
59. Takahama K, Matsuoka M, Nagahama K, & Ogawa T (2003) Construction and analysis of a recombinant cyanobacterium expressing a chromosomally inserted gene for an ethylene-forming enzyme at the psbAI locus. J Biosci Bioeng 95(3):302-305.
60. Lan E I & Liao J C (2012) ATP drives direct photosynthetic production of 1-butanol in cyanobacteria. Proc Natl Acad Sci USA 109(16):6018-6023.
61. Tan X, et al. (2011) Photosynthesis driven conversion of carbon dioxide to fatty alcohols and hydrocarbons in cyanobacteria. Metab Eng 13(2):169-176.

SEQUENCES

SEQ ID NO: 1: PLlacO1 promoter
AATTGTGAGCGGATAACAATTGACATTGTGAGCGGATAACAAGATACTGAGCACATCAGCAGGACGCA
CTGACC SEQ ID NO: 2: *Bacillus subtilis* acetolactate synthase- alsS gene
nucleotide sequence
ATGTTGACAAAAGCAACAAAAGAACAAAAATCCCTTGTGAAAAACAGAGGGGCGGAGCTTGTTGTTGA
TTGCTTAGTGGAGCAAGGTGTCACACATGTATTTGGCATTCCAGGTGCAAAAATTGATGCGGTATTTG
ACGCTTTACAAGATAAAGGACCTGAAATTATCGTTGCCCGGCACGAACAAAACGCAGCATTCATGGCC
CAAGCAGTCGGCCGTTTAACTGGAAAACCGGGAGTCGTGTTAGTCACATCAGGACCGGGTGCCTCTAA
CTTGGCAACAGGCCTGCTGACAGCGAACACTGAAGGAGACCCTGTCGTTGCGCTTGCTGGAAACGTGA
TCCGTGCAGATCGTTTAAAACGGACACATCAATCTTTGGATAATGCGGCGCTATTCCAGCCGATTACA

```
AAATACAGTGTAGAAGTTCAAGATGTAAAAAATATACCGGAAGCTGTTACAAATGCATTTAGGATAGC
GTCAGCAGGGCAGGCTGGGGCCGCTTTTGTGAGCTTTCCGCAAGATGTTGTGAATGAAGTCACAAATA
CGAAAAACGTGCGTGCTGTTGCAGCGCCAAAACTCGGTCCTGCCAGCAGATGATGCAATCAGTGCGGCC
ATAGCAAAAATCCAAACAGCAAAACTTCCTGTCGTTTTGGTCGGCATGAAAGGCGGAAGACCGGAAGC
AATTAAAGCGGTTCGCAAGCTTTTGAAAAAGGTTCAGCTTCCATTTGTTGAAACATATCAAGCTGCCG
GTACCCTTTCTAGAGATTTAGAGGATCAATATTTTGGCCGTATCGGTTTGTTCCGCAACCAGCCTGGC
GATTTACTGCTAGAGCAGGCAGATGTTGTTCTGACGATCGGCTATGACCCGATTGAATATGATCCGAA
ATTCTGGAATATCAATGGAGACCGGACAATTATCCATTTAGACGAGATTATCGCTGACATTGATCATG
CTTACCAGCCTGATCTTGAATTGATCGGTGACATTCCGTCCACGATCAATCATATCGAACACGATGCT
GTGAAAGTGGAATTTGCAGAGCGTGAGCAGAAAATCCTTTCTGATTTAAAACAATATATGCATGAAGG
TGAGCAGGTGCCTGCAGATTGGAAATCAGACAGAGCGCACCCTCTTGAAATCGTTAAAGAGTTGCGTA
ATGCAGTCGATGATCATGTTACAGTAACTTGCGATATCGGTTCGCACGCCATTTGGATGTCACGTTAT
TTCCGCAGCTACGAGCCGTTAACATTAATGATCAGTAACGGTATGCAAACACTCGGCGTTGCGCTTCC
TTGGGCAATCGGCGCTTCATTGGTGAAACCGGGAGAAAAGTGGTTTCTGTCTCTGGTGACGGCGGTT
TCTTATTCTCAGCAATGGAATTAGAGACAGCAGTTCGACTAAAAGCACCAATTGTACACATTGTATGG
AACGACGACACATATGACATGGTTGCATTCCAGCAATTGAAAAAATATAACCGTACATCTGCGGTCGA
TTTCGGAAATATCGATATCGTGAAATATGCGGAAAGCTTCGGAGCAACTGGCTTGCGCGTAGAATCAC
CAGACCAGCTGGCAGATGTTCTGCGTCAAGGCATGAACGCTGAAGGTCCTGTCATCATCGATGTCCCG
GTTGACTACAGTGATAACATTAATTTAGCAAGTGACAAGCTTCCGAAAGAATTCGGGGAACTCATGAA
AACGAAAGCTCTC

SEQ ID NO: 3: Bacillus subtilis acetolactate synthase- alsS amino
acid sequence
MLTKATKEQKSLVKNRGAELVVDCLVEQGVTHVFGIPGAKIDAVFDALQDKGPEIIVARHEQNAAFMA
QAVGRLTGKPGVVLVTSGPGASNLATGLLTANTEGDPVVALAGNVIRADRLKRTHQSLDNAALFQPIT
KYSVEVQDVKNIPEAVTNAFRIASAGQAGAAFVSFPQDVVNEVTNTKNVRAVAAPKLGPAADDAISAA
IAKIQTAKLPVVLVGMKGGRPEAIKAVRKLLKKVQLPFVETYQAAGTLSRDLEDQYFGRIGLFRNQPG
DLLLEQADVVLTIGYDPIEYDPKFWNINGDRTIIHLDEIIADIDHAYQPDLELIGDIPSTINHIEHDA
VKVEFAEREQKILSDLKQYMHEGEQVPADWKSDRAHPLEIVKELRNAVDDHVTVTCDIGSHAIWMSRY
FRSYEPLTLMISNGMQTLGVALPWAIGASLVKPGEKVVSVSGDGGFLFSAMELETAVRLKAPIVHIVW
NDSTYDMVAFQQLKKYNRTSAVDFGNIDIVKYAESFGATGLRVESPDQLADVLRQGMNAEGPVIIDVP
VDYSDNINLASDKLPKEFGELMKTKAL SEQ ID NO: 4: Enterobacter aerogenes KCTC 2190/ ATCC13048
acetolactate decarboxylase - alsD gene nucleotide sequence
ATGAATCATGCTTCAGATTGCACCTGTGAAGAGAGTCTGTGTGAAACGCTACGCGCGTTTTCCGCTCA
GCATCCCGATAGCGTGCTGTATCAAACTTCGCTGATGAGCGCCCTGCTCAGCGGCGTCTACGAAGGTA
CCACCACCATTGCGGACCTGCTGAAGCACGGTGATTTCGGGCTCGGCACTTTTAATGAACTCGACGGC
GAGCTGATCGCGTTTAGCAGCCAGGTTTATCAACTGCGTGCCGACGGCAGCGCGCGTAAAGCGCGTCC
GGAACAGAAAACGCCGTTTGCGGTGATGACCTGGTTTCAGCCGCAGTACCGTAAAACCTTTGACCATC
CGGTCAGCCGCCAGCAGCTGCATGAGGTTATTGACCAGCAAATTCCTTCCGACAATCTGTTCTGCGCG
CTGCGATCGATGGTCATTTCCGCCACGCCCATACCCGCACCGTGCCTCGTCAGCGCCGCCCTACCG
GGCGATGACCGACGTGCTCGACGATCAGCCGGTTTTCCGCTTTAACCAGCGTGACGGCGTACTGGTCG
GTTTTCGTACCCCGCAGCATATGCAGGGAATTAACGTCGCCGGCTATCACGAACACTTCATTACCGAT
GACCGCCAGGGCGGCGGCCACCTGCTGGACTACCAGCTCGACCATGGGGTATTGACCTTCGGCGAAAT
TCATAAGCTGATGATCGACCTTCCCGCCGACAGCGCGTTCCTGCAGGCCAATTTGCATCCCGATAATC
TCGATGCCGCCATCCGTTCAGTAGAAAGTTAG SEQ ID NO: 5: Enterobacter aerogenes KCTC 2190/ ATCC13048
acetolactate decarboxylase - alsD amino acid sequence
MNHASDCTCEESLCETLRAFSAQHPDSVLYQTSLMSALLSGVYEGTTTIADLLKHGDFGLGTFNELDG
ELIAFSSQVYQLRADGSARKARPEQKTPFAVMTWFQPQYRKTFDHPVSRQQLHEVIDQQIPSDNLFCA
LRIDGHFRHAHTRTVPRQTPPYRAMTDVLDDQPVFRFNQRDGVLVGFRTPQHMQGINVAGYHEHFITD
DRQGGGHLLDYQLDHGVLTFGEIHKLMIDLPADSAFLQANLHPDNLDAAIRSVES SEQ ID NO: 6: Enterobacter cloacae subsp. cloacae ATCC 13047
acetolactate decarboxylase - alsD gene nucleotide sequence
ATGAGCGCCCTGCTAAGCGGTGTCTACGAAGGGGACACCACCATCGCCGATCTGCTGGCACATGGTGA
TTTTGGTCTGGGCACCTTCAACGAGCTGGACGGCGAAATGATTGCCTTCAGCAGCCAGGTGTACCAGC
TGCGCGCCGACGGCAGCGCACGCGCCGCGAAGCCAGAGCAGAAAACGCCGTTCGCGGTGATGACCTGG
TTCCAGCCGCAGTACCGCAAAACCTTTGATGCGCCGGTCAGCCGTCAGCAGATCCACGACGTGATCGA
CCAGCAAATTCCCTCGGATAACCTGTTCTGCGCGCTGCGCATCGACGGCAACTTCCGCCACGCCCACA
CCCGTACCGTACCGCGTCAGACGCCGCCATACCGCGCGATGACCGTGCTGGACGACCAGCCGGTG
TTCCGCTTTAACCAGCGTGAAGGGGTGCTGGTTGGGTTCCGCACGCCGCAGCATATGCAGGGCATCAA
CGTGGCCGGCTATCACGAACATTTCATTACCGACGACCGTCAGGGCGGGGGACATCTGCTGGATTACC
AGCTGGAGAGCGGCGTGCTCACCTTTGGCGAAATACACAAGCTAATGATTGACCTGCCCGCCGACAGC
GCGTTTTTACAGGCCAACCTTCACCCCAGCAACCTTGATGCAGCGATCCGTTCCGTCGAAAACTAA SEQ ID NO: 7: Enterobacter cloacae subsp. cloacae ATCC 13047
acetolactate decarboxylase - alsD amino acid sequence
MSALLSGVYEGDTTIADLLAHGDFGLGTFNELDGEMIAFSSQVYQLRADGSARAAKPEQKTPFAVMTW
FQPQYRKTFDAPVSRQQIHDVIDQQIPSDNLFCALRIDGNFRHAHTRTVPRQTPPYRAMTDVLDDQPV
FRFNQREGVLVGFRTPQHMQGINVAGYHEHFITDDRQGGGHLLDYQLESGVLTFGEIHKLMIDLPADS
AFLQANLHPSNLDAAIRSVEN
```

SEQUENCES

SEQ ID NO: 8: *Bacillus licheniformis* ATCC 14580 acetolactate
decarboxylase - alsD gene nucleotide sequence
ATGAAAAGTGCAAGCAAACAAAAAATAATTCAGCCCGTTGATAAGAACCTCGATCAAGTCTATCAGGT
CTCAACGATGGTATCTTTATTGGACGGAATTTACGACGGGGATTTTTATATGTCCGAAGCGAAGGAGC
ACGGAGACTTCGGGATCGGAACGTTCAACCGGCTCGACGGCGAGCTGATCGGTTTTGACGGTGAGTTT
TACCGTCTCCGTTCCGATGGAAAAGCCTACCCAGTTCAAGGAAGCGATTGTTCTCCATTTTGCTCGCT
GGCTTTCTTCCGGCCGGATATCTATCACGAAATCAAGCAGCGGATTGCCGCTTGAGGCGTCGAAGAAG
AAATGAAACGGATCATGCCGAGTGAAAACCTGTTTTACGCGATTCGCATGGACGGAACCTTTAAGAAA
GTCAAAACGAGAACAGTTGAACTTCAGGAAAAACCGTATGTGCCGATGGTTGATGCGGTAAAATCACA
GCCGATCTTTGATTTTAATGATATTACGGGGACGATCGTCGGCTTTTGGACACCGCAATATGCCAACG
GAATCGCAGTTTCCGGCTTCCATCTTCACTTTATAGATGAAGACCGCAATGTCGGCGGACACGTTTTC
GATTATGAAATCGAAGAATGCACGGTGCAAATTTCTCAAAAACTCAATATGAACCTCAGATTGCCGAA
TACGCAAGATTTCTTTCAAGCGGATTTCAATAAACACGATCTTGCAGCCGGAATTGAAGCGGCCGAAG
GCAATCCCGAGTAA SEQ ID NO: 9: *Bacillus licheniformis* ATCC 14580 acetolactate
decarboxylase - alsD amino acid sequence
MKSASKQKIIQPVDKNLDQVYQVSTMVSLLDGIYDGDFYMSEAKEHGDFIGTFNRLDGELIGFDGEF
YRLRSDGKAYPVQGSDCSPFCSLAFFRPDIYHEIKQRMPLEAFEEEMKRIMPSENLFYAIRMDGTFKK
VKTRTVELQEKPYVPMVDAVKSQPIFDFNDITGTIVGFWTPQYANGIAVSGFHLHFIDEDRNVGGHVF
DYEIEECTVQISQKLNMNLRLPNTQDFFQADFNKHDLAAGIEAAEGNPE SEQ ID NO: 10: *Bacillus subtilis* acetolactate decarboxylase - alsD
gene nucleotide sequence (codon usage is optimized for *S. elongatus*)
ATGAAACGTGAGTCGAACATTCAAGTCTTGAGCCGAGGCCAAAAGGACCAACCAGTCTCCCAGATCTA
CCAAGTGAGCACTATGACAAGTCTCTTGGACGGAGTCTACGATGGCGATTTTGAGCTCTCGGAAATTC
CGAAATATGGGGATTTCGGCATTGGGACCTTTAACAAACTGGACGGTGAACTGATCGGCTTTGATGGT
GAGTTCTACCGCCTGCGCAGTGATGGGACCGCCACGCCGGTTCAAAATGGCGACCGGAGCCCGTTTTG
CAGCTTTACATTCTTCACCCCCGACATGACACACAAGATTGATGCTAAAATGACTCGCGAAGATTTCG
AGAAAGAAATCAATTCGATGTTGCCTAGTCGTAATTTGTTTTATGCCATTCGCATCGACGGTCTGTTT
AAGAAGGTGCAGACCCGCACGGTTGAACTCCAGGAGAAGCCGTACGTTCCTATGGTGGAAGCAGTCAA
GACGCAGCCCATCTTTAACTTCGACAATGTGCGCGGGACCATTGTCGGCTTCCTGACGCCCGTTATG
CGAACGGCATCGCTGTCTCTGGTTACCATCTCCACTTTATCGATGAAGGCCGAAATTCCGGAGGCCAT
GTTTTTGATTATGTGCTCGAAGATTGTACGGTGACCATCAGCCAGAAATGAACATGAACTTGCGGCT
GCCAAATACCGCGGATTTCTTCAATGCAAACCTGGATAACCCCGATTTTGCCAAAGATATTGAAACGA
CTGAGGGTTCTCCCGAGTAG SEQ ID NO: 11: *Bacillus subtilis* acetolactate decarboxylase - alsD
amino acid sequence
MKRESNIQVLSRGQKDQPVSQIYQVSTMTSLLDGVYDGDFELSEIPKYGDFIGTFNKLDGELIGFDG
EFYRLRSDGTATPVQNGDRSPFCSFTFFTPDMTHKIDAKMTREDFEKEINSMLPSRNLFYAIRIDGLF
KKVQTRTVELQEKPYVPMVEAVKTQPIFNFDNVRGTIVGFLTPAYANGIAVSGYHLHFIDEGRNSGGH
VFDYVLEDCTVTISQKMNMNLRLPNTADFFNANLDNPDFAKDIETTEGSPE SEQ ID NO: 12: *Aeromonas hydrophila* acetolactate decarboxylase -
alsD gene nucleotide sequence (codon usage is optimized for *S.
elongatus*)
ATGGAAACTAATAGCTCGTGCGATTGTGCAATCGAAATCTCGCAGCAATTTGCGCGCTGGCAGGCCCG
TCAGGTGGGGGCGAGGTCTACCAGTCCAGCGTGATGTCGGCGGGTGTTTACGAAGGCG
AAACCACAATGGCCGATCTGCTCCGCCACGGGGACTTTGGTCTGGGCACGTTTAACCGGCTGGACGGC
GAACTCATTGCCTTTGAGCGGCAAATCCATCAGTTGAAAGCGGATGGATCTGCCCGACCCGCTCGCGC
AGAACAGAAACGCCGTTTGCCGTGATGACGCACTTCCGGCCGTGCTTGAACGCCGGTTCGCTCATC
CGCTGTCCCGCGAAGAAATTCACCAATGGGTCGATCGCCTCGGTGGGCACTGACAACGTTTTCGTTGCA
TTTCGACTGGATGGCTTGTTTGAGCAAGCGCAGGTCCGCACCGTTCCCCTGTCAGAGCCCACCCTATAA
GCCCATGTTGGAGGCCATTGAAGCCCAGCCTCTGTTCAGTTTCAGTTTGCGGCGTGGGACCCTCGTCG
GCTTTCGCTGCCCACCCTTCGTGCAAGGCATTAACGTGGCTGGCTATCATGAACATTTCATTACCGAG
GATCGCCGAGGTGGGGGTCATATCTTGGATTACGCTATGGGACACGGCCAGCTCCAACTGAGCGTGGT
TCAACACCTCAACATCGAGTTGCCTCGAAATCCTGCCTTTCAACAGGCAGACCTCAATCCGGCGGATC
TGGACCGCGCTATCCGTGCGGCTGAGGGTTAG SEQ ID NO: 13: *Aeromonas hydrophila* acetolactate decarboxylase -
alsD amino acid sequence
METNSSCDCAIEISQQFARWQARQGGGEVYQSSLMSALLAGVYEGETTMADLLRHGDFLGTFNRLDG
ELIAFERQIHQLKADGSARPARAEQKTPFAVMTHFRPCLQRRFAHPLSREEIHQWVDRLVGTDNVFVA
FRLDGLFEQAVRTVPCQSPPYKPMLEAIEAQPLFSFSLRRGTLVGFRCPPFVQGINVAGYHEHFITE
DRRGGHILDYAMGHGQLQLSVVQHLNIELPRNPAFQQADLNPADLDRAIRAAEG SEQ ID NO: 14: *Acetobacter aceti*, ssp. *xylinum*, NBRC 3288
(*Gluconacetobacter xylinus*) acetolactate decarboxylase - alsD gene
nucleotide sequence
ATGGAAATAGGCTTTAATATATATTGGACGTACGAACCTGCCTGCATCACCATTAGTCTGCAATCACA
AATGACCGGGTTGAGGCGATGCCATGTGCCGCATTGTCCCCCGATGCAGGAGACTGAGGTCGTGAAGC
TTAAATGCTACTCGGTAGGGGATGTTGATACCCGGTCCAGCGCTGCTGATTCGACTGGCGTGCGTCCG
CGCATGAACCGCCTGTACCAGACATCGACCATGGCCGCGCTGCTTGATGCGGTCTATGATGGCGAGAC
CACGCTTGATGAACTGCTGATGCACGGCAATTTCGGGCTGGGCACGTTCAACGGCCTTGATGGCGAGA
TGATCGTCAATGACAGCGTAATCCACCAGTTCCGTGCAGACGGGCAGGCCGGTCGTGTGCCGGGCGAC
CTCAGGACTCCGTTCGCCTGCGTTACCTTCTTCAACCCGGAGAAGGAATACATGATCGACACCGCGCA

| SEQUENCES |
| --- |
| GGATAAGGAAGGCTTCGAGGCGATCGTGGATCACCTCGTCAACAATCCCAACCTGTTCGCCGCCGTGC |
| GCTTTACCGGCATGTTCGAGCGGGTCGAGACCCGCACCGTGTTCTGCCAGTGCCAGCCCTACCCACCC |
| ATGCTGGAAGTGGTGGCCCGCCAGCCCACCATGCAGCTTGGCCTCCACCGGCACCATGCTTGGTT |
| CCGCACGCCGGGCTACATGCAGGGCGTGAACGTGGCGGGTTATCACCTGCACTTCCTGACTGAGGACG |
| GACGCCGTGGCGGCCATGTGACCGATTACGGCGTGCTGCGCGGTCGGCTTGAGGTGGGCGTGATTTCC |
| GATGTGGAAATCCAGCTGCCCCGCACCGAACAGTTCGCGCGCGCCAACCTGTCCCCGAAAACATTCA |
| CGAGGCCATTCGCGTGGCCGAGGGCGGCTGA |

SEQ ID NO: 15: *Acetobacter aceti*, ssp. *xylinum*, NBRC 3288
(*Gluconacetobacter xylinus*) acetolactate decarboxylase - alsD amino
acid sequence
MEIGFNIYWTYEPACITISLQSQMTGLRRCHVPHCPPMQETEVVKLKCYSVGDVDTRSSAADSTGVRP
RMNRLYQTSTMAALLDAVYDGETTLDELLMHGNFGLGTFNGLDGEMIVNDSVIHQFRADGQAGRVPGD
LRTPFACVTFFNPEKEYMIDTAQDKEGFEAIVDHLVNNPNLFAAVRFTGMFERVETRTVFCQCQPYPP
MLEVVARQPTMQLGASTGTMLGFRTPGYMQGVNVAGYHLHFLTEDGRRGGHVTDYGVLRGRLEVGVIS
DVEIQLPRTEQFARANLSPENIHEAIRVAEGG SEQ ID NO: 16: *Candida parapsilosis* M203011 alcohol dehydrogenase -
adh gene nucleotide sequence (codon usage is optimized for *S.
elongatus*)
ATGGGGGAGATTGAGTCCTATTGTAACAAAGAGCTAGGTCCCTTACCTACTAAAGCACCGACCCTGTC
CAAAAACGTGCTCGATCTATTCTCCTTGAAGGGAAAGGTGGCTTCGGTGACGGGCAGCAGCGGAGGCA
TTGGTTGGGCCGTAGCCGAAGCATACGCCCAGGCCGGTGCAGACGTCGCGATTTGGTACAACAGCCAT
CCTGCGGACGAGAAGGCGGAACACCTGCAGAAAACTTATGGCGTGCACAGTAAAGCCTATAAGTGCAA
TATCAGTGATCCGAAAAGTGTGGAAGAAACGATCTCACAGCAAGAGAAGGATTTTGGCACGATCGACG
TGTTCGTCGCTAATGCCGGGGTCACTTGGACACAGGGCCCAGAGATCGATGTTGACAACTATGATTCG
TGGAACAAAATCATTAGTGTTGATTTGAATGGCGTTTACTATTGCAGCCACAATATTGGCAAGATCTT
CAAGAAGAATGGGAAAGGTTCTCTGATTATCACGTCGAGTATTTCTGGGAAAATCGTTAACATTCCGC
AGTTGCAAGCGCCCTACAATACCGCGAAGGCCGCGTGTACCCATCTCGCGAAATCGCTCGCCATTGAA
TGGGCTCCGTTTGCACGCGTCAACACGATTAGCCCCGGATACATCGACACCGATATCACCGATTTTGC
CTCTAAAGACATGAAAGCTAAGTGGTGGCAACTTACTCCACTGGGACGGGAAGGCCTCACCCAAGAAC
TGGTCGGCGGCTACTTGTATCTGGCTAGCAATGCTTCGACATTTACCACCGGTTCAGATGTCGTTATC
GATGGCGGTTACACATGCCCC SEQ ID NO: 17: *Candida parapsilosis* M203011 alcohol dehydrogenase -
adh amino acid sequence
MGEIESYCNKELGPLPTKAPTLSKNVLDLFSLKGKVASVTGSSGGIGWAVAEAYAQAGADVAIWYNSH
PADEKAEHLQKTYGVHSKAYKCNISDPKSVEETISQQEKDFGTIDVFVANAGVTWTQGPEIDVDNYDS
WNKIISVDLNGVYYCSHNIGKIFKKNGKGSLIITSSISGKIVNIPQLQAPYNTAKAACTHLAKSLAIE
WAPFARVNTISPGYIDTDITDFASKDMKAKWWQLTPLGREGLTQELVGGYLYLASNASTFTTGSDVVI
DGGYTCP SEQ ID NO: 18: *Leuconostoc pseudomesenteroides* CHCC2114 alcohol
dehydrogenase - adh gene nucleotide sequence (codon usage is
optimized for *S. elongatus*)
ATGACAAAGAAAGTGGCTATGGTGACGGGTGGCGCCCAAGGGATCGGAGAGGCCATTGTGCGACGTTT
GTCGGCAGATGGCTTTGCGGTCGCAGTGGCTGATCTGAACGAAGCCAAATCCAAGGAAGTCGCCACGG
ACATCGAAAAGAATGGGGGCACTGCGATTGCGGTTAAGCTCGATGTTTCAGATCGCGAGGGGTTTTTC
GCCGCTGTTAAAGAAGTCGCGGAGAAGCTTGGAGGTTTTGACGTCTTGGTAAACAACGCTGGGCTCGG
CCCCACCACCCCCATCGATACTATTACCCCGGAACTATTTGATAAGGTCTATCACATCAACGTCGCTG
GCGACATTTGGGGGATTCAAGCAGCCGTGGAGCAGTTCAAGAAAAATGGCAACGGCGGCAAAATCATT
AACGCGACAAGTCAAGCCGGCGTGGTCGGCAATCCTAATTTGTCTCTGTATAGCTCGACTAAGTTCGC
AGTGCGCGGACTGACGCAGGTCGCAGCGCGCGATCTAGCCGAACAGAATATCACGGTTAATGCGTACG
CTCCAGGAATTGTGAAAACGCCGATGATGTTTGATATTGCCCATGAAGTTGGCAAAAACGCCGGTAAG
GATGACGAGTGGGGTATGCAAACCTTCGCGAAAGATATCGCTCTCAAACGGCTGAGCGAACCCGAGGA
CGTCGCCGCTGCTGTTGCGTTCTTAGCAGGTCCTGACAGTAATTACATCACCGGTCAGACCATCGAAG
TGGATGGTGGCATGCAGTTTCACTAG SEQ ID NO: 19: *Leuconostoc pseudomesenteroides* CHCC2114 alcohol
dehydrogenase - adh amino acid sequence
MTKKVAMVTGGAQGIGEAIVRRLSADGFAVAVADLNEAKSKEVATDIEKNGGTAIAVKLDVSDREGFF
AAVKEVAEKLGGFDVLVNNAGLGPTTPIDTITPELFDKVYHINVAGDIWGIQAAVEQFKKNGNGGKII
NATSQAGVVGNPNLSLYSSTKFAVRGLTQVAARDLAEQNITVNAYAPGIVKTPMMFDIAHEVGKNAGK
DDEWGMQTFAKDIALKRLSEPEDVAAAVAFLAGPDSNYITGQTIEVDGGMQFH SEQ ID NO: 20: *Clostridium beijerinckii* NRRLB593 alcohol
dehydrogenase - adh gene nucleotide sequence
ATGAAAGGTTTTGCCATGCTTGGAATCAATAAGCTAGGCTGGATTGAAAAAGAACGCCCAGTGGCGGG
TAGTTATGATGCCATCGTTCGCCCACTGGCAGTGTCGCCCTGTACGAGCGATATCCACACCGTATTTG
AGGGCGCGTTAGGGGATCGTAAGAATATGATTCTGGGCCATGAAGCGGTTGGTGAGGTCGTAGAGGTG
GGGTCTGAAGTGAAAGATTTCAAACCCGGCGATCGCGTCATCGTCCCATCTACGCCGGACTGGCG
AAGCCTTGAAGTGCAGGCGGGATTCCAACAGCACTCAAACGGCATGCTCGCGGGGTGGAAGTTTTCCA
ACTTTAAGGACGGGGTGTTCGGGGAATACTTCCACGTCAACGATGCGGATATGAATTTAGCCATTTTG
CCTAAGGACATGCCCCTCGAAAATGCTGTTATGATTACCGATATGATGACAACGGGTTTCCACGGCGC
TGAGCTCGCTGATATCCAAATGGGCAGCAGTGTGGTTGTCATCGGGATTGGTGCAGTCGGCCTGATGG
GCATTGCGGGAGCCAAATTGCGGGGAGCTGGCCGCATCATTGGTGTTGGTAGCCGGCCTATTTGTGTC
GAAGCTGCAAAGTTTTATGGGGCCACAGACATTTGAACTACAAGAATGGTCATATTGTGGACCAGGT

| SEQUENCES |
|---|
| GATGAAGCTCACGAATGGCAAGGGAGTCGATCGCGTTATCATGGCTGGCGGTGGCTCTGAAACCCTGA<br>GCCAAGCAGTCTCGATGGTCAAACCGGGAGGCATTATCTCGAACATCAACTATCATGGCAGTGGCGAT<br>GCGCTGCTGATCCCCCGAGTGGAGTGGGGCTGCGGCATGGCCCATAAGACCATTAAAGGCGGCCTCTG<br>CCCCGGGTGGCCGTTTGCGCGCAGAGATGCTACGCGATATGGTGGTCTACAACCGGGTGGATCTGTCCA<br>AACTGGTCACTCACGTTTACCATGGTTTTGATCACATCGAAGAGGCCTTGTTGTTGATGAAAGACAAA<br>CCGAAAGACCTCATTAAAGCCGTCGTAATCCTGTAG<br><br>SEQ ID NO: 21: *Clostridium beijerinckii* NRRLB593 alcohol<br>dehydrogenase - adh amino acid sequence<br>MKGFAMLGINKLGWIEKERPVAGSYDAIVRPLAVSPCTSDIHTVFEGALGDRKNMILGHEAVGEVVEV<br>GSEVKDFKPGDRVIVPCTTPDWRSLEVQAGFQQHSNGMLAGWKFSNFKDGVFGEYFHVNDADMNLAIL<br>PKDMPLENAVMITDMMTTGFHGAELADIQMGSSVVVIGIGAVGLMGIAGAKLRGAGRIIGVGSRPICV<br>EAAKFYGATDILNYKNGHIVDQVMKLTNGKGVDRVIMAGGGSETLSQAVSMVKPGGIISNINYHGSGD<br>ALLIPRVEWGCGMAHKTIKGGLCPGGRLRAEMLRDMVVYNRVDLSKLVTHVYHGFDHIEEALLLMKDK<br>PKDLIKAVVIL<br><br>SEQ ID NO: 22: *Thermoanaerobacter brockii* HTD4 alcohol dehydrogenase -<br>adh gene nucleotide sequence<br>ATGAAGGGTTTCGCAATGCTGAGCATCGGGAAAGTCGGTTGGATCGAAAAAGAGAAACCTGCGCCAGG<br>CCCGTTCGACGCGATTGTTCGGCCCTTAGCTGTCGCGCCGTGCACGTCGGACATTCACACGGTATTCG<br>AAGGGGCTATCGGCGAGCGGCACAATATGATCCTGGGCCATGAAGCTGTCGGCGAGGTTGTCGAAGTG<br>GGCTCTGAGGTGAAAGACTTTAAACCCGGCGATCGCGTCGTAGTTCCGGCGATCACTCCCGACTGGCG<br>GACGAGTGAAGTGCAACGCGGCTATCACCAGCACAGCGGGGGAATGTTGGCGGGCTGGAAGTTTTCAA<br>ACGTCAAGGATGGGGTTTTTGGCGAATTCTTTCATGTGAACGATGCCGATATGAATCTGGCCCATCTT<br>CCTAAAGAGATTCCGCTGGAGGCTGCTGTGATGATTCCGGATATGATGACCACAGGCTTCCATGGTGC<br>TGAACTCGCGGATATCGAACTGGGTGCCACCGTGGCAGTGTTGGGCATCGGCCCTGTTGGCCTCATGG<br>CGGTCGCAGGTGCTAAGTTACGTGGGGCTGGCCGTATTATCGCCGTCGGCTCGCGCCCAGTGTGTGTT<br>GATGCGGCTAAGTACTATGGAGCCACTGATATCGTGAACTACAAGGATGGTCCCATCGAGAGTCAGAT<br>TATGAATTTGACCGAGGGAAAGGGTGTCGACGCCGCCATTATCGCAGGTGGAAACGCCGATATCATGG<br>CCACCGCCGTCAAAATCGTTAAACCTGGAGGTACAATTGCAAATGTCAACTATTTTGGTGAAGGCGAA<br>GTGCTGCCCGTTCCACGCCTGGAATGGGGATGTGGGATGCCCATAAGACCATTAAAGGCGGCCTCTG<br>CCCCGGTGGCCGACTGCGCATGGAACGCCTAATTGATCTCGTGTTCTACAAACGAGTCGATCCGTCCA<br>AGTTGGTGACGCACGTGTTTCGCGGTTTTGACAATATTGAGAAGGCATTTATGCTAATGAAGGACAAA<br>CCGAAAGATCTCATCAAACCCGTGGTCATTTTGGCA<br><br>SEQ ID NO: 23: *Thermoanaerobacter brockii* HTD4 alcohol dehydrogenase -<br>adh amino acid sequence<br>MKGFAMLSIGKVGWIEKEKPAPGPFDAIVRPLAVAPCTSDIHTVFEGAIGERHNMILGHEAVGEVVEV<br>GSEVKDFKPGDRVVVPAITPDWRTSEVQRGYHQHSGGMLAGWKFSNVKDGVFGEFFHVNDADMNLAHL<br>PKEIPLEAAVMIPDMMTTGFHGAELADIELGATVAVLGIPVGLMAVAGAKLRGAGRIIAVGSRPVCV<br>DAAKYYGATDIVNYKDGPIESQIMNLTEGKGVDAAIIAGGNADIMATAVKIVKPGGTIANVNYFGEGE<br>VLPVPRLEWGCGMAHKTIKGGLCPGGRLRMERLIDLVFYKRVDPSKLVTHVFRGFDNIEKAFMLMKDK<br>PKDLIKPVVILA |

We claim:

1. A cyanobacterium comprising a recombinant polynucleotide encoding an acetolactate synthase (ALS) and an acetolactate decarboxylase (ALDC), wherein the ALS is a *Bacillus sp.* ALS and the ALDC is an *Enterobacter sp.* ALDC or an *Aeromonas sp.* ALDC, and wherein expression of the ALS and the ALDC results in an increase in production of acetoin as compared to a corresponding cyanobacterium lacking the polynucleotide.

2. A cyanobacterium comprising a recombinant polynucleotide encoding an acetolactate synthase (ALS), an acetolactate decarboxylase (ALDC) and a secondary alcohol dehydrogenase (sADH), wherein the sADH is selected from the group consisting of a *Candida sp.* sADH, a *Leuconostoc sp.* sADH, a *Clostridium sp.* sADH, and a *Thermoanaerobacter sp.* sADH, and wherein expression of the ALS, the ALDC and the sADH results in an increase in production of one or both of acetoin and 2,3-butanediol (23BD) as compared to a corresponding cyanobacterium lacking the polynucleotide.

3. The cyanobacterium of claim 2 wherein the ALS is a bacterial ALS, the ALDC is a bacterial ALDC or a fungal ALDC.

4. The cyanobacterium of claim 3, wherein the ALS is a *Bacillus sp.* ALS.

5. The cyanobacterium of claim 3, wherein the ALDC is selected from the group consisting of an *Enterobacter sp.* ALDC, a *Bacillus sp.* ALDC, an *Aeromonas sp.* ALDC, and a *Gluconacetobacter sp.* ALDC.

6. The cyanobacterium of claim 3, wherein the ALDC is selected from the group consisting of an *Enterobacter aerogenes* ALDC, an *Enterobacter cloacae* ALDC, a *Bacillus licheniformis* ALDC, a *Bacillus subtilis* ALDC, an *Aeromonas hydrophila* ALDC, and a*Gluconacetobacter xylinus* ALDC.

7. The cyanobacterium of claim 3, wherein the sADH is selected from the group consisting of a *Candida sp*, sADH, and a *Leuconostoc sp.* ADH.

8. The cyanobacterium of claim 3, wherein the sADH is selected from the group consisting of a *Candida parapsilosis* sADH, a *Leuconostoc pseudomesenteroides* sADH, a*Clostridium beijerinckii* sADH, and a *Thermoanaerobacter brockii* sADH.

9. The cyanobacterium of claim 3, wherein the expression of the ALS and the ALDC, or the expression of the ALS, the ALDC and the sADH is driven by an inducible promoter.

10. The cyanobacterium of claim 3, wherein the polynucleotide is stably integrated into the genome of the cyanobacterium.

11. The cyanobacterium of claim 3, wherein the cyanobacterium is selected from the group consisting of *Nostoc sp.*, *Synechococcus sp.*, *Synechocystis sp.*, and*Thermosynechococcus sp.*

12. The cyanobacterium of claim 11, wherein the cyanobacterium is a*Synechococcus sp.*

13. The cyanobacterium of claim 3, wherein the production of one or both of acetoin and 2,3-butanediol (23BD) occurs as a result of culturing the cyanobacterium under constant light.

14. The cyanobacterium of claim 3, wherein the production of one or both of acetoin and 2,3-butanediol (23BD) occurs as a result of culturing the cyanobacterium in the presence of bicarbonate.

15. The cyanobacterium of claim 3, wherein the ALDC is essentially insensitive to oxygen.

16. The cyanobacterium of claim 3, wherein the sADH is essentially insensitive to oxygen and is NADPH-dependent.

17. A method of producing acetoin, the method comprising:
  a) providing the cyanobacterium of claim 1,
  b) culturing the cyanobacterium in a photosynthetic environment comprising $CO_2$ and light whereby the expression of the ALS and the ALDC results in production of acetoin.

18. The method of claim 17, wherein the production of acetoin occurs at a higher level than that produced by culturing the corresponding cyanobacterium lacking the polynucleotide under the same conditions.

19. A method of producing 2,3-butanediol, the method comprising:
  a) providing a cyanobacterium of claim 2;
  b) culturing the cyanobacterium in a photosynthetic environment comprising $CO_2$ and light whereby expression of the ALS, the ALDC and the sADH results in production of 2,3-butanediol.

20. The method of claim 19, wherein the production of 2,3-butanediol occurs at a higher level than that produced by culturing the corresponding cyanobacterium lacking the polynucleotide under the same conditions.

* * * * *